US006177410B1

(12) United States Patent
Holt et al.

(10) Patent No.: US 6,177,410 B1
(45) Date of Patent: Jan. 23, 2001

(54) THERAPEUTIC METHODS FOR PROSTATE CANCER

(75) Inventors: Jeffrey T. Holt, Brentwood; Roy A. Jensen, Franklin, both of TN (US); Mary-Claire King, Seattle, WA (US); Mitchell S. Steiner, Germantown, TN (US); Cheryl L. Robinson-Benion; Marilyn E. Thompson, both of Nashville, TN (US)

(73) Assignees: Vanderbilt University, Nashville, TN (US); The University of Washington, Seattle, WA (US)

( * ) Notice: Under 35 U.S.C. 154(b), the term of this patent shall be extended for 0 days.

(21) Appl. No.: 08/986,106

(22) Filed: Dec. 5, 1997

(51) Int. Cl.$^7$ ............................. A61K 48/00; C12N 15/63
(52) U.S. Cl. .......................................... 514/44; 435/320.1
(58) Field of Search ............................ 514/44; 435/320.1

(56) References Cited

U.S. PATENT DOCUMENTS

| 4,675,285 | 6/1987 | Clark et al. ............................... 435/6 |
| 5,399,346 | 3/1995 | Anderson et al. ................ 424/93.21 |
| 5,434,064 | 7/1995 | Schlessinger et al. ............. 435/172.3 |
| 5,654,155 | 8/1997 | Murphy et al. ........................... 435/6 |

FOREIGN PATENT DOCUMENTS

| 0699754 A1 | 3/1996 | (EP) ............................. C12N/15/12 |
| 0705902 A1 | 4/1996 | (EP) ............................. C12N/15/12 |
| 0705903 A1 | 4/1996 | (EP) ............................. C12N/15/12 |
| WO 95/19369 | 7/1995 | (WO) ............................. C07H/21/02 |
| WO 95/25429 | 9/1995 | (WO) ............................ A01K/067/00 |
| WO 95/25813 | 9/1995 | (WO) ........................... C12Q/001/68 |
| WO 96/05306 | 2/1996 | (WO) ........................... C12N/015/12 |
| WO 96/05307 | 2/1996 | (WO) ........................... C12N/015/12 |
| WO 96/05308 | 2/1996 | (WO) ........................... C12N/015/12 |
| WO 97/29213 | 8/1997 | (WO) ............................. C12Q/1/68 |
| WO 97/301308 | 8/1997 | (WO) .............................. C08H/1/00 |

OTHER PUBLICATIONS

Orkin et al. (Dec. 1995) "Report and Recommendations of the panel to assess the NIH investment in research on gene therapy".*
Marshall et al. (Aug. 1995) Science, vol. 269, 1050–1055.*
Verma et al. (Sep. 1997) Science, vol. 389, 239–242.*
James, W. (1991) Antiviral Chem. & Chemotherapy, vol. 2, 191–241.*
Wooster et al., "Identification of the Breast Cancer Susceptibility Gene BRCA2", Nature, vol. 378, (Dec. 21,28, 1995), pp. 789–792.
Miki et al., "A Strong Candidate for the Breast and Ovarian Cancer Susceptibility Gene BRCA1", Science, vol. 1, (Oct. 7, 1994), pp. 66–71.
Holt et al., "Growth Retardation and Tumour Inhibition by BRCA1", Nature Genetics, vol. 12, (Mar. 1996), pp. 298–302.

Ormiston, "Hereditary Breast Cancer", European Journal of Cancer Care, vol. 5, (1996), pp. 13–20.
Jones et al., "Molecular Genetics of Sporadic and Familial Breast Cancer", Cancer Surveys, vol. 25, (1995), pp. 315–334.
"Molecular Biology/Biochemistry", Proceedings of the American Association for Cancer Research, vol. 37, (Mar. 1996), p. 516.
Chen et al., "Aberrant Subcellular Localization of BRCA1 in Breast Cancer", Science, vol. 270, (Nov. 3, 1995), pp. 789–791.
Cornelius et al., "High Allele Loss Rates at 17q12–q21 in Breast and Ovarian Tumors from BRCA1–Linked Families", Genes, Chromosomes & Cancer, vol. 13, (1995), pp. 201–210.
Gayther et al., "Germline Mutations of the BRCA1 Gene in Breast and Ovarian Cancer Families Provide Evidence for a Genotype–Phenotype Correlation", Nature Genetics, vol. 11, (Dec. 1995), pp. 428–433.
Gudas et al., "Hormone–Dependent Regulation of BRCA1 in Human Breast Cancer Cells", Cancer Research, vol. 55, (Oct. 15, 1995), pp. 4561–4565.
Hosking eet al., "A Somatic BRCA1 Mutation in an Ovarian Tumour", Nature Genetics, vol. 9, (Apr. 1995), pp. 343–344.
Huttner et al., "The Granin (Chromogranin/Secretogranin) Family", TIBS, vol. 16, (Jan. 1991), pp. 27–30.
Marquis et al., "The Developmental Pattern of BRCA1 Expression Implies a Role in Differentiation of the Breast and Other Tissues", Nature Genetics, vol. 11, (Sep. 1995), pp. 17–26.
Merajver et al., "Somatic Mutations in the BRCA1 Gene in Sporadic Ovarian Tumours", Nature Genetics, vol. 9, (Apr. 1995), pp. 439–443.
Thompson et al., "Decreased Expression of BRCA1 Accelerates Growth and is Often Present During Sporadic Breast Cancer Progression", Nature Genetics, vol. 9, (Apr. 1995), pp. 444–450.
Lemoine, "Molecular Biology of Breast Cancer", Symposium Article, pp. 31–37.
Weber et al., "Familial Breast Cancer", Cancer Supplement, vol. 74, No. 3, (Aug. 1, 1994), pp. 1013–1020.
Takahashi et al., "Mutation Analysis of the BRCA1 Gene in Ovarian Cancers", Cancer Research, vol. 55, (Jul. 15, 1995), pp. 2998–3002.

(List continued on next page.)

* cited by examiner

Primary Examiner—Jasemine Chambers
Assistant Examiner—AnneMarie S. Beckerleg
(74) Attorney, Agent, or Firm—Jenkins & Wilson, P.A.

(57) ABSTRACT

Therapeutic methods for the treatment of prostate cancer are described. The methods include a gene therapy method for prostate cancer using the BRCA family of genes, including the BRCA1 and BRCA2 genes. The BRCA family of gene products inhibit the growth and tumorigenesis of prostate cancer cells. Therapeutic methods using the BRCA family of gene products are also described.

8 Claims, 19 Drawing Sheets

OTHER PUBLICATIONS

Narod, "Genetics of Breast and Ovarian Cancer", *British Medical Bulletin*, vol. 50, No. 3, (1994), pp. 656–676.

Hall et al., "Linkage of Early–Onset Familial Breast Cancer to Chromosome 17q21", *Science*, vol. 250, (Dec. 21, 1990), pp. 1684–1689.

Helzlsouer, "Epidemiology, Prevention and Early Detection of Breast Cancer", *Oncology*, vol. 7, (1995), pp. 489–494.

Szabo et al., "Inherited Breast and Ovarian Cancer", *Human Molecular Genetics*, vol. 4, pp. 1811–1817.

Easton et al., "Inherited Susceptibility to Breast Cancer", *Cancer Surveys*, vol. 18, pp. 95–113.

Steeg, "Granin Expectations in Breast Cancer?", *Nature Genetics*, vol. 12, (Mar. 1996), pp. 223–225.

Burtness, "Oncology and Hematology", *JAMA*, vol. 273, No. 21, (Jun. 7, 1995), pp. 1702–1703.

Hopkin, "MTS1, Telomerase May be New Targets for Cancer Therapy", *The Journal of NIH Research*, vol. 6, (Jun. 1994), pp. 38–42.

Norris et al., "Identification of a New Subclass of Alu DNA Repeats Which Function as Estrogen Receptor–Dependent Transcriptional Enhancers", *Journal of Biological Chemistry*, vol. 270, No. 39, (Sep. 29, 1995), pp. 22777–22782.

Davis et al., "$S_1$ Nuclease Protection Assay", *Basic Methods in Molecular Biology*, (1986), pp. 276–284.

Futreal et al., "BRCA1 Mutations in Primary Breast and Ovarian Carcinomas", *Science*, vol. 266, (Oct. 7, 1994), pp. 120–122.

Holt et al., "Histopathology: Old Principles and New Methods", *Cancer Surveys*, vol. 18, (1993), pp. 1–24.

Liang et al., "Differential Display and Cloning of Messenger RNAs from Human Breast Cancer versus Mammary Epithelial Cells", *Cancer Research*, vol. 52, (Dec. 15, 1992), pp. 6966–6968.

Campbell et al., "A Novel Gene Encoding a B–Box Protein Within the BRCA1 Region at 17q21.1", *Human Molecular Genetics*, vol. 3, No. 4, (1994), pp. 589–594.

Narod et al., "An Evaluation of Genetic Heterogeneity in 145 Breast–Ovarian Cancer Families", *Am. J. Hum. Genet.*, vol. 56, (1995), pp. 254–264.

Marcus et al., "Pathology and Heredity of Breast Cancer in Younger Women", *Journal of the National Cancer Institute Monographs*, No. 16, (1994), pp. 23–33.

Porter et al., "Breast Cancer Incidence, Penetrance and Survival in Probable Carriers of BRCA1 Gene Mutation in Families Linked to BRCA1 on Chromosome 17q12–21", *British Journal of Surgery*, vol. 81, (1994), pp. 1512–1515.

Merlo et al., "Evidence for a Second Tumor Suppressor Gene on 17p Linked to High S–Phase Index in Primary Human Breast Carcinomas", *Cancer Genet. Cytogenet.*, vol. 76, (1994), pp. 106–111.

Neuhausen et al., "Loss of Heterozygosity in Familila Tumors from Three BRCA1–Linked Kindreds", *Cancer Research*, vol. 54, (Dec. 1, 1994), pp. 6069–6071.

Brown et al., "Regulation of BRCA1", *Nature*, vol. 372, (Dec. 22,29, 1994), p. 733.

Simard et al., "Common Origins of BRCA1 Mutations in Canadian Breast and Ovarian Cancer Families", *Nature Genetics*, vol. 8, (Dec. 1994).

Castilla et al., "Mutations in the BRCA1 Gene in Families with Early–Onset Breast and Ovarian Cancer", *Nature Genetics*, vol. 8, (Dec. 1994), pp. 387–391.

Friedman et al., "Confirmation of BRCA1 by Analysis of Germline Mutations Linked to Breast and Ovarian Cancer in Ten Families", *Nature Genetics*, pp. 1–6.

Gunzburg et al., "Virus Vector Design in Gene Therapy", *Molecular Medicine Today*, (1995), pp. 410–417.

Reeck et al., "'Homology' in Proteins and Nucleic Acids: A Terminology Muddle and a Way Out of It", *Cell*, vol. 50(Aug. 28, 1987), p. 667.

Ledley, "Nonviral Gene Therapy: The Promise of Genes as Pharmaceutical Products", *Human Gene Therapy*, vol. 6, (Sep. 1995), pp. 1129–1144.

Marshall, "Less Hype, More Biology Needed for Gene Therapy", *Science* (Dec. 1995), p. 1751.

Coghlan, "Gene Dream Fades Away", *New Scientist*, (Nov. 1995).

Jain, "Barriers to Drug Delivery in Solid Tumors", *Scientific American*, (Jul. 1994), pp. 58–65.

Mastrangelo et al., "Gene Therapy for Human Cancer: An Essay for Clinicians", *Seminars in Oncology*, vol. 23, No. 1, (Feb. 1996), pp. 4–21.

Wallace et al., "Oligonucleotide Probes for the Screening of Recombinant DNA Libraries", *Methods in Enzymology*, vol. 152, (1987), pp. 432–443.

Sambrook et al., "Estimating the Effects of Mismatches", *Molecular Cloning*, (1989), CSH 11.47.

(Abstract only) Neuhold et al., "Dioxin–inducible Enhancer Region Upstream from the Mouse P–1450 Gene and Interaction with a Heterologous SV–40 Promoter", *DNA*, vol. 5 (1986), pp. 403–412.

Langston et al., "BRCA1 Mutations in a Population–Based Sample of Young Women with Breast Cancer", *The New England Journal of Medicine*, vol. 334, No. 3, pp. 137–142.

Bieche et al. "Genetic Alterations in Breast Cancer", *Genes, Chromosomes & Cancer*, vol. 14 (1995), pp. 227–251.

Table of the Genetic Code

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

FIG. 2

| | | | | | | | | | | |
|---|---|---|---|---|---|---|---|---|---|---|
| Majority | E | N | L | S | A | E | D | E | E | L |
| Human BRCA1 | E | N | L | S | S | E | D | E | E | L | [SEQ ID NO: 6] |
| Monkey BRCA1 | E | N | L | S | S | E | D | E | E | L | [SEQ ID NO: 7] |
| Mouse BRCA1 | E | S | D | S | T | E | D | E | D | L | [SEQ ID NO: 8] |
| Chromogranin A | E | S | L | S | A | I | E | A | E | L | [SEQ ID NO: 10] |
| Chromogranin B | E | N | L | A | A | M | D | L | E | L | [SEQ ID NO: 14] |
| Secretogranin II | E | N | L | N | D | K | D | Q | E | L | [SEQ ID NO: 17] |

Consensus

|   |   |   | S |   |   |   |   |   |   |   |
|---|---|---|---|---|---|---|---|---|---|---|
| E | N | L | A | X | X | D | X | E | L | [SEQ ID NO: 5] |
| D | S |   | N |   |   | E |   | D |   |

The probability that BRCA1 would contain a polypeptide that would satisfy the granin consensus by chance alone is approximately 1 in 55. This calculation is based on the following rationale:

$$(N-n+1) \prod_{i=1}^{n} \sum^{k} A_i$$

Where   $n$ = length of the consensus sequence
        $k$ = number of alternative amino acids at site $i$ of the consensus
        $A_i$ = frequency of amino acid i in the entire sequence N amino acids long

| AA1 | AA2 | AA3 | AA4 | AA5 | AA6 | AA7 | AA8 | AA9 | AA10 | N-n+1 | Probability |
|---|---|---|---|---|---|---|---|---|---|---|---|
|  |  |  | S |  |  |  |  |  |  |  |  |
| E | N | L | A | X | X | D | X | E | L |  |  |
| D | L |  | N |  |  | E |  | D |  |  |  |
| 0.15 |  | 0.08 |  | 1.0 | 1.0 |  | 1.0 |  | 0.08 | 1854 | = 0.0018 |
|  | 0.19 |  | 0.23 |  |  | 0.15 |  | 0.15 |  |  |  |

Note that this does not take into account the likelihood of amino acid pairs that frequently co-occur.

FIG. 4

Granin Sequences

| Granin | Species | Amino Acid | | | | | | | | |
|---|---|---|---|---|---|---|---|---|---|---|
| Consensus | | E<br>D | N<br>S | L | S<br>A<br>N | X | X | D<br>E | X | E<br>D | L [SEQ ID NO: 5] |
| BRCA1 | Human | E | N | L | S | S | E | D | E | E | L [SEQ ID NO: 6] |
| | Rhesus | E | N | L | S | S | E | D | E | E | L [SEQ ID NO: 7] |
| | Mouse | E | S | D | S | T | E | D | E | D | L [SEQ ID NO: 8] |
| BRCA2 | Human | E | S | N | S | I | A | D | E | E | L [SEQ ID NO: 9] |
| Chromogranin A | Human | E | S | L | S | A | I | E | A | E | L [SEQ ID NO: 10] |
| | Bovine | E | S | L | S | A | I | E | A | E | L [SEQ ID NO: 11] |
| | Rat | E | S | L | S | A | I | E | A | E | L [SEQ ID NO: 12] |
| | Pig | E | S | L | S | A | I | E | A | E | L [SEQ ID NO: 13] |
| Chromogranin B | Human | E | N | L | A | A | M | D | L | E | L [SEQ ID NO: 14] |
| | Bovine | E | N | L | A | A | M | D | L | E | L [SEQ ID NO: 15] |
| | Mouse | E | N | L | A | A | M | D | L | E | L [SEQ ID NO: 16] |
| Secretogranin II | Human | E | N | L | N | D | K | D | Q | E | L [SEQ ID NO: 17] |
| | Bovine | E | N | L | N | D | K | D | Q | E | L [SEQ ID NO: 18] |
| | Rat | D | N | L | N | D | K | D | Q | E | L [SEQ ID NO: 19] |
| | Mouse | E | N | L | N | - | - | D | Q | E | L [SEQ ID NO: 20] |
| Secretogranin III | Rat | E | N | L | D | E | T | I | A | L | Q [SEQ ID NO: 21] |
| | Mouse | E | N | L | D | E | T | I | A | L | Q [SEQ ID NO: 22] |
| Secretogranin V | Human | G | N | I | P | N | I | V | A | E | L [SEQ ID NO: 23] |
| | Pig | G | N | I | P | N | I | V | A | E | L [SEQ ID NO: 24] |
| | Rat | G | N | I | P | N | I | V | A | E | L [SEQ ID NO: 25] |
| | Xenopus | G | N | I | P | N | I | V | A | E | L [SEQ ID NO: 26] |
| Frequency of consensus amino acid in complete BRCA1 sequence | | 0.15 | 0.19 | 0.08 | 0.23 | 1 | 1 | 0.15 | 1 | 0.15 | 0.08 |

FIG. 5

Gene sequence for BRCA1 [SEQ ID NO: 1]
(reference Miki et al. Science 266:66, 1994)

agctcgctgagacttcctggaccccgcaccaggctgtggggtttctcagataactgggcccctgcgctca ggaggccttcaccctctgctctgggtaaagttcattggaacagaaagaaatggatttatctgctcttcgcgt tgaagaagtacaaaatgtcattaatgctatgcagaaaatcttagagtgtcccatctgtctggagttgatcaa ggaacctgtctccacaaagtgtgaccacatattttgcaaattttgcatgctgaaacttctcaaccagaagaa agggccttcacagtgtcctttatgtaagaatgatataaccaaaaggagcctacaagaaagtacgagattta gtcaacttgttgaagagctattgaaaatcatttgtgcttttcagcttgacacaggtttggagtatgcaaacag ctataattttgcaaaaaggaaaataactctcctgaacatctaaaagatgaagtttctatcatccaaagtatg ggctacagaaaccgtgccaaaagacttctacagagtgaacccgaaaatccttccttgcaggaaaccagtc tcagtgtccaactctctaaccttggaactgtgagaactctgaggacaaagcagcggatacaacctcaaaa gacgtctgtctacattgaattgggatctgattcttctgaagataccgttaataaggcaacttattgcagtgtg ggagatcaagaattgttacaaatcacccctcaaggaaccagggatgaaatcagtttggattctgcaaaaa aggctgcttgtgaattttctgagacggatgtaacaaatactgaacatcatcaacccagtaataatgatttgaa caccactgagaagcgtgcagctgagaggcatccagaaaagtatcagggtagttctgtttcaaacttgcat gtggagccatgtggcacaaatactcatgccagctcattacagcatgagaacagcagtttattactcactaa agacagaatgaatgtagaaaaggctgaattctgtaataaaagcaaacagcctggcttagcaaggagcca acataacagatgggctggaagtaaggaaacatgtaatgataggcggactcccagcacagaaaaaaagg tagatctgaatgctgatcccctgtgtgagagaaaagaatggaataagcagaaactgccatgctcagagaa tcctagagatactgaagatgttccttggataacactaaatagcagcattcagaaagttaatgagtggttttcc agaagtgatgaactgttaggttctgatgactcacatgatggggagtctgaatcaaatgccaaagtagctga tgtattggacgttctaaatgaggtagatgaatattctggttcttcagagaaaatagacttactggccagtgat cctcatgaggctttaatatgtaaaagtgaaagagttcactccaaatcagtagagagtaatattgaagacaaa atatttgggaaaacctatcggaagaaggcaagcctccccaacttaagccatgtaactgaaaatctaattata

FIG. 6A ggagcatttgttactgagccacagataatacaagagcgtcccctcacaaataaattaaagcgtaaaagga
gacctacatcaggccttcatcctgaggattttatcaagaaagcagatttggcagttcaaaagactcctgaaa
tgataaatcagggaactaaccaaacggagcagaatggtcaagtgatgaatattactaatagtggtcatga
gaataaaacaaaaggtgattctattcagaatgagaaaaatcctaacccaatagaatcactcgaaaaagaat
ctgctttcaaaacgaaagctgaacctataagcagcagtataagcaatatggaactcgaattaaatatccac
aattcaaaagcacctaaaaagaataggctgaggaggaagtcttctaccaggcatattcatgcgcttgaact
agtagtcagtagaaatctaagcccacctaattgtactgaattgcaaattgatagttgttctagcagtgaaga
gataaagaaaaaaagtacaaccaaatgccagtcaggcacagcagaaacctacaactcatggaaggta
aagaacctgcaactggagccaagaagagtaacaagccaaatgaacagacaagtaaaagacatgacag
cgatactttcccagagctgaagttaacaaatgcacctggttctttactaagtgttcaaataccagtgaactta
aagaatttgtcaatcctagccttccaagagaagaaaaagaagagaaactagaaacagttaaagtgtctaat
aatgctgaagaccccaaagatctcatgttaagtggagaaagggttttgcaaactgaaagatctgtagaga
gtagcagtatttcattggtacctggtactgattatggcactcaggaaagtatctcgttactggaagttagcac
tctagggaaggcaaaaacagaaccaaataaatgtgtgagtcagtgtgcagcatttgaaaaccccaaggg
actaattcatggttgttccaaagataatagaaatgacacagaaggctttaagtatccattgggacatgaagt
taaccacagtcgggaaacaagcatagaaatggaagaaagtgaacttgatgctcagtatttgcagaataca
ttcaaggtttcaaagcgccagtcatttgctccgttttcaaatccaggaaatgcagaagaggaatgtgcaac
attctctgcccactctgggtccttaaagaaacaaagtccaaaagtcacttttgaatgtgaacaaaaggaag
aaaatcaaggaaagaatgagtctaatatcaagcctgtacagacagttaatatcactgcaggctttcctgtg
gttggtcagaaagataagccagttgataatgccaaatgtagtatcaaaggaggctctaggttttgtctatca
tctcagttcagaggcaacgaaactggactcattactccaaataaacatggacttttacaaaacccatatcgt
ataccaccacttttttcccatcaagtcatttgttaaaactaaatgtaagaaaaatctgctagaggaaaactttga
ggaacattcaatgtcacctgaaagagaaatgggaaatgagaacattccaagtacagtgagcacaattagc
cgtaataacattagagaaaatgtttttaaagaagccagctcaagcaatattaatgaagtaggttccagtact
aatgaagtgggctccagtattaatgaaataggttccagtgatgaaaacattcaagcagaactaggtagaa acagagggccaaaattgaatgctatgcttagattaggggttttgcaacctgaggtctataaacaaagtcttc
ctggaagtaattgtaagcatcctgaaataaaaaagcaagaatatgaagaagtagttcagactgttaataca
gatttctctccatatctgatttcagataacttagaacagcctatgggaagtagtcatgcatctcaggtttgttct
gagacacctgatgacctgttagatgatggtgaaataaaggaagatactagttttgctgaaaatgacattaa
ggaaagttctgctgttttagcaaaagcgtccagaaaggagagcttagcaggagtcctagccctttcaccc
atacacatttggctcagggttaccgaagaggggccaagaaattagagtcctcagaagagaacttatctag
tgaggatgaagagcttccctgcttccaacacttgttatttggtaaagtaaacaatataccttctcagtctacta
ggcatagcaccgttgctaccgagtgtctgtctaagaacacagaggagaatttattatcattgaagaatagc
ttaaatgactgcagtaaccaggtaatattggcaaaggcatctcaggaacatcaccttagtgaggaaacaa
aatgttctgctagcttgttttcttcacagtgcagtgaattggaagacttgactgcaaatacaaacacccagg
atcctttcttgattggttcttccaaacaaatgaggcatcagtctgaaagccagggagttggtctgagtgaca
aggaattggtttcagatgatgaagaaagaggaacgggcttggaagaaaataatcaagaagagcaaagc
atggattcaaacttaggtgaagcagcatctgggtgtgagagtgaaacaagcgtctctgaagactgctcag
ggctatcctctcagagtgacattttaaccactcagcagagggataccatgcaacataacctgataaagctc
cagcaggaaatggctgaactagaagctgtgttagaacagcatgggagccagccttctaacagctacccctt
ccatcataagtgactcttctgcccttgaggacctgcgaaatccagaacaaagcacatcagaaaaagcagt
attaacttcacagaaaagtagtgaatacccataagccagaatccagaaggcctttctgctgacaagtttga
ggtgtctgcagatagttctaccagtaaaaataaagaaccaggagtggaaaggtcatccccttctaaatgcc
catcattagatgataggtggtacatgcacagttgctctgggagtcttcagaatagaaactacccatctcaag
aggagctcattaaggttgttgatgtggaggagcaacagctggaagagtctgggccacacgatttgacgg
aaacatcttacttgccaaggcaagatctagagggaaccccttacctggaatctggaatcagcctcttctctg
atgaccctgaatctgatccttctgaagacagagccccagagtcagctcgtgttggcaacataccatcttca
acctctgcattgaaagttccccaattgaaagttgcagaatctgcccagagtccagctgctgctcatactact
gatactgctgggtataatgcaatggaagaaagtgtgagcagggagaagccagaattgacagcttcaaca
gaaagggtcaacaaaagaatgtccatggtggtgtctggcctgaccccagaagaatttatgctcgtgtaca agtttgccagaaaacaccacatcactttaactaatctaattactgaagagactactcatgttgttatgaaaac
agatgctgagtttgtgtgtgaacggacactgaaatattttctaggaattgcgggaggaaaatgggtagtta
gctatttctgggtgacccagtctattaaagaaagaaaaatgctgaatgagcatgatttgaagtcagagga
gatgtggtcaatggaagaaaccaccaaggtccaaagcgagcaagagaatcccaggacagaaagatctt
caggggggctagaaatctgttgctatgggcccttcaccaacatgcccacagatcaactggaatggatggta
cagctgtgtggtgcttctgtggtgaaggagctttcatcattcacccttggcacaggtgtccacccaattgtg
gttgtgcagccagatgcctggacagaggacaatggcttccatgcaattgggcagatgtgtgaggcacct
gtggtgacccgagagtgggtgttggacagtgtagcactctaccagtgccaggagctggacacctacctg
atacccccagatcccccacagccactactgat

FIG. 6D

Sequence of the BRCA2 cDNA [SEQ ID NO: 3]

ggtggcgcgagcttctgaaactaggcggcagaggcggagccgctgtggcactgctgcgcctctgctgcgcc tcgggtgtcttttgcggcggtgggtcgccgccgggagaagcgtgaggggacagatttgtgaccggcgcggt ttttgtcagcttactccggccaaaaaagaactgcacctctggagcggacttatttaccaagcattggaggaatatc gtaggtaaaaatgcctattggatccaaagagaggccaacatttttgaaattttaagacacgctgcaacaaagc agatttaggaccaataagtcttaattggtttgaagaactttcttcagaagctccaccctataattctgaacctgcag aagaatctgaacataaaaacaacaattacgaaccaaacctatttaaaactccacaaaggaaaccatcttataatca gctggcttcaactccaataatattcaaagagcaagggctgactctgccgctgtaccaatctcctgtaaaagaatta gataaattcaaattagacttaggaaggaatgttcccaatagtagacataaaagtcttcgcacagtgaaaactaaa atggatcaagcagatgatgtttcctgtccacttctaaattcttgtcttagtgaaagtcctgttgttctacaatgtacac atgtaacaccacaaagagataagtcagtggtatgtgggagtttgtttcatacaccaaagtttgtgaagggtcgtc agacaccaaaacatatttctgaaagtctaggagctgaggtggatcctgatatgtcttggtcaagttctttagctac accacccacccttagttctactgtgctcatagtcagaaatgaagaagcatctgaaactgtatttcctcatgatacta ctgctaatgtgaaaagctattttccaatcatgatgaaagtctgaagaaaaatgatagatttatcgcttctgtgaca gacagtgaaaacacaaatcaaagagaagctgcaagtcatggatttggaaaaacatcagggaattcatttaaagt aaatagctgcaaagaccacattggaaagtcaatgccaaatgtcctagaagatgaagtatatgaaacagttgtag atacctctgaagaagatagttttcattatgttttctaaatgtagaacaaaaaatctacaaaaagtaagaactagca agactaggaaaaaattttccatgaagcaaacgctgatgaatgtgaaaaatctaaaaaccaagtgaaagaaaaa tactcatttgtatctgaagtggaaccaaatgatactgatccattagattcaaatgtagcacatcagaagccctttga gagtggaagtgacaaaatctccaaggaagttgtaccgtctttggcctgtgaatggtctcaactaaccctttcagg tctaaatggagcccagatggagaaaataccctattgcatatttcttcatgtgaccaaaatatttcagaaaaagac ctattagacacagagaacaaaagaaagaaagattttcttacttcagagaattctttgccacgtatttctagcctacc aaaatcagagaagccattaaatgaggaaacagtggtaaataagagagatgaagagcagcatcttgaatctcat acagactgcattcttgcagtaaagcaggcaatatctggaacttctccagtggcttcttcatttcagggtatcaaaa agtctatattcagaataagagaatcacctaaagagactttcaatgcaagttttcaggtcatatgactgatccaaac

FIG. 7A tttaaaaaagaaactgaagcctctgaaagtggactggaaatacatactgtttgctcacagaaggaggactcctta tgtccaaatttaattgataatggaagctggccagccaccaccacacagaattctgtagctttgaagaatgcaggtt taatatccactttgaaaaagaaaacaaataagtttatttatgctatacatgatgaaacattttataaaggaaaaaaaa taccgaaagaccaaaaatcagaactaattaactgttcagcccagtttgaagcaaatgcttttgaagcaccacttac atttgcaaatgctgattcaggtttattgcattcttctgtgaaaagaagctgttcacagaatgattctgaagaaccaa ctttgtccttaactagctcttttgggacaattctgaggaaatgttctagaaatgaaacatgttctaataatacagtaat ctctcaggatcttgattataaagaagcaaaatgtaataaggaaaaactacagttatttattaccccagaagctgatt ctctgtcatgcctgcaggaaggacagtgtgaaaatgatccaaaaagcaaaaaagtttcagatataaaagaaga ggtcttggctgcagcatgtcacccagtacaacattcaaaagtggaatacagtgatactgactttcaatcccagaa aagtcttttatatgatcatgaaaatgccagcactcttatttttaactcctacttccaaggatgttctgtcaaacctagtc atgatttctagaggcaaagaatcatacaaaatgtcagacaagctcaaaggtaacaattatgaatctgatgttgaat taaccaaaaatattcccatggaaaagaatcaagatgtatgtgctttaaatgaaaattataaaaacgttgagctgttg ccacctgaaaaatacatgagagtagcatcaccttcaagaaaggtacaattcaaccaaaacacaaatctaagagt aatccaaaaaaatcaagaagaaactacttcaatttcaaaaataactgtcaatccagactctgaagaacttttctcag acaatgagaataattttgtcttccaagtagctaatgaaaggaataatcttgctttaggaaatactaaggaacttcat gaaacagacttgacttgtgtaaacgaacccattttcaagaactctaccatggttttatatggagacacaggtgata aacaagcaacccaagtgtcaattaaaaaagatttggtttatgttcttgcagaggagaacaaaaatagtgtaaagc agcatataaaaatgactctaggtcaagatttaaaatcggacatctccttgaatatagataaaataccagaaaaaaa taatgattacatgaacaaatgggcaggactcttaggtccaatttcaaatcacagttttggaggtagcttcagaaca gcttcaaataaggaaatcaagctctctgaacataacattaagaagagcaaaatgttcttcaaagatattgaagaac aatatcctactagtttagcttgtgttgaaattgtaaataccttggcattagataatcaaaagaaactgagcaagcct cagtcaattaatactgtatctgcacatttacagagtagtgtagttgtttctgattgtaaaaatagtcatataaccccctc agatgttattttccaagcaggattttaattcaaaccataatttaacacctagccaaaaggcagaaattacagaacttt ctactatattagaagaatcaggaagtcagtttgaatttactcagtttagaaaaccaagctacatattgcagaagagt acatttgaagtgcctgaaaaccagatgactatcttaaagaccacttctgaggaatgcagagatgctgatcttcatg tcataatgaatgccccatcgattggtcaggtagacagcagcaagcaatttgaaggtacagttgaaattaaacgg aagtttgctggcctgttgaaaaatgactgtaacaaaagtgcttctggttatttaacagatgaaaatgaagtgggt

FIG. 7B ttaggggcttttattctgctcatggcacaaaactgaatgtttctactgaagctctgcaaaaagctgtgaaactgttta
gtgatattgagaatattagtgaggaaacttctgcagaggtacatccaataagtttatcttcaagtaaatgtcatgatt
ctgttgtttcaatgtttaagatagaaaatcataatgataaaactgtaagtgaaaaaataataaatgccaactgatat
tacaaaataatattgaaatgactactggcactttgttgaagaaattactgaaaattacaagagaaatactgaaaat
gaagataacaaatatactgctgccagtagaaattctcataacttagaatttgatggcagtgattcaagtaaaaatg
atactgtttgtattcataaagatgaaacggacttgctatttactgatcagcacaacatatgtcttaaattatctggcca
gtttatgaaggagggaaacactcagattaaagaagatttgtcagatttaacttttttggaagttgcgaaagctcaa
gaagcatgtcatggtaatacttcaaataaagaacagttaactgctactaaaacggagcaaaatataaaagattttg
agacttctgatacattttttcagactgcaagtgggaaaaatattagtgtcgccaaagagttatttaataaaaattgtaa
atttctttgatcagaaaccagaagaattgcataacttttccttaaattctgaattacattctgacataagaaagaaca
aaatggacattctaagttatgaggaaacagacatagttaaacacaaaatactgaaagaaagtgtcccagttggta
ctggaaatcaactagtgaccttccagggacaacccgaacgtgatgaaaagatcaaagaacctactctgttgggt
tttcatacagctagcggaaaaaaagttaaaattgcaaaggaatctttggacaaagtgaaaaaccttttgatgaaa
aagagcaaggtactagtgaaatcaccagttttagccatcaatgggcaaagaccctaaagtacagagaggcctg
taaagaccttgaattagcatgtgagaccattgagatcacagctgccccaaagtgtaaagaaatgcagaattctct
caataatgataaaaaccttgtttctattgagactgtggtgccacctaagctcttaagtgataatttatgtagacaaac
tgaaaatctcaaaacatcaaaaagtatcttttgaaagttaaagtacatgaaaatgtagaaaaagaaacagcaaaa
agtcctgcaacttgttacacaaatcagtccccttattcagtcattgaaaattcagccttagcttttacacaagttgta
gtagaaaaacttctgtgagtcagacttcattacttgaagcaaaaaaatggcttagagaaggaatatttgatggtca
accagaaagaataaatactgcagattatgtaggaaattatttgtatgaaaataattcaaacagtactatagctgaaa
atgacaaaaatcatctctccgaaaaacaagatacttatttaagtaacagtagcatgtctaacagctattcctaccatt
ctgatgaggtatataatgattcaggatatctctcaaaaaataaacttgattctggtattgagccagtattgaagaat
gttgaagatcaaaaaaacactagtttttccaaagtaatatccaatgtaaaagatgcaaatgcatacccacaaactg
taaatgaagatatttgcgttgaggaacttgtgactagctcttcaccctgcaaaaataaaaatgcagccattaaattg
tccatatctaatagtaataattttgaggtagggccacctgcatttaggatagccagtggtaaaatccgtttgtgttc
acatgaaacaattaaaaaagtgaaagacatatttacagacagtttcagcaaagtaattaaggaaaacaacgaga
ataaatcaaaaatttgccaaacgaaaattatggcaggttgttacgaggcattggatgattcagaggatattcttcat

FIG. 7C aactctctagataatgatgaatgtagcatgcattcacataaggtttttgctgacattcagagtgaagaaattttacaa
cataaccaaaatatgtctggattggagaaagtttctaaaatatcaccttgtgatgttagtttggaaacttcagatata
tgtaaatgtagtatagggaagcttcataagtcagtctcatctgcaaatacttgtgggattttagcacagcaagtg
gaaaatctgtccaggtatcagatgcttcattacaaaacgcaagacaagtgttttctgaaatagaagatagtaccaa
gcaagtcttttccaaagtattgtttaaaagtaacgaacattcagaccagctcacaagagaagaaaatactgctata
cgtactccagaacatttaatatcccaaaaaggcttttcatataatgtggtaaattcatctgctttctctggatttagta
cagcaagtggaaagcaagtttccatttagaaagttccttacacaaagttaagggagtgttagaggaatttgattt
aatcagaactgagcatagtcttcactattcacctacgtctagacaaaatgtatcaaaaatacttcctcgtgttgataa
gagaaacccagagcactgtgtaaactcagaaatggaaaaaacctgcagtaaagaatttaaattatcaaataactt
aaatgttgaaggtggttcttcagaaaataatcactctattaaagtttctccatatctctctcaatttcaacaagacaaa
caacagttggtattaggaaccaaagtctcacttgttgagaacattcatgttttgggaaaagaacaggcttcaccta
aaaacgtaaaaatggaaattggtaaaactgaaacttttttctgatgttcctgtgaaaacaaatatagaagtttgttcta
cttactccaaagattcagaaaactactttgaaacagaagcagtagaaattgctaaagcttttatggaagatgatga
actgacagattctaaactgccaagtcatgccacacattctcttttacatgtcccgaaaatgaggaaatggttttgt
caaattcaagaattggaaaaagaagaggagagccccttatcttagtgggagaaccctcaatcaaaagaaactta
ttaaatgaatttgacaggataatagaaaatcaagaaaaatccttaaaggcttcaaaaagcactccagatggcaca
ataaaagatcgaagattgtttatgcatcatgtttctttagagccgattacctgtgtaccctttcgcacaactaaggaa
cgtcaagagatacagaatccaaattttaccgcacctggtcaagaatttctgtctaaatctcatttgtatgaacatctg
actttggaaaaatcttcaagcaatttagcagtttcaggacatccattttatcaagtttctgctacaagaaatgaaaaa
atgagacacttgattactacaggcagaccaaccaaagtctttgttccaccttttaaaactaaatcacattttcacag
agttgaacagtgtgttaggaatattaacttggaggaaaacagacaaaagcaaaacattgatggacatggctctg
atgatagtaaaaataagattaatgacaatgagattcatcagtttaacaaaaacaactccaatcaagcagcagctgt
aactttcacaaagtgtgaagaagaacctttagatttaattacaagtcttcagaatgccagagatatacaggatatg
cgaattaagaagaaacaaaggcaacgcgtctttccacagccaggcagtctgtatcttgcaaaaacatccactct
gcctcgaatctctctgaaagcagcagtaggaggccaagttccctctgcgtgttctcataaacagctgtatacgta
tggcgtttctaaacattgcataaaaattaacagcaaaaatgcagagtcttttcagtttcacactgaagattatttttgg
taaggaaagtttatggactggaaaaggaatacagttggctgatggtggatggctcatacccctccaatgatggaa

FIG. 7D aggctggaaaagaagaatttlataggggctctgtgtgacactccaggtgtggatccaaagcttatttctagaatttg
ggtttataatcactatagatggatcatatggaaactggcagctatggaatgtgcctttcctaaggaatttgctaata
gatgcctaagcccagaaagggtgcttcttcaactaaaatacagatatgatacggaaattgatagaagcagaaga
tcggctataaaaaagataatggaaagggatgacacagctgcaaaaacacttgttctctgtgtttctgacataattt
cattgagcgcaaatatatctgaaacttctagcaataaaactagtagtgcagatacccaaaaagtggccattattga
acttacagatgggtggtatgctgttaaggcccagttagatcctcccctcttagctgtcttaaagaatggcagactg
acagttggtcagaagattattcttcatggagcagaactggtgggctctcctgatgcctgtacacctcttgaagcc
ccagaatctcttatgttaaagatttctgctaacagtactcggcctgctcgctggtataccaaacttggattctttcct
gaccctagacctttcctctgccttatcatcgctttcagtgatggaggaaatgttggttgtgttgatgtaattattc
aaagagcatacctatacagcggatggagaagacatcatctggattatacatatttcgcaatgaaagagaggaa
gaaaaggaagcagcaaaatatgtggaggcccaacaaaagagactagaagccttattcactaaaattcaggag
gaatttgaagaacatgaagaaaacacaacaaaaccatatttaccatcacgtgcactaacaagacagcaagttcg
tgctttgcaagatggtgcagagctttatgaagcagtgaagaatgcagcagacccagcttaccttgagggttattt
cagtgaagagcagttaagagccttgaataatcacaggcaaatgttgaatgataagaaacaagctcagatccagt
tggaaattaggaaggccatggaatctgctgaacaaaaggaacaaggtttatcaagggatgtcacaaccgtgtg
gaagttgcgtattgtaagctattcaaaaaaagaaaaagattcagttatactgagtatttggcgtccatcatcagatt
tatattctctgttaacagaaggaaagagatacagaatttatcatcttgcaacttcaaaatctaaaagtaaatctgaaa
gagctaacatacagttagcagcgacaaaaaaaactcagtatcaacaactaccggtttcagatgaaattttatttca
gatttaccagccacgggagccccttcacttcagcaaattttagatccagactttcagccatcttgttctgaggtgg
acctaataggatttgtcgtttctgttgtgaaaaaaacaggacttgcccctttcgtctatttgtcagacgaatgttaca
atttactggcaataaagttttggatagaccttaatgaggacattattaagcctcatatgttaattgctgcaagcaacc
tccagtggcgaccagaatccaaatcaggccttcttactttatttgctggagattttctgtgttttctgctagtccaaa
agagggccactttcaagagacattcaacaaaatgaaaaatactgttgagaatattgacatactttgcaatgaagc
agaaaacaagcttatgcatatactgcatgcaaatgatcccaagtggtccaccccaactaaagactgtacttcagg
gccgtacactgctcaaatcattcctggtacaggaaacaagcttctgatgtcttctcctaattgtgagatatattatca
aagtcctttatcactttgtatggccaaaaggaagtctgtttccacacctgtctcagcccagatgacttcaaagtctt
gtaaaggggagaaagagattgatgaccaaaagaactgcaaaaagagaagagccttggatttcttgagtagact gcctttacctccacctgttagtcccatttgtacatttgtttctccggctgcacagaaggcatttcagccaccaagga
gttgtggcaccaaatacgaaacacccataaagaaaaaagaactgaattctcctcagatgactccatttaaaaaatt
caatgaaatttctcttttggaaagtaattcaatagctgacgaagaacttgcattgataaatacccaagctcttttgtct
ggttcaacaggagaaaaacaatttatatctgtcagtgaatccactaggactgctcccaccagttcagaagattatc
tcagactgaaacgacgttgtactacatctctgatcaaagaacaggagagttcccaggccagtacggaagaatgt
gagaaaaataagcaggacacaattacaactaaaaatatatctaagcatttgcaaaggcgacaataaattattga
cgcttaacctttccagtttataagactggaatataatttcaaaccacacattagtacttatgttgccaatgagaaaag
aaattagtttcaaatttacctcagcgtttgtgtatcgggcaaaaatcgtttgcccgattccgtattggtatactttg
cctcagttgcatatcctaaaactaaatgtaatttattaactaatcaagaaaaacatctttggctgagctcggtggctc
atgcctgtaatcccaacactttgagaagctgaggtgggaggagtgcttgaggccaggagttcaagaccagcct
gggcaacatagggagaccccatctttacgaagaaaaaaaaaagggggaaaagaaaatctttaaatctttggat
ttcactacaagtattattttacaagtgaaataaacataccattttcttttagattgtgtcattaaatggaatgaggtctc
ttagtacagttatttgatgcagataattccttttagtttagctactattttaggggattttttttagaggtaactcactat
gaaatagttccccttaatgcaaatatgttggttctgcaatagttccatcctgttcaaaatcggtgaaatgaagagtg
gtgttccttttgagcaattctcatccttaagtcagctgattataagaaaaatagaaccccagtgtaacctaattcctt
ttctattccagtgtgatctctgaaataaattacttcactaaaaattcaaaaacttaatcagaaattcaagtaatttatttt
ttttt
```

FIG. 7F

BRCA2 Protein sequence [SEQ ID NO: 4]

MPIGSKERPTFFEIFKTRCNKADLGPISLNWFEELSSEAPPYNSEPAEE
SEHKNNNYEPNLFKTPQRKPSYNQLASTPIIFKEQGLTLPLYQSPVKE
LDKFKLDLGRNVPNSRHKSLRTVKTKMDQADDVSCPLLNSCLSESPV
VLQCTHVTPQRDKSVVCGSLFHTPKFVKGRQTPKHISESLGAEVDPD
MSWSSSLATPPTLSSTVLIVRNEEASETVFPHDTTANVKSYFSNHDES
LKKNDRFIASVTDSENTNQREAASHGFGKTSGNSFKVNSCKDHIGKS
MPNVLEDEVYETVVDTSEEDSFSLCFSKCRTKNLQKVRTSKTRKKIF
HEANADECEKSKNQVKEKYSFVSEVEPNDTDPLDSNVAHQKPFESGS
DKISKEVVPSLACEWSQLTLSGLNGAQMEKIPLLHISSCDQNISEKDL
LDTENKRKKDFLTSENSLPRISSLPKSEKPLNEETVVNKRDEEQHLES
HTDCILAVKQAISGTSPVASSFQGIKKSIFRIRESPKETFNASFSGHMTD
PNFKKETEASESGLEIHTVCSQKEDSLCPNLIDNGSWPATTTQNSVAL
KNAGLISTLKKKTNKFIYAIHDETFYKGKKIPKDQKSELINCSAQFEA
NAFEAPLTFANADSGLLHSSVKRSCSQNDSEEPTLSLTSSFGTILRKCS
RNETCSNNTVISQDLDYKEAKCNKEKLQLFITPEADSLSCLQEGQCE
NDPKSKKVSDIKEEVLAAACHPVQHSKVEYSDTDFQSQKSLLYDHEN
ASTLILTPTSKDVLSNLVMISRGKESYKMSDKLKGNNYESDVELTKNI
PMEKNQDVCALNENYKNVELLPPEKYMRVASPSRKVQFNQNTNLR
VIQKNQEETTSISKITVNPDSEELFSDNENNFVFQVANERNNLALGNT
KELHETDLTCVNEPIFKNSTMVLYGDTGDKQATQVSIKKDLVYVLA
EENKNSVKQHIKMTLGQDLKSDISLNIDKIPEKNNDYMNKWAGLLG
PISNHSFGGSFRTASNKEIKLSEHNIKKSKMFFKDIEEQYPTSLACVEIV
NTLALDNQKKLSKPQSINTVSAHLQSSVVVSDCKNSHITPQMLFSKQD
FNSNHNLTPSQKAEITELSTILEESGSQFEFTQFRKPSYILQKSTFEVPE

FIG. 8A

NQMTILKTTSEECRDADLHVIMNAPSIGQVDSSKQFEGTVEIKRKFAG
LLKNDCNKSASGYLTDENEVGFRGFYSAHGTKLNVSTEALQKAVKL
FSDIENISEETSAEVHPISLSSSKCHDSVVSMFKIENHNDKTVSEKNNKC
QLILQNNIEMTTGTFVEEITENYKRNTENEDNKYTAASRNSHNLEFD
GSDSSKNDTVCIHKDETDLLFTDQHNICLKLSGQFMKEGNTQIKEDLS
DLTFLEVAKAQEACHGNTSNKEQLTATKTEQNIKDFETSDTFFQTAS
GKNISVAKELFNKIVNFFDQKPEELHNFSLNSELHSDIRKNKMDILSY
EETDIVKHKILKESVPVGTGNQLVTFQGQPERDEKIKEPTLLGFHTAS
GKKVKIAKESLDKVKNLFDEKEQGTSEITSFSHQWAKTLKYREACK
DLELACETIEITAAPKCKEMQNSLNNDKNLVSIETVVPPKLLSDNLC
RQTENLKTSKSIFLKVKVHENVEKETAKSPATCYTNQSPYSVIENSAL
AFYTSCSRKTSVSQTSLLEAKKWLREGIFDGQPERINTADYVGNYLY
ENNSNSTIAENDKNHLSEKQDTYLSNSSMSNSYSYHSDEVYNDSGYLS
KNKLDSGIEPVLKNVEDQKNTSFSKVISNVKDANAYPQTVNEDICVE
ELVTSSSPCKNKNAAIKLSISNSNNFEVGPPAFRIASGKIRLCSHETIKK
VKDIFTDSFSKVIKENNENKSKICQTKIMAGCYEALDDSEDILHNSLD
NDECSMHSHKVFADIQSEEILQHNQNMSGLEKVSKISPCDVSLETSDIC
KCSIGKLHKSVSSANTCGIFSTASGKSVQVSDASLQNARQVFSEIEDST
KQVFSKVLFKSNEHSDQLTREENTAIRTPEHLISQKGFSYNVVNSSAFS
GFSTASGKQVSILESSLHKVKGVLEEFDLIRTEHSLHYSPTSRQNVSKI
LPRVDKRNPEHCVNSEMEKTCSKEFKLSNNLNVEGGSSENNHSIKVSP
YLSQFQQDKQQLVLGTKVSLVENIHVLGKEQASPKNVKMEIGKTET
FSDVPVKTNIEVCSTYSKDSENYFETEAVEIAKAFMEDDELTDSKLPS
HATHSLFTCPENEEMVLSNSRIGKRRGEPLILVGEPSIKRNLLNEFDRI
IENQEKSLKASKSTPDGTIKDRRLFMHHVSLEPITCVPFRTTKERQEIQ
NPNFTAPGQEFLSKSHLYEHLTLEKSSSNLAVSGHPFYQVSATRNEK

FIG. 8B

MRHLITTGRPTKVFVPPFKTKSHFHRVEQCVRNINLEENRQKQNIDG
HGSDDSKNKINDNEIHQFNKNNSNQAAAVTFTKCEEEPLDLITSLQN
ARDIQDMRIKKKQRQRVFPQPGSLYLAKTSTLPRISLKAAVGGQVPS
ACSHKQLYTYGVSKHCIKINSKNAESFQFHTEDYFGKESLWTGKGIQ
LADGGWLIPSNDGKAGKEEFYRALCDTPGVDPKLISRIWVYNHYRW
IIWKLAAMECAFPKEFANRCLSPERVLLQLKYRYDTEIDRSRRSAIKK
IMERDDTAAKTLVLCVSDIISLSANISETSSNKTSSADTQKVAIIELTD
GWYAVKAQLDPPLLAVLKNGRLTVGQKIILHGAELVGSPDACTPLE
APESLMLKISANSTRPARWYTKLGFFPDPRPFPLPLSSLFSDGGNVGC
VDVIIQRAYPIQRMEKTSSGLYIFRNEREEEKEAAKYVEAQQKRLEA
LFTKIQEEFEEHEENTTKPYLPSRALTRQQVRALQDGAELYEAVKN
AADPAYLEGYFSEEQLRALNNHRQMLNDKKQAQIQLEIRKAMESAE
QKEQGLSRDVTTVWKLRIVSYSKKEKDSVILSIWRPSSDLYSLLTEGK
RYRIYHLATSKSKSKSERANIQLAATKKTQYQQLPVSDEILFQIYQPR
EPLHFSKFLDPDFQPSCSEVDLIGFVVSVVKKTGLAPFVYLSDECYNL
LAIKFWIDLNEDIIKPHMLIAASNLQWRPESKSGLLTLFAGDFSVFSAS
PKEGHFQETFNKMKNTVENIDILCNEAENKLMHILHANDPKWSTPT
KDCTSGPYTAQIIPGTGNKLLMSSPNCEIYYQSPLSLCMAKRKSVSTP
VSAQMTSKSCKGEKEIDDQKNCKKRRALDFLSRLPLPPPVSPICTFVS
PAAQKAFQPPRSCGTKYETPIKKKELNSPQMTPFKKFNEISLLESNSIA
DEELALINTQALLSGSTGEKQFISVSESTRTAPTSSEDYLRLKRRCTTS
LIKEQESSQASTEECEKNKQDTITTKKYI

FIG. 8C

THERAPEUTIC METHODS FOR PROSTATE CANCER

GRANT STATEMENT

This invention was made in part from government support under Grant Numbers CA68485 and CA62161 from the National Institute of Health (NIH). The U.S. government has certain rights in the invention.

UTILITY STATEMENT

Both BRCA1 and BRCA2 proteins have been identified as inhibitors of the growth of mammalian prostate cancer cells. Thus, a nucleic acid segment encoding the BRCA1 protein and a nucleic acid segment encoding the BRCA2 protein can be used in gene therapy methods for the treatment of prostate cancer.

The discovery and purification of the BRCA1 and BRCA2 proteins has broad utility. The purified BRCA1 and BRCA2 proteins can be used in treating prostate cancer.

ACTIVITY STATEMENT

The BRCA1 gene product is an inhibitor of the growth and proliferation of mammalian prostate cancer cells. The BRCA1 gene product is a secreted protein, thus indicating that it acts on a receptor to produce this activity.

The BRCA2 gene product is an inhibitor of the growth and proliferation of mammalian prostate cancer cells. The BRCA2 protein is a secreted protein, thus indicating that it acts on a receptor to produce this activity.

TECHNICAL FIELD

The present invention relates to a therapy for prostate cancer; and more particularly to a gene therapy method for prostate cancer using the BRCA gene family, and still more particularly, using the BRCA1 gene.

The publications and other materials used herein to illuminate the background of the invention, and in particular cases, to provide additional details respecting the practice, are incorporated herein by reference, and for convenience, are referenced by author and date in the following text, and respectively group in the appended list of references.

Table of Abbreviations

| | |
|---|---|
| PPC-1 | A prostate cancer cell line from primary tumor |
| DU145 | A prostate cancer cell line from brain metastasis |
| LNCaP | A prostate cancer cell line from lymph node metastasis |
| PC3 | A prostate cancer cell line from primary tumor |
| TSU | A prostate cancer cell line of unknown origin |
| D17S855 | A prostate cancer cell genotype, indicating number of alleles at markers flanking BRCA1 |
| D17S1322 | A prostate cancer cell genotype, indicating number of alleles at markers flanking BRCA1 |
| D17S1327 | A prostate cancer cell genotype, indicating number of alleles at markers flanking BRCA1 |
| D17S1326 | A prostate cancer cell genotype, indicating number of alleles at markers flanking BRCA1 |
| D17S1325 | A prostate cancer cell genotype, indicating number of alleles at markers flanking BRCA1 |
| LXSN | A retroviral vector derived from a mouse retrovirus |
| Cys61Gly | A mutation in the BRCA1 protein at amino acid 61 wherein a cysteine is substituted for a glycine |
| 340stop | A mutant BRCA1 protein wherein a stop codon is inserted in place of the codon coding for amino acid 340 |
| del(343-1081) | A BRCA1 mutant protein wherein amino acids 343-1081 have been deleted |
| 1835stop | A mutant BRCA1 protein wherein a stop codon has been inserted in place of the codon encoding the amino at position 1835 |
| AIM V | An animal serum free growth media for retroviral vectors |
| PSA | Prostate specific antigen |
| LTR regulated | gene expression controlled by the LXSN retroviral promoter |

BACKGROUND ART

A staggering estimated 317,000 new cases of prostate cancer will be diagnosed and over 45,000 prostate cancer deaths will occur this year in the United States making prostate cancer the most frequently diagnosed and second leading cause of cancer mortality in men in the United States. Deaths from prostate cancer in the United States are increasing every year by 2%–3% because fewer men are dying from cardiovascular disease. (Walsh, 1994) Unfortunately, the age-specific mortality rate for prostate cancer continues to rise in spite of earlier detection by serum PSA or current prostate cancer treatment modalities. Moreover, at the time of diagnosis the majority of men will have prostate cancer at a stage for which there is no cure and the prognosis is dismal.

African-American men have the highest prostate cancer mortality rates of any population in the world, twice that of white men 65 years or older. Furthermore, survival rates in the United States for all stages of prostate cancer diagnosed between 1983 and 1990 was 81.3% for Whites, but only 66.4% for Blacks. Of all prostate cancer deaths in 1991, Blacks accounted for 15.8%, Hispanics for 2.5%, and American Indians, Chinese, and Japanese for less than 1%. The general United States population is 75% White, 12% African-American, 8% Hispanic, and 3% Asian.

The standard method of treatment for the past 50 years has been castration, surgical or chemical, but the prostate cancer has eventually become androgen-independent, resumed growth, and killed the patient. Clearly, better androgen blockade is not the answer for treating prostate cancer. Rather, treatment efforts should focus on modifying the mutations that lead to prostate oncogenesis. Although some genetic markers can at least partially predict patients who are likely to develop metastatic disease, it is still impossible to predict absolutely patient prognosis and response to therapy. (Walsh, 1994; Carter et al., 1990) Thus, even well implemented early detection programs may not completely eradicate the eventual development of metastasis in some patients.

The molecular biology of prostate cancer is poorly understood. Attempts to develop animal models of prostate cancer with transgenic mice have been less successful than for animal models of other cancers such as breast cancer. (Mulders et al., 1990; Oesterling, 1991; Jurincic et al., 1990; Hamdy et al., 1992; Pang et al., 1995; Matuo et al., 1989; Dodd et al., 1983; Greenberg et al., 1994; Greenberg et al, 1995; Tutrone et al., 1993; Matsui et al., 1990; Halter et al., 1992; Cato et al., 1989; Choi et al., 1987; Tutrone et al., 1993; Matsui et al., 1990; Halter et al., 1992; Muller et al., 1990) This has presumably happened because little is known about prostate-specific promoters and because study of oncogenes and tumor suppressor genes have yielded few clear-cut candidate genes for prostate cancer.

Inherited mutations in BRCA1, (Hall et al., 1990; Miki et al., 1994) confer lifetime risk of breast cancer greater than 80% and increased risk of ovarian cancer. (Newman et al., 1988; Ford et al., 1994). Multiple lines of evidence suggest that BRCA1 is a tumor suppressor for the following six reasons:

(1) Most (87%) inherited mutations truncate the BRCA1 protein, leading to loss of BRCA1 function. (Breast Cancer Information Core, 1996)

(2) The wild-type allele is lost from >90% of breast and ovarian tumors from patients with inherited BRCA1 mutations. (Friedman et al., 1994; Neuhausen et al., 1994; Smith et al., 1992)

(3) BRCA1 expression is reduced in breast and ovarian tumors from patients not selected for family history. (Thompson et al., 1995) In such tumors, somatic inactivation of BRCA1 may occur through mechanisms such as large deletions or epigenetic silencing of BRCA1 expression, rather than point mutation. (Futreal et al., 1994; Cropp et al., 1993; Saito et al., 1993; Cliby et al., 1993; Russell et al., 1990; Takahashi et al., 1995; Yang-Feng et al., 1993)

(4) Inhibition of BRCA1 expression with antisense oligonucleotides leads to accelerated growth of normal and malignant mammary epithelial cells. (Thompson et al., 1995)

(5) Overexpression of BRCA1 inhibits growth of breast and ovarian cancer cell lines derived from patients not selected for family history. (Holt et al., 1996)

(6) Transfection or infection of MCF-7 breast cancer cells with the wild type BRCA1 gene inhibits tumor development and suppresses growth of established tumors in nude mice. (Holt et al., 1996) The biochemical mechanism responsible for growth inhibition and tumor suppression by BRCA1 involves secretion, since BRCA1 has sequence homology and functional analogy to the granin protein family. Wild type BRCA1 is localized to the Golgi; (Jensen et al., 1996) and wild-type BRCA1 is also present in the nucleus, although reports differ in the relative amounts of nuclear versus cytoplasmic protein. (Chen et al., 1995)

There has been no affirmative suggestion of a treatment of prostatic cancer comprising a therapeutic application of the BRCA gene family, and particularly comprising a therapeutic application involving BRCA1. This is true despite certain epidemiological, genetic, and biological observations in the art, including the following four observations: (1) Breast and prostatic cancer, and ovarian and prostatic cancer, are associated in families, (Jishi et al., 1995; Anderson et al., 1993; Sellers et al., 1994; Tulinium et al., 1994) although the association is not observed in families in which index cases were patients with prostatic cancer (rather than breast or ovarian cancer). (Isaacs et al., 1995) (2) Inherited mutations in BRCA1 have been observed in prostatic cancer patients, both in families at high risk of breast and ovarian cancer (Ford et al., 1994; Friedman et al., 1994; Struewing et al., 1995) and in isolated patients. (Langston et al., 1996) (3) Prostatic tumors are frequently hemizygous for markers in or near BRCA1. (Williams et al., 1996; Gao et al., 1995; Brothman et al., 1995; Gao et al., 1995) (4) The malignant phenotype of the human prostatic cancer cell line PPC-1 was suppressed by transfer of an -30 Mb portion of chromosome 17 containing BRCA1. (Murakami et al., 1995). Additionally, although the 30 Mb portion of chromosome 17 contained BRCA1, it also contained numerous other genes and included a region proposed to contain a different tumor suppressor gene.

Given the prevalence of prostate cancer, what is needed, then, is an effective therapy for prostate cancer that addresses the disease at a molecular genetic level. Despite attempts to characterize the molecular biology of prostate cancer, such a therapy is lacking in the prior art.

DISCLOSURE OF THE INVENTION

A method to suppress the growth of a prostate tumor in a mammal is disclosed. The method comprises introducing to said tumor a vector comprising a nucleic acid sequence encoding a BRCA family gene product operatively linked to a promoter, wherein the production of the BRCA family gene product results in a decrease in the growth rate of the tumor. The vector can comprise a plasmid vector or a viral vector. Preferably, the vector comprises a retroviral vector. The prostate cancer can comprise gene-linked hereditary prostate cancer or sporadic prostate cancer.

A method to suppress the growth of a prostate tumor in a mammal wherein the method comprises introducing to said tumor a liposome complexed to a nucleic acid encoding a prostate tumor suppressing polypeptide operatively linked to a promoter, the nucleic acid encoding a BRCA family gene product, wherein production of the prostate tumor suppressing polypeptide results in a decrease of the growth rate of the tumor is also described.

The BRCA family gene product can comprise a BRCA1 targeted growth inhibitor agent or a BRCA2 targeted growth inhibitor agent, as defined herein. The BRCA family gene product can also comprise the BRCA1 gene product or the BRCA2 gene product, and nucleic acids encoding such products, as defined herein.

Therefore, an aspect of this invention concerns purified and isolated BRCA1 and BRCA2 gene products; and biologically functional and structural equivalents of each.

Another aspect of this invention is that the BRCA1 and BRCA2 gene products are tumor suppressor/growth inhibitors that exhibit tumor suppression/growth inhibition activity in prostate cancer.

Yet another aspect of this invention is that the BRCA1 and BRCA2 gene products are secreted, and thus, act on a receptor to impart their activity.

Important aspects of the present invention concern isolated DNA segments and recombinant vectors encoding the BRCA1 and the BRCA2 gene products, and the creation and use of recombinant host cells, through the application of recombinant DNA technology, which express the BRCA1 and BRCA2 gene products.

Introduction of Gene Products

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the tumor-suppressing gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if such a site was not contained within the original inserted DNA. Typically, these poly A addition sites are placed about 30 to 2000 nucleotides "downstream" of the coding sequence at a position prior to transcription termination.

While use of the control sequences of the specific gene (e.g., the BRCA1 promoter for BRCA1 and the BRCA2 promoter for BRCA2) will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

For introduction of a BRCA family gene, such as BRCA1 and BRCA2, it is proposed that one will desire preferably to employ a vector construct that will deliver the desired gene to the affected cells. This will, of course, generally require that the construct be delivered to the targeted tumor cells, for example, prostate tumor cells. It is proposed that this may be achieved most preferably by introduction of the desired gene through the use of a viral vector to carry either BRCA family sequences efficiently to infect the tumor, or pretumorous tissue. These vectors will preferably be an adenoviral, a retroviral, a vaccinia viral vector or adeno-associated virus. These vectors are preferred because they have been successfully used to deliver desired sequences to cells and tend to have a high infection efficiency. An example of a particularly preferred vector is the LXSN retroviral vector described herein.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bg1 I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) sources, or may be provided by the host cell chromosomal replication mechanism. If the vector is integrated into the host cell chromosome, the latter is often sufficient.

Definitions and Techniques Affecting Gene Products and Genes

The present invention concerns DNA segments, isolatable from mammalian tissue, which are free from genomic DNA and which are capable of conferring tumor suppressor/ growth inhibitor activity in a recombinant host cell when incorporated into the recombinant host cell. As used herein, the term "mammalian tissue" refers to normal and cancerous mammalian breast, ovarian or prostate tissues, as exemplified by, but not limited to, HMEC, MCF-7 or PPC-1 cell lines. DNA segments capable of conferring tumor suppressor activity may encode complete BRCA1 and BRCA2 gene products, cleavage products and biologically actively functional domains thereof.

The term "BRCA family", as used in the specification and in the claims, is contemplated to include the BRCA granins described herein, including BRCA1 and BRCA2 genes and gene products. The BRCA family is characterized by the tumor suppressor activity of the gene product and the granin box consensus sequence shown in FIG. 5.

The terms "BRCA1 gene product" and "BRCA1" or "BRCA2 gene product" and "BRCA2" as used in the specification and in the claims refer to proteins having amino acid sequences which are substantially identical to the native BRCA1 or BRCA2 amino acid sequences and which are biologically active in that they are capable of suppressing tumor growth or cross-reacting with an anti-BRCA1 or an anti-BRCA2 antibody raised against BRCA1 or BRCA2. Such sequences are disclosed, for example, by Miki et al. 1994 and Wooster et al. 1995. The terms "BRCA1 gene product" and "BRCA2 gene product" also include analogs of BRCA1 and BRCA2 molecules which exhibit at least some biological activity in common with native BRCA1 or BRCA2. Furthermore, those skilled in the art of mutagenesis will appreciate that other analogs, as yet undisclosed or undiscovered, may be used to construct BRCA1 or BRCA2 analogs. There is no need for a "BRCA1 gene product" or "BRCA1", or a "BRCA2 gene product" or "BRCA2" to comprise all, or substantially all, of the amino acid sequence of the native BRCA1 or BRCA2 genes. Shorter or longer sequences are anticipated to be of use in the invention.

The terms "BRCA1 gene" and "BRCA2 gene" refer to any DNA sequence that is substantially identical to a DNA sequence encoding a BRCA1 gene product or a BRCA2 gene product as defined above. The terms also refer to RNA, or antisense sequences, compatible with such DNA sequences. A "BRCA1 gene" or a "BRCA2 gene" may also comprise any combination of associated control sequences.

The term "substantially identical", when used to define either a BRCA1 or a BRCA2 amino acid sequence, or a BRCA1 or a BRCA2 nucleic acid sequence, means that a particular sequence, for example, a mutant sequence, varies from the sequence of natural BRCA1 or BRCA2 by one or more deletions, substitutions, or additions, the net effect of which is to retain at least some of biological activity of the BRCA1 or the BRCA2 protein. Alternatively, DNA analog sequences are "substantially identical" to specific DNA sequences disclosed herein if: (a) the DNA analog sequence is derived from coding regions of the natural BRCA1 or BRCA2 gene; or (b) the DNA analog sequence is capable of hybridization of DNA sequences of (a) under moderately stringent conditions and which encode biologically active BRCA1 or BRCA2; or (c) the DNA sequences are degenerative as a result of the genetic code to the DNA analog sequences defined in (a) and/or (b). Substantially identical analog proteins will be greater than about 80% to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences.

The term "BRCA1 targeted growth inhibitor agent", as used in the specification and in the claims, is defined as the BRCA1 gene product characterized herein, whether isolated and purified directly from a natural source such as mammalian prostate, ovarian or breast cells, or produced using recombinant methods. The term "BRCA1 targeted growth inhibitor agent" also refers to a targeted growth inhibitor having the biological activity of tumor suppression and/or growth inhibition activity in mammalian prostate cancer cells. The term "BRCA1 targeted growth inhibitor agent"

also refers to a targeted growth inhibitor agent which binds the BRCA1 receptor. The term "BRCA1 targeted growth inhibitor agent" also includes biologically functional equivalents of the BRCA1 gene product characterized herein, the term biologically functional equivalent defined herein to include, among others, proteins and protein fragments in which biologically functionally equivalent amino acids have been inserted, and peptidomimetics.

The term "BRCA2 targeted growth inhibitor agent" is used herein as "BRCA1 targeted growth inhibitor agent" above but applies to the BRCA2 gene product.

Percent Similarity

Percent similarity may be determined, for example, by comparing sequence information using the GAP computer program, available from the University of Wisconsin Geneticist Computer Group. The GAP program utilizes the alignment method of Needleman et al. 1970, as revised by Smith et al. 1981. Briefly, the GAP program defines similarity as the number of aligned symbols (i.e. nucleotides or amino acids) which are similar, divided by the total number of symbols in the shorter of the two sequences. The preferred default parameters for the GAP program include: (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

Nucleic Acid Sequences

In certain embodiments, the invention concerns the use of tumor suppressor genes and gene products, such as the BRCA family gene products, including BRCA1 and BRCA2, that include within their respective sequences a sequence which is essentially that of a BRCA family gene, including the known BRCA1 and BRCA2 genes, or the corresponding proteins. The term "a sequence essentially as that of a BRCA family gene or gene product, including BRCA1 or BRCA2", means that the sequence substantially corresponds to a portion of a BRCA family gene or gene product, including BRCA1 or BRCA2, and has relatively few bases or amino acids (whether DNA or protein) which are not identical to those of a BRCA family gene or gene product, including BRCA1 and BRCA2 (a biologically functional equivalent of, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of a BRCA family gene or gene product, including BRCA1 and BRCA2, will be sequences which are "essentially the same".

BRCA1 and BRCA2 genes which have functionally equivalent codons are also covered by the invention. The term "functionally equivalent codon" is used herein to refer to codons that encode the same amino acid, such as the six codons for arginine or serine, and also to refer to codons that encode biologically equivalent amino acids (see FIG. 2).

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are " complementary" are those which are base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. (See, e.g., Wetmur & Davidson, 1968; Kanehisa, 1984).

Probe sequences may also hybridize specifically to duplex DNA under certain conditions to form triplex or other higher order DNA complexes. The preparation of such probes and suitable hybridization conditions are well known in the art.

As used herein, the term "DNA segment" refers to a DNA molecule which has been isolated free of total genomic DNA of a particular species. Furthermore, a DNA segment encoding a BRCA1 gene product or encoding a BRCA2 gene product refers to a DNA segment which contains BRCA1 coding sequences or contains BRCA2 coding sequences, yet is isolated away from, or purified free from, total genomic DNA of Homo sapiens. Included within the term "DNA segment" are DNA segments and smaller fragments of such segments, and also recombinant vectors, including, for example, plasmids, cosmids, phages, viruses, and the like.

Similarly, a DNA segment comprising an isolated or purified BRCA1 gene or BRCA2 gene refers to a DNA segment including BRCA1 coding sequences substantially away from other naturally occurring genes or protein encoding sequences or including BRCA2 coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the BRCA1 gene or the BRCA2 gene, forms the significant part of the coding region of the DNA segment, and that the DNA segment does not contain large portions of naturally-occurring coding DNA, such as large chromosomal fragments or other functional genes or CDNA coding regions. of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a BRCA1 protein that includes within its amino acid sequence the amino acid sequence of SEQ ID NO:2. In other particular embodiments, the invention concerns isolated DNA segments and recombinant vectors incorporating DNA sequences which encode a protein that includes within its amino acid sequence the amino acid sequence of the BRCA1 protein corresponding to human prostate tissue.

In particular embodiments, the invention concerns isolated DNA segments and recombinant vectors incorporating DNA sequences which encode a BRCA2 protein that includes within its amino acid sequence the amino acid sequence of SEQ ID NO:4. In other particular embodiments, the invention concerns isolated DNA segments and recombinant vectors incorporating DNA sequences which encode a protein that includes within its amino acid sequence the amino acid sequence of the BRCA2 protein corresponding to human prostate tissue.

It will also be understood that this invention is not limited to the particular nucleic acid and amino acid sequences of SEQ ID NOS:1, 2, 3 and 4. Recombinant vectors and isolated DNA segments may therefore variously include the BRCA1 and BRCA2 encoding regions themselves, include coding regions bearing selected alterations or modifications in the basic coding region, or include encoded larger polypeptides which nevertheless include BRCA2 or BRCA2 encoding regions or may encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in SEQ ID NO:2 or SEQ ID NO:4, and methods of treating prostate cancer using these DNA segments. Naturally, where the DNA segment or vector encodes a full length BRCA1 or BRCA2 gene product, the most preferred sequences are those which are essentially as set forth in SEQ ID NO:1 and SEQ ID NO:3 and which encode a protein that exhibits tumor suppressor activity in human prostate cancer cells, as may be determined by the prostate cancer cell growth inhibition experiments, as disclosed herein.

The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein. Accordingly, sequences, which have between about 70% and about 80%; or more preferably, between about 81% and about 90%; or even more preferably, between about 91% and about 99%; of amino acids which are identical or functionally equivalent to the amino acids of SEQ ID NO:2, will be sequences which are "essentially as set forth in SEQ ID NO:2". The term "a sequence essentially set forth in SEQ ID NO:4" has a similar meaning.

In particular embodiments, the invention concerns gene therapy methods that use isolated DNA segments and recombinant vectors incorporating DNA sequences which encode a protein that includes within its amino acid sequence an amino acid sequence in accordance with SEQ ID NO:2 or in accordance with SEQ ID NO:4, SEQ ID NO:2 and SEQ ID NO:4 derived from prostate tissue from Homo sapiens. In other particular embodiments, the invention concerns isolated DNA sequences and recombinant DNA vectors incorporating DNA sequences which encode a protein that includes within its amino acid sequence the amino acid sequence of the BRCA1 protein from human prostate tissue, or which encode a protein that includes within its amino acid sequence the amino acid sequence of the BRCA2 protein from human prostate tissue.

In certain other embodiments, the invention concerns isolated DNA segments and recombinant vectors that include within their sequence a nucleic acid sequence essentially as set forth in SEQ ID NO:1, or a nucleic acid sequence essentially as set forth in SEQ ID NO:3, and methods of treating prostate cancer using these sequences. The term "essentially as set forth in SEQ ID NO:1" is used in the same sense as described above and means that the nucleic acid sequence substantially corresponds to a portion of SEQ ID NO:1, respectively, and has relatively few codons which are not identical, or functionally equivalent, to the codons of SEQ ID NO:1, respectively. Again, DNA segments which encode gene products exhibiting tumor suppression activity of the BRCA1 and BRCA2 gene products will be most preferred. The term "functionally equivalent codon" is used herein to refer to codons that encode the same amino acid, such as the six codons for arginine or serine, and also to refer to codons that encode biologically equivalent amino acids (see FIG. 2). The term "essentially as set forth in SEQ ID NO:3" has a similar meaning.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1 or SEQ ID NO:3, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

The DNA segments of the present invention encompass biologically functional equivalent BRCA1 and BRCA2 proteins and peptides. Such sequences may rise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test BRCA1 and BRCA2 mutants in order to examine tumor suppression activity at the molecular level.

If desired, one may also prepare fusion proteins and peptides, e.g., where the BRCA1 or BRCA2 coding regions are aligned within the same expression unit with other proteins or peptides having desired functions, such as for purification or immunodetection purposes (e.g., proteins which may be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with the BRCA1 or BRCA2 gene(s), e.g., in prostate cancer cells, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a BRCA1 or BRCA2 gene in its natural environment. Such promoters may include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., 1989, specifically incorporated herein by reference. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the LXSN promoter, which is more fully described below.

As mentioned above, in connection with expression embodiments to prepare recombinant BRCA1 and BRCA2 proteins and peptides, it is contemplated that longer DNA segments will most often be used, with DNA segments encoding the entire BRCA1 or BRCA2 protein, functional domains or cleavage products thereof, being most preferred. However, it will be appreciated that the use of shorter DNA segments to direct the expression of BRCA1 and BRCA2 peptides or epitopic core regions, such as may be used to generate anti-BRCA1 or anti-BRCA2 antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins may have a minimum coding length on the order of about 5,600 nucleotides for a protein in accordance with SEQ ID NO:2 or a minimum coding length on the order of about 10,300 nucleotides for a protein in accordance with SEQ ID NO:4.

Naturally, the present invention also encompasses DNA segments which are complementary, or essentially complementary, to the sequence set forth in SEQ ID NO:1 or the sequence set forth in SEQ ID NO:3. The terms "complementary" and "essentially complementary" are defined above. Excepting intronic or flanking regions, and allowing for the degeneracy of the genetic code, sequences which have between about 70% and about 80%; or more preferably, between about 81% and about 90%; or even more preferably, between about 91% and about 99%; of nucleotides which are identical or functionally equivalent (i.e. encoding the same amino acid) of nucleotides of SEQ ID NO:1 or to the nucleotides of SEQ ID NO:3, will be respectively sequences which are "essentially as set forth in SEQ ID NO:1" and will be sequences which are "essentially as set forth in SEQ ID NO:3". Sequences which are essentially the same as those set forth in SEQ ID NO:1 or as those set forth in SEQ ID NO:3 may also be functionally defined as sequences which are capable of hybridizing to a nucleic acid segment containing the complement of SEQ ID NO:1 or to a nucleic acid segment containing the complement of SEQ ID NO:3 under relatively stringent conditions. Suitable relatively stringent hybridization conditions are described herein and will be well known to those of skill in the art (Sambrook et al., 1989).

Biological Functional Equivalent Proteins and Peptides

Modification and changes may be made in the structure of the BRCA1 protein and the BRCA2 protein, or in cleavage products of these proteins, and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules or receptors, specifically the BRCA1 or BRCA2 receptor. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of the BRCA1 and BRCA2 proteins or peptides (or underlying DNA) without appreciable loss of their biological utility or activity.

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate=Glu (E); Glutamine=Gln (Q); Glycine=Gly (G); Histidine=His (H); Isoleucine=Ile (I); Leucine=Leu (L); Lysine=Lys (K); Methionine=Met (M); Phenylalanine=Phe (F); Proline=Pro (P); Serine=Ser (S); Threonine=Thr (T); Tryptophan=Trp (W); Tyrosine=Tyr (Y); Valine=Val (V).

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distance proteins/peptides with different substitutions may easily be made and used in accordance with this invention.

It is also well understood that where certain residues are shown to be particularly important to the biological or structural properties of a protein or peptide, e.g., residues in active sites, such residues may not generally be exchanged. This is the case in the present invention where an exchange in the granin box domain may alter the fact that the BRCA1 and BRCA2 proteins are secreted.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine, and histidine are all positively charged residues; that alanine, glycine and serine are all a similar size; and that phenylalanine, tryptophan and tyrosine all have a generally similar shape. Therefore, based upon these considerations, arginine, lysine and histidine are defined herein as biologically functional equivalents of each other; alanine, glycine and serine are defined herein as biologically functional equivalents of each other; and phenylalanine, tryptophan and tyrosine are defined herein as biologically functional equivalents of each other.

In making such changes, the hydropathic index of amino acids may be considered. Each amino acid has been assigned a hydropathic index on the basis of its hydrophobicity and charge characteristics. These indices are: isoleucine (+4.5); valine (+4.2); leucine (+3.8); phenylalanine (+2.8); cystein/ cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference) . It is known that certain amino acids may be substituted for other amino acids having a similar hydropathic index or score and still retain a similar biological activity. In making changes based upon the hydropathic index, the substitution of amino acids whose hydropathic indices are within ±1 are particularly preferred, and those with ±2 are more particularly preferred, those which are within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments. U.S. Pat. No. 4,554, 101, incorporated herein by reference, states that the greatest local average hydrophilicity of a protein, as governed by the hydrophilicity of its adjacent amino acids, correlates with its immunogenicity and antigenicity, i.e., with a biological property of the protein. It is understood that an amino acid can be substituted for another having a similar hydrophilicity value and still obtain a biologically equivalent, and in particular, an immunologically equivalent protein.

As detailed in U.S. Pat. No. 4,554,101, the following hydrophilicity values have been assigned to amino acid residues: arginine (+3.0); lysine (+3.0); aspartate (+3.0 ±1); glutamate (+3.0 ±1); serine (+0.3); asparagine (+0.2); glutamine (+0.2); glycine (0); threonine (−0.4); proline (−0.5 ±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids that shows hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

While discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

Sequence Modification Techniques

Modifications to the BRCA1 and BRCA2 peptides may be carried out using techniques such as site directed mutagenesis. Site-specific mutagenesis is a technique useful in the preparation of individual peptides, or biological functional equivalent proteins or peptides, through specific mutagenesis of the underlying DNA. The technique further provides a ready ability to prepare and to test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al. 1983). As will be appreciated, the technique typically employs a phage vector which exists in both a single stranded and double stranded form. Typical vectors useful in site-directed mutagenesis include vectors such as the M13 phage (Messing et al., 1981). These phage vectors are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single stranded vector or melting apart the two strands of a double stranded vector which includes within its sequence a DNA sequence which encodes a BRCA family gene, including BRCA1 and/or BRCA2. An oligonucleotide primer bearing the desired mutated sequence is prepared, generally synthetically, for example by the method of Crea et al. (1978). This primer is then annealed with the single stranded vector, and subjected to DNA polymerizing enzymes such as *E. Coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. Coli* cells, and clones are selected which include recombinant vectors bearing the mutated sequence arrangement.

The preparation of sequence variants of the selected gene using site-directed mutagenesis is provided as a means of producing potentially useful BRCA1, BRCA2 or other BRCA family species and is not meant to be limiting as there are other ways in which sequence variants of these peptides may be obtained. For example, recombinant vectors encoding the desired genes may be treated with mutagenic agents to obtain sequence variants (see, e.g., a method described by Eichenlab, 1979) for the mutagenesis of plasmid DNA using hydroxylamine.

Other Structural Equivalents

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of this invention.

Accordingly, it is an object of this invention to provide a gene therapy for prostate cancer which includes the BRCA gene family, and particularly includes the BRCA1 gene.

It is a further object of this invention to provide a therapy for prostate cancer that addresses the disease at a molecular genetic level.

It is a further object of this invention to provide a method of preventing prostate cancer comprising prophylactic gene therapy using the BRCA gene family, and particularly the BRCA1 gene.

Some of the objects of the invention having been stated hereinabove, other objects will become evident as the description proceeds, when taken in connection with the accompanying Laboratory Examples and drawings as best described hereinbelow.

BRIEF DESCRIPTION OF THE DRAWINGS

FIG. 2 is a table of the genetic code.

FIG. 4 is a diagram showing sequence alignment of the granin region of selected granin family members compared with BRCA1.

FIG. 5 is a diagram showing sequence alignment of the granin region of selected granin family members compared with BRCA1 and BRCA2.

FIGS. 6A–6D depict the sequence of the BRCA1 gene [SEQ ID NO:1].

FIGS. 7A–7F depict the sequence of the BRCA2 gene [SEQ ID NO:3].

FIGS. 8A–8C depict the sequence of the BRCA2 protein [SEQ ID NO:4].

DETAILED DESCRIPTION OF THE INVENTION

Figure 1A:
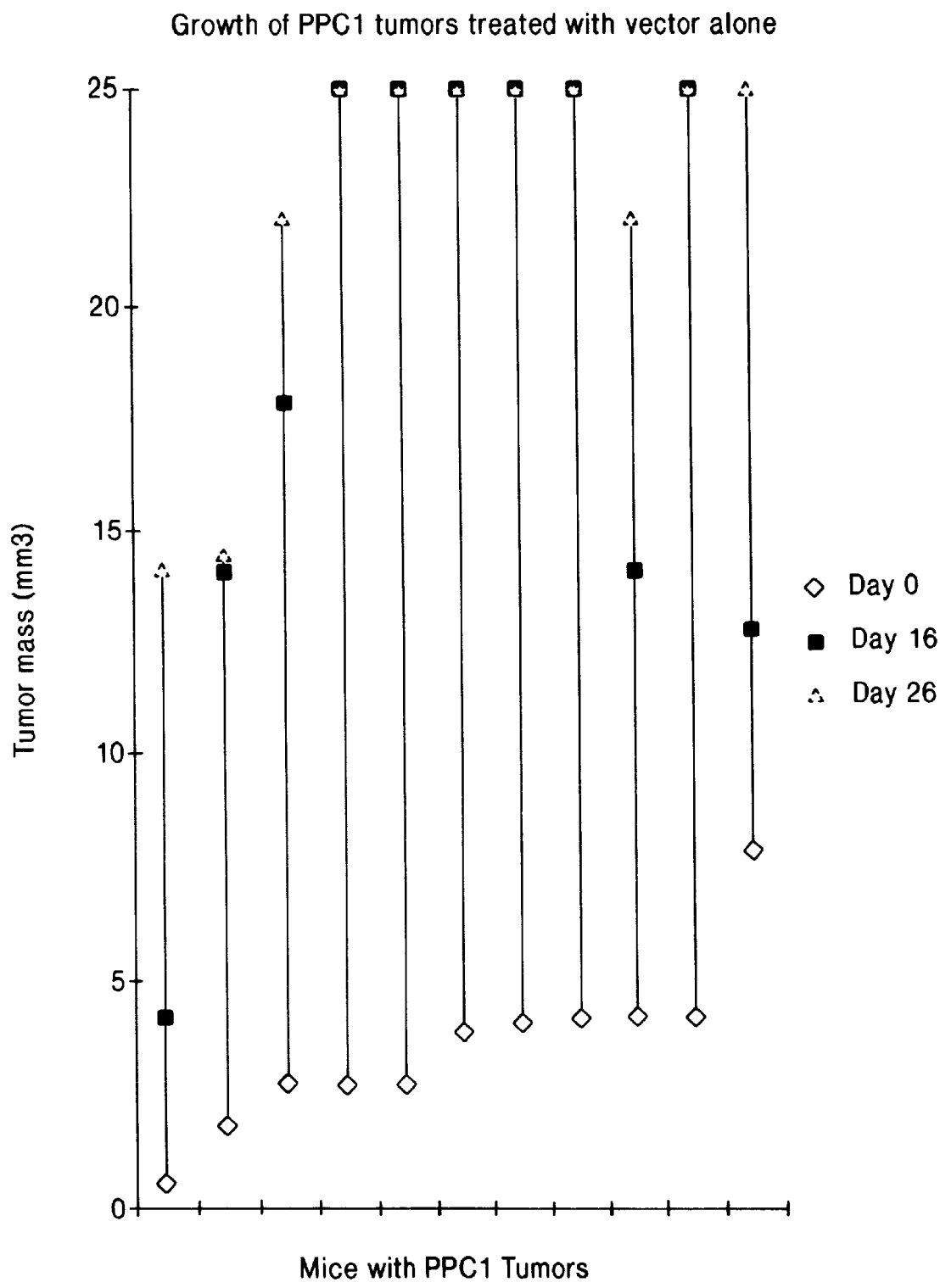
FIG. 1A presents a graphical depiction of the growth of PPC-1 tumors treated with the vector alone.
Figure 1B:
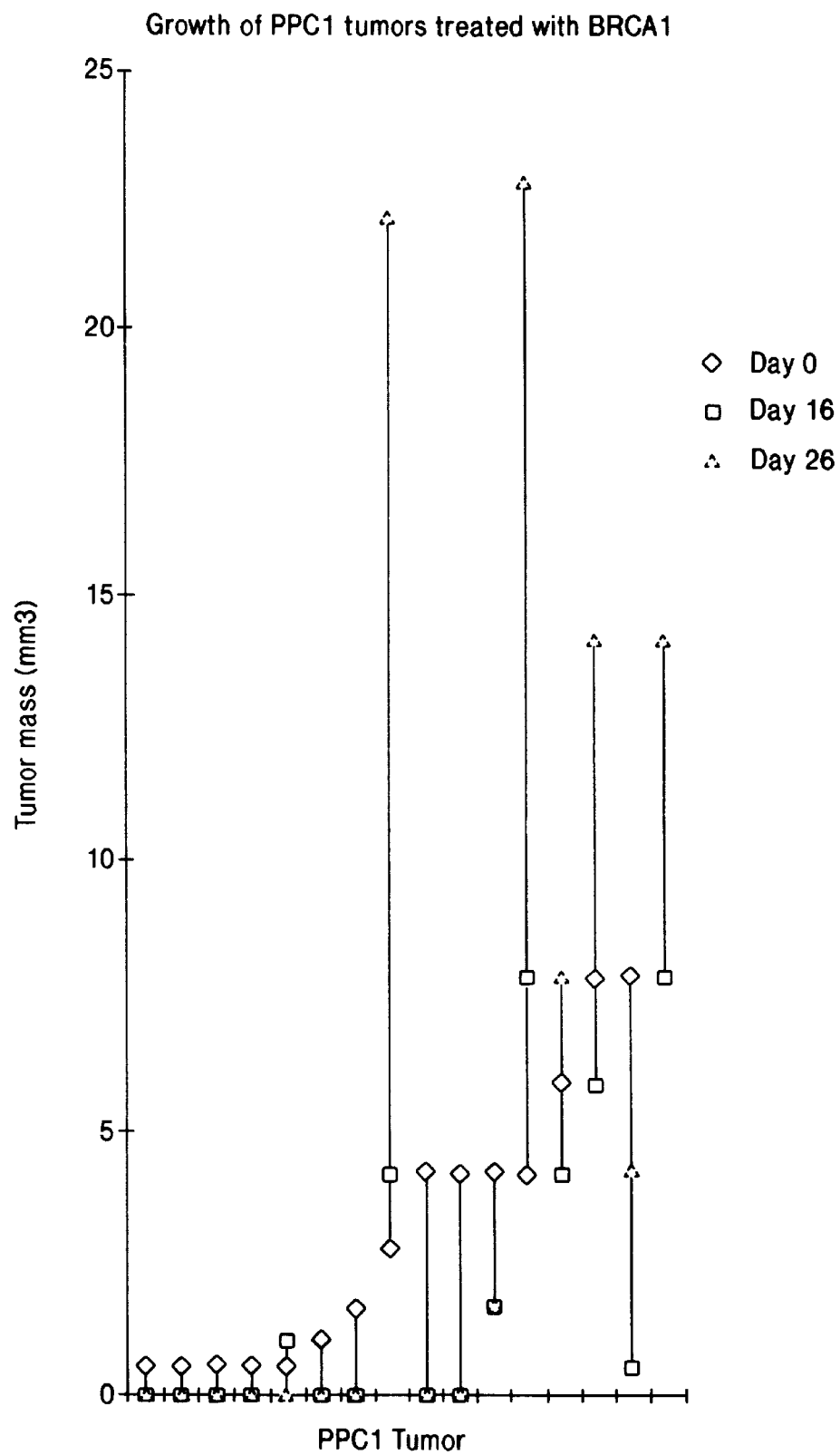
FIG. 1B presents a graphical depiction of PPC-1 tumors treated with BRCA1. In both FIGS. 1A and 1B the diamond shapes represent day 0, the solid square shapes represent day 16, and the triangle shapes represent day 26.

For the purposes of the subsequent description, the following definitions will be used:

Nucleic acid sequences which are "complementary" are those which are capable of base-pairing according to standard Watson-Crick complementarity rules. That is, that the larger purines will always base pair with the smaller pyrimidines to form only combinations of Guanine paired with Cytosine (G:C) and Adenine paired with either Thymine (A:T) in the case of DNA, or Adenine paired with Uracil (A:U) in the case of RNA.

"Hybridization techniques" refer to molecular biological techniques which involve the binding or hybridization of a probe to complementary sequences in a polynucleotide. Included among these techniques are northern blot analysis, southern blot analysis, nuclease protection assay, etc.

"Hybridization" and "binding" in the context of probes and denatured DNA are used interchangeably. Probes which are hybridized or bound to denatured DNA are aggregated to complementary sequences in the polynucleotide. Whether or not a particular probe remains aggregated with the polynucleotide depends on the degree of complementarity, the length of the probe, and the stringency of the binding conditions. The higher the stringency, the higher must be the degree of complementarity and/or the longer the probe.

"Probe" refers to an oligonucleotide or short fragment of DNA designed to be sufficiently complementary to a sequence in a denatured nucleic acid to be probed and to be bound under selected stringency conditions.

"Label" refers to a modification to the probe nucleic acid that enables the experimenter to identify the labeled nucleic acid in the presence of unlabeled nucleic acid. Most commonly, this is the replacement of one or more atoms with radioactive isotopes. However, other labels include covalently attached chromophores, fluorescent moieties, enzymes, antigens, groups with specific reactivity, chemiluminescent moieties, and electrochemically detectable moieties, etc.

"Tissuemizer" describes a tissue homogenization probe.

"PCR technique" describes a method of gene amplification which involves sequenced-based hybridization of primers to specific genes within a DNA sample (or library) and subsequent amplification involving multiple rounds of annealing, elongation and denaturation using a heat-stable DNA polymerase. Such techniques are described in U.S. Pat. No. 4,683,202, the contents of which are herein incorporated by reference.

"RT-PCR" is an abbreviation for reverse transcriptase-polymerase chain reaction. Subjecting mRNA to the reverse transcriptase enzyme results in the production of CDNA which is complementary to the base sequences of the mRNA. Large amounts of selected cDNA can then be produced by means of the polymerase chain reaction which relies on the action of heat-stable DNA polymerase produced by *Thermus aquaticus* for its amplification action.

"Nucleus protection assay" refers to a method of RNA quantification which employs strand specific nucleuses to identify specific RNAs by detection of duplexes.

"In situ hybridization of RNA" refers to the use of labeled DNA probes employed in conjunction with histological sections on which RNA is present and with which the labeled probe can hybridize allowing an investigator to visualize the location of the specific RNA within the cell.

"Cloning" describes separation and isolation of single genes.

"Sequencing" describes the determination of the specific order of nucleic acids in a gene or polynucleotide.

The term "cleavage product" is defined as a polypeptide fragment produced from the targeted growth inhibitor described above by natural proteolytic processes. Preferably such a cleavage product will have biological activity including, but not limited to, tumor suppression and/or growth inhibition activity in mammalian prostate cancer cells. This term also includes such polypeptide fragments when produced via recombinant techniques and also includes biological functional equivalents of such fragments, the term biologically functional equivalent defined herein to include, among others, proteins in which biologically functionally equivalent amino acids have been inserted, and peptidomimetics.

Figure 3:
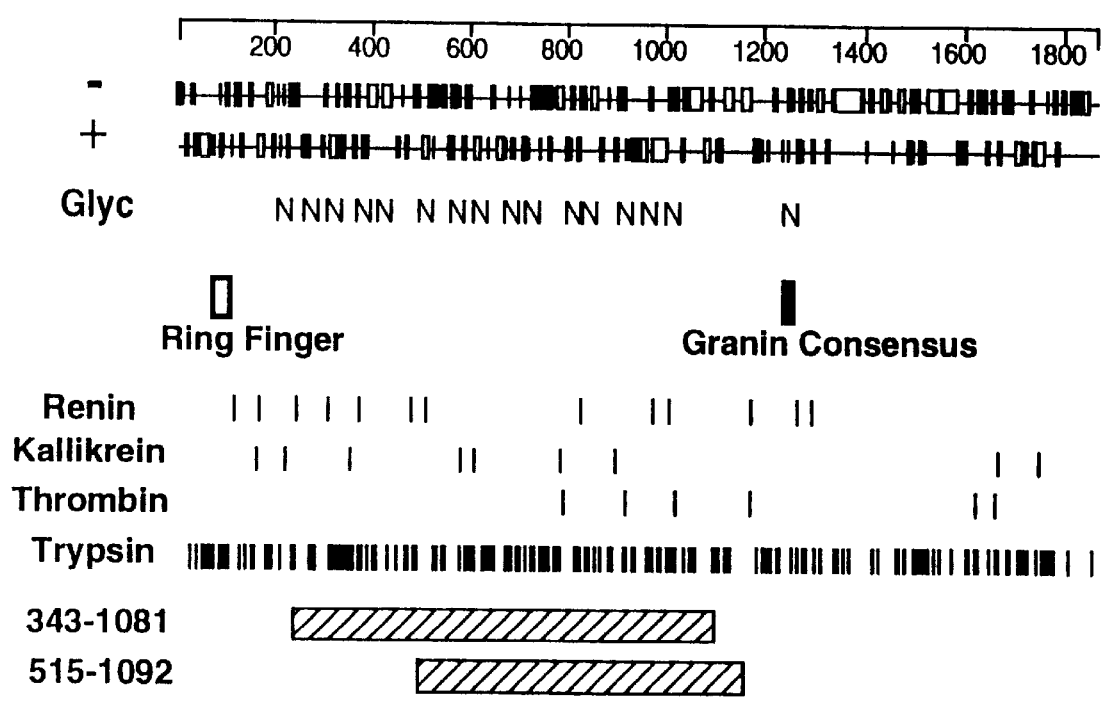
FIG. 3 is a diagram showing structural features of the human BRCA1 protein [SEQ ID NO:2] covering 864 amino acids.

The term "granin box domain" is defined as the consensus granin box domain of amino acids set forth in FIGS. 3 and 5.

The term "recombinant host cell" is defined as a single cell or multiple cells within a cell line which are capable of undergoing genetic manipulation through well-known and art recognized techniques of transformation, transfection, transduction and the like. Examples of contemplated recombinant host cells include, but are not limited to, cell lines derived from normal or cancerous mammalian prostate, breast or ovarian tissue, other eukaryotic cells, and microorganisms. Specific examples of recombinant host cells described herein include PPC-1 cells.

The phrase "operably linked" refers to a juxtaposition wherein the components so described are in a relationship permitting them to function in their intended manner. For instance, a promoter is operably linked to a coding sequence if the promoter affects its transcription or expression.

The practice of the present invention employs, unless otherwise indicated, conventional techniques of chemistry, molecular biology, microbiology, recombinant DNA, genetics, and immunology. (See, e.g., Maniatis et al., 1982; Sambrook et al., 1989; Ausubel et al., 1992; Glover, 1985; Anand, 1992; Guthrie & Fink, 1991).

Construction of Retroviral Vectors

Viral vectors containing a DNA sequence that encodes for a protein having an amino acid sequence as essentially set forth in SEQ ID NO:2 are constructed using techniques that are well known in the art. This sequence includes the BRCA1 gene product. Viral vectors containing a DNA sequence essentially set forth in SEQ ID NO:1 (the BRCA1 gene) can also be constructed using techniques that are well known in the art. See Sambrook et al., 1989 or Ausubel et al., 1992. Retroviral vectors such as the LXSN vector described herein, adenoviral vectors, or adeno-associated viral vectors are all useful methods for delivering genes into prostate cancer cells. The viral vector is constructed by cloning the DNA sequence as essentially set forth in SEQ ID NO:1 into a retroviral vector such as a prostate selective vector. Most preferably, the full length (coding region) cDNA for BRCA1 is cloned into the retroviral vector. The retroviral vector is then transfected into virus producing cells in the following manner: Viruses are prepared by transfecting PA317 cells with the retroviral vector DNAs which are purified in Wong et al., 1988. Following transfection, the PA317 cells are split and then treated with G418 until individual clones can be identified and expanded. Each clone is then screened for its titer by analyzing its ability to transfer G418 resistance (since the retroviral vector contains a Neomycin® resistance gene). The clones which have the highest titer are then frozen in numerous aliquots and tested for sterility, presence of replication-competent retrovirus, and presence of mycoplasma. Methods generally employed for construction and production of retroviral vectors have been described above and in Miller et al., 1990.

Once high titer viral vector producing clones are identified, then patients with prostate cancer are treated as described below.

It will be apparent to one having ordinary skill in the art that different length DNA segments encoding a BRCA family gene product can be cloned into the retroviral vectors. Well-known techniques such as restriction enzyme digests can be used to select sequences having lengths of particular interest. Moreover, the data more fully described herein characterizes appropriate sequence lengths. For example, the sequence of BRCA1 representing a splice variant encoding amino acids 72-1863 is a particularly useful one for growth inhibition studies of cancer cells including human prostate cancer cells.

Pharmaceutical Compositions

In a preferred embodiment, the present invention provides pharmaceutical compositions comprising a polypeptide or polynucleotide of the present invention and a physiologically acceptable carrier. More preferably, a pharmaceutical composition comprises a BRCA family polypeptide or a polynucleotide that encodes those polypeptides.

A composition of the present invention is typically administered parenterally in dosage unit formulations containing standard, well-known nontoxic physiologically acceptable carriers, adjuvants, and vehicles as desired. The term "parenteral" as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A transfected cell can also serve as a carrier. By way of example, a liver cell can be removed from an organism, transfected with a polynucleotide of the present invention using methods set forth above and then the transfected cell returned to the organism (e.g. injected intravascularly).

The prostate cancer susceptibility/tumor suppressor gene BRCA1 has a role in prostate cancer. Prostatic cancer cell lines that have lost expression of BRCA1 protein are inhibited by transfection of wild-type BRCA1, and small human prostate tumors established in mice are inhibited by injection of a retroviral vector expressing wild-type BRCA1.

An in vivo retroviral vector-mediated gene therapy for the treatment of advanced prostate cancer is also described. Prostate cancer provides a model system in which a retroviral vector is employed to direct gene transfer effects toward the malignant cells without producing expression in the nearby non-dividing cells. The use of retroviral vectors provides specificity since only cancer cells within the areas of injection are expected to express the LTR-regulated BRCA1 genes. Therefore, the likelihood of selective gene transfer to the tumor cells is enhanced. The uptake and expression of the viral vectors can be readily assessed in these model systems because these cells are readily accessible for pathologic, biochemical, and molecular analysis.

Gene therapy is the direct transfer of engineered DNA into diseased cells for the purpose of therapy. The gene therapy approach taken herein initially targets those patients who have end-stage prostate cancer and who have failed chemotherapy. Human gene therapy is facilitated by concurrent advances, particularly in the past five years, both in the molecular biology of vectors for recombinant DNA transfer and in the development of research strategies using therapeutic gene transfer in animal models of disease. Gene therapy approaches have been shown to be successful in numerous animal models.

The following examples are set forth to illustrate the subject invention. The examples should not be considered as limiting, the scope of the invention being defined by the claims appended hereto.

EXAMPLE 1

Wild Type BRCA1 Suppresses Cell Growth in Prostate Cell Lines with Low Expression of BRCA1 Protein In order to assess the effects of BRCA1 overexpression on cell growth, prostate cancer cell lines, PPC-1, DU145, LNCaP, PC3, and TSU, were transfected with wild-type and mutant BRCA1 genes. A Southern blot demonstrated transfer of the vector into transfected cell lines and tumors. Cell lines were characterized for BRCA1 at genomic, transcript, and protein expression levels. Genotypes of D17S855, D17S1322, D17S1327, D17S1326, and D17S1325 suggest that both alleles of BRCA1 are present in DU145, but that the other cell lines have lost one BRCA1 allele (Table 1). Levels of BRCA1 protein detectable by Western blot varied from none in PPC-1 and LNCaP to moderate in TSU.

Wild-type BRCA1 inhibited the growth of prostate cancer cell lines PPC-1, LNCaP, and DU145 (Table 1). Mutant BRCA1 constructs, whether RING finger missense, 5' or 3' truncation, or in-frame deletion, did not inhibit growth. Cell lines PC3 and TSU were not inhibited by BRCA1. The resistant lines express moderate or high levels of BRCA1 protein on Western blot, despite apparent 10 hemizygosity at the BRCA1 locus.

TABLE 1

Effect of BRCA1 expression vectors on growth of prostate cancer cells

| | PPC-1 | LNCaP | DU145 | PC3 | TSU |
|---|---|---|---|---|---|
| BRCA1 genotype in LXSN-BRCA1 vector | | | | | |
| wildtype | 0 + 0.3 | 1 + 0.3 | 4 + 1.4 | 73 + 3.9 | 130 + 4.5 |
| Cys61Gly | 79 + 0.6 | 41 + 2.2 | 70 + 2.0 | 73 + 2.7 | 139 + 5.5 |
| 340stop | 67 + 3.4 | 32 + 1.7 | 61 + 1.1 | 67 + 2.8 | 130 + 2.4 |
| del(343-1081) | 61 + 3.2 | 28 + 0.8 | 57 + 3.4 | 70 + 2.6 | 141 + 6.3 |
| 1835stop | 65 + 3.6 | 28 + 1.7 | 57 + 2.9 | 72 + 1.4 | 134 + 8.7 |
| Number of alleles at markers flanking BRCA1 | | | | | |
| D17855 | 1 | | 1 | 1 | 1 |
| D17S1322 | 1 | | 2 | 1 | 1 |
| D17S1327 | 1 | | 2 | 1 | 1 |
| D17S1326 | 1 | | 2 | 1 | 1 |
| D17S1325 | 1 | | 2 | 1 | 1 |
| BRCA1 transcript | + | | + | + | + |
| BRCA1 protein on Western blot | 0 | 0 | + | + | ++ |
| Source of cells | primary tumor | lymph node metastasis | brain metastasis | primary tumor | ? |

EXAMPLE 2

In vivo Transduction of Established PPC-1 Tumors by LXSN-BRCA1 in Nude Mice Slows Tumor Growth and Induces Tumor Regression LXSN-BRCA1 vectors were injected into established PPC-1 tumors to determine if wild-type BRCA1 could be integrated into tumor cells and inhibit tumor growth. The PPC-1 cell line was selected for tumor suppression studies in animals because it is derived from a primary prostatic cancer and because it forms reproducible and measurable flank tumors in mice. In the first experiment, 11 tumors were injected with the LXSN-BRCA1, 11 tumors with the parent vector LXSN, and 6 tumors with media alone (Table 2). When results of the first experiment suggested that initial tumor size might influence inhibition by BRCA1, 5 additional tumors were treated with BRCA1. Each treatment group included tumors ranging in size from 0.5 $mm^3$ to >5 $mm^3$. Gene transfer of the retroviral vector was demonstrated by Southern blot of cell lines and injected tumors. The vector could be detected in 20–40% of injected tumors.

Rate of tumor growth between day 0 and day 26 was measured by linear regression of tumor size on time after first treatment. Tumor growth was significantly different for mice treated with BRCA1 compared to either those treated with vector alone ($p<0.0001$) or media alone ($p<0.0001$). BRCA1 treatment significantly inhibited growth for tumors of all initial sizes, but the effect was most pronounced for the smallest tumors (<2 $mm^3$ at day 0) ($P<0.00001$). Small tumors were much more responsive to the single BRCA1 treatment than were larger tumors. All BRCA1 -treated tumors that were initially<2 $mm^3$ disappeared completely. Of tumors with initial masses of 2 to 5 $mm^3$ treated with BRCA1, two disappeared entirely, one decreased in size, and two grew substantially. The four tumors treated with BRCA1 only after their mass was >5 $mm^3$ grew, although less rapidly than did tumors of the same initial size treated with LXSN alone or only with media. The tumors of all mice injected with LXSN vector alone or with media alone grew steadily, although at variable rates. Histopathologic analysis of the injected tumors did not indicate any obvious change in differentiation of tumor cells nor any induction of necrosis, indicating that LXSN-BRCA1 suppresses tumors by inhibition of growth.

In summary, the human prostate tumors injected with the LXSN-BRCA1 retroviruses were 20 fold smaller than control tumors by 26 days after viral injection (uninjected control tumors, 109 (62 $mm^3$, n=6); LXSN tumors, 89 (32 $mm^3$, n=11); and LXSN-BRCA1 tumors, 5.4 (2 $mm^3$, n=16)

(Table 2). Moreover, 9/16 tumors in the LXSN-BRCA1 group completely disappeared by 26 days (Table 2). BRCA1 replacement by retroviral gene therapy dramatically suppresses human prostate cancer in the nude mouse model.

TABLE 2

Growth (mass in mm$^3$) of PPC-1 tumors in mice after injection of retroviral BRCA1, retrovirus alone, or control

|  | Day 0 | Day 16 | Day 26 |
| --- | --- | --- | --- |
| Initial tumors <2 mm$^3$ | | | |
| LXSN-BRCA1 | 0.52 | 0 | 0 |
| LXSN-BRCA1 | 0.52 | 0 | 0 |
| LXSN-BRCA1 | 0.52 | 0 | 0 |
| LXSN-BRCA1 | 0.52 | 0 | 0 |
| LXSN-BRCA1 | 0.52 | 0.98 | 0 |
| LXSN-BRCA1 | 0.98 | 0 | 0 |
| LXSN-BRCA1 | 1.57 | 0 | 0 |
| LXSN | 0.52 | 4.20 | 14.10 |
| LXSN | 1.77 | 14.10 | 14.40 |
| Control | 0.52 | 5.89 | 21.99 |
| Initial tumors 2.7–4.2 mm$^3$ | | | |
| LXSN-BRCA1 | 4.20 | 0 | 0 |
| LXSN-BRCA1 | 4.20 | 0 | 0 |
| LXSN-BRCA1 | 1.20 | 1.60 | 1.60 |
| LXSN-BRCA1 | 1.20 | 7.85 | 22.80 |
| LXSN-BRCA1 | 2.74 | 4.20 | 22.00 |
| LXSN | 2.74 | 17.86 | 22.00 |
| LXSN | 2.75 | 33.50 | 88.40 |
| LXSN | 2.75 | 33.50 | 219.90 |
| LXSN | 3.90 | 40.05 | 40.10 |
| LXSN | 4.10 | 33.50 | 110.00 |
| LXSN | 4.20 | 14.10 | 22.00 |
| LXSN | 4.20 | 33.50 | 40.10 |
| LXSN | 4.20 | 55.00 | 377.00 |
| Control | 2.74 | 17.67 | 33.50 |
| Control | 2.74 | 17.87 | 33.50 |
| Control | 2.74 | 22.00 | 86.40 |
| Initial tumors >5 mm$^3$ | | | |
| LXSN-BRCA1 | 5.89 | 4.20 | 7.85 |
| LXSN-BRCA1 | 7.85 | 0.52 | 4.20 |
| LXSN-BRCA1 | 7.85 | 5.90 | 14.10 |
| LXSN-BRCA1 | 14.10 | 7.85 | 14.0 |
| LXSN | 7.85 | 12.80 | 33.50 |
| Control | 5.89 | 17.87 | 33.50 |
| Control | 7.85 | 86.40 | 447.60 |

Overexpression of wild-type BRCA1 inhibits the growth of some prostate cancer cells but does not affect growth of other prostate cancer cell lines. Near full-length truncated BRCA1 proteins do not inhibit prostate cancer cell lines, showing similarities to breast cancer but not ovarian cancer phenotype. The variable BRCA1 expression and heterogeneous response to BRCA1 transfection suggest that BRCA1 contributes to prostate cancer pathogenesis in a complex manner.

Prostate cancer cell lines appear to show loss of heterozygosity (LOH) at chromosome 17 with some frequency. However, BRCA1 mRNA and protein levels do not clearly correlate with (LOH), or with androgen receptor status. This suggests a complex relationship between somatic allele loss of chromosome 17 and the expression level of BRCA1. Thus, until the disclosure of the instant application, a therapeutic method for prostate cancer treatment using the BRCA1 gene has not been suggested.

Gene transfer of wild-type BRCA1 into prostate cancer cell lines produced inhibition in some cell lines but no inhibition in other lines. This contrasts the results obtained following transfection of wild-type BRCA1 into breast and ovarian cancer cells which are generally inhibited, although some breast and ovarian cancer cell lines are not inhibited. The ability of transfected BRCA1 to inhibit prostate cancer cell growth did not cleanly correlate with (LOH), expression level or androgen receptor status although larger number of cell lines must be studied before these potential correlations can be completely excluded. Cells which were inhibited by wild-type BRCA1 transfection were not inhibited by transfection of truncation mutants or missense mutants (Table 1). The C-terminal mutant 1835stop did not inhibit the growth of prostate cancer cells. This mutant has previously been shown to inhibit the growth of breast cancer cells but not ovarian cancer cells, suggesting that the mechanism of inhibition of prostate cancer cells by BRCA1 shows similarities to inhibition of breast cancer but not ovarian cancer.

The mechanism of PPC-1 tumor suppression by LXSN-BRCA1 may be explained on the basis of growth inhibition since LXSN-BRCA1 growth inhibits PPC-1 cells in in vitro tissue culture studies.

Tumor suppression by LXSN-BRCA1 was dependent on tumor size (Table 2). This data is most consistent with a gene-based tumor suppression and not an immune-based gene therapy which might produce a generalized effect. Previous experience with this injection protocol indicates that this experimental approach results in retroviral vector integration into 20 to 40% of tumor cells adjacent to the site of injection. These results suggest that direct injection of retroviral vectors is more effective for tumors less than 1 cm$^3$. However, a 4.2 cm$^3$ tumor was eliminated by this approach. Repeated or multiple injections should allow effective treatment of larger tumors, as has been demonstrated in other model systems.

These results taken together suggest that BRCA1 contributes to pathogenesis of prostate cancer in a more phenotypically complex manner than breast or ovarian cancer. There is much more heterogeneity in results obtained with prostate cancer cells than was observed with analysis of breast and ovarian cancer. Whereas most breast and ovarian cancer lines show low expression of BRCA1, prostate cancer cell lines show variable expression. Similarly, the observation that transfection of BRCA1 inhibits only a proportion of prostate cancer cells emphasizes the heterogeneity of prostate cancer and suggests that prostate cancer cells may differ in BRCA1 signaling. This may explain why BRCA1 mutation produces only a relatively small increased risk of prostate cancer.

EXAMPLE 3

LXSN-BRCA1 Retroviral Therapy of Advanced Prostate Cancer

This example describes novel corrective prostate specific viral based gene therapy to combat advanced prostate cancer. Corrective gene therapy attempts to correct genetic mutations in cancer by replacing mutated tumor suppressor genes with normal ones. LXSN:BRCA1 retroviral gene therapy is applied to advanced prostate cancer by in vivo gene transfer of BRCA1 sequences with expression regulated by the Moloney long terminal repeat (LTR). Preclinical studies have revealed that prostate cancer cells that have low expression of BRCA1 protein are inhibited by the transfection of wild type BRCA1 and that small human prostate tumors established in nude mice are inhibited by the injection of a retroviral vector expressing wild type BRCA1. Transduction with these viral vectors results in marked tumor inhibition or even cure of some experimental animals with no clear-cut toxicity. The tissue selectivity of inhibition by BRCA1 may contribute to the limited toxicity which we have observed in studies in nude mice. Therefore, this example describes application of this method for the treatment of human advanced prostate cancer.

This example focuses on maximizing the delivery of retroviral vector to the tumor cells by repeated administrations into the orthotopic cancerous prostate in an attempt to increase the antitumor effect. Patients undergo a tissue examination prior to injection of retroviral vector (transrectal ultrasound quadrant injections). Pathologic, biochemical, and molecular studies are performed on biopsies to follow the extent of viral vector uptake by tumor cells and determine the stability of the viral vector. The clinical extent of tumor spread is measured before and after retroviral vector injection by clinical exam, ultrasound measurement of tumor volume, and serum prostate specific antigen (PSA).

Under transrectal ultrasound guidance, four needle cores of cells are removed (one from each prostate quadrant) per session and examined by methods cited above. Then, the retroviral vector is injected into the space left by the biopsy. The initial studies and injections are performed as an in-patient procedure within the Clinical Research Center, University of Tennessee-Memphis. Following the fourth injection session, the patient is discharged and then returns at two weeks and at four weeks for follow-up. In the event of death, a post-mortem examination quantifies tumor spread by careful dissection, measurement of tumor volume and weight, microscopically directed analysis of tumor extent, and molecular analysis of tumor and adjacent normal tissues to compare the extent of gene transfer between tumor cells and adjacent normal cells. More extensive tumor seeding requires repeated treatments with retroviral vector in order to achieve a therapeutic response, particularly since large tumors may be composed predominantly of slowly dividing cells which may require repeated exposure of the tumor cells to retroviral vector.

Overview of Therapy

Patients with advanced prostate cancer who meet the study criteria are treated with retroviral gene therapy by injection of retroviral vectors into the orthotopic prostate tumor. Retroviral vectors are manufactured from viral producer cells using serum-free conditions and are tested for sterility, absence of specific pathogens, and an absence of replication-competent retrovirus by standard assays. Retrovirus are stored frozen in large aliquots which have been tested according to FDA standards.

Patients are admitted to the Clinical Research Center, University of Tennessee-Memphis where they have a complete physical exam, blood, and urine tests to determine overall health. They bring with them a current bone scan, chest X-ray, electrocardiogram, and appropriate radiologic procedures to assess tumor stage.

Patients spend four days in the Clinical Research Center, University of Tennessee-Memphis for the initial injections of retroviral vector. Blood samples are drawn each day and tested for the presence of retroviral vector by sensitive polymerase chain reaction (PCR)-based assays. Patients with advanced prostate cancer have the cancer cells from their initial prostate biopsy analyzed to determine:

1. The percentage of cancer cells which are taking up the vector/gene combination by PCR and by in-situ hybridization;
2. The number of cancer cells present in the biopsy (cancer cell density);
3. Differentiation status of the cells (alcian blue/PAS);
4. Presence of programmed cell death (ApoTAG and DNA analysis);
5. Measurement of expression of BRCA1 target gene by immunohistochemistry and Western blot analysis.

Patients are continuously monitored while in the Clinical Research Center, University of Tennessee-Memphis. After the four day period in the Clinical Research Center they are discharged. Depending upon clinical status, they are either discharged to the Urology Division or to home, but all patients are asked to return at day 7 for a blood sample. After 4 weeks from the completion of the virus vector injections, the patients are reevaluated and undergo a prostate biopsy. After this evaluation the patients then proceed with chemotherapy or other options as clinically indicated to control temporarily their disease. Table 3 summarizes preliminary evaluation, screening, and treatment evaluation.

Maximally tolerated dose (MTD) of LXSN-BRCA1 when administered directly into the cancerous prostate is determined. Primary endpoints are: 1) the rate of transduction in tumor and/or normal cells, 2) the presence and stability of this vector in the systemic circulation and in prostate cancer cells, and 3) the nature of the systemic (fever, myalgias) and local (infections, pain) toxicities induced by this vector. A secondary endpoint is the clinical efficacy of LXSN-BRCA1.

Eligible patients with advanced prostate cancer are admitted to the Clinical Research Center, University of Tennessee-Memphis (CRC). Inclusion criteria are as follows:

1. Advanced prostate cancer
2. Patients who are >35 and <75 years old and who have signed informed consent
3. ECOG performance status (PS) $\geq 2$
4. Life expectancy of greater than 6 months
5. Recovery for at least 4 weeks from previous surgery and/or other cancer therapies
6. Adequate hematological (WBC's >4,000/mm$^3$, platelet count >100,000/mm$^3$), hepatic (bilirubin <mg/dL, SGOT <2×normal), and renal (creatinine <1.5 mg/dl) functions.

Exclusion criteria are as follows:

1. Localized prostate cancer
2. Active bacterial infections
3. Patients on concomitant experimental or other alternative therapies
4. Patients with heart failure (NYHA class 4), recent myocardial infarction, respiratory insufficiency, or hematological, hepatic, or renal dysfunction
5. Concomitant anticoagulant or antiplatelet drugs
6. Previous radiotherapy.

Selection is also based on presence of measurable disease, ECOG score, and inclusion/exclusion criteria set forth above. Patients are recruited through contacts with urologists, medical oncologists, and radiation oncologists who are currently providing care to the patient. Individual discussions with the patient and family members are scheduled to answer all concerns and questions about the method.

Prostate cancer tissue is collected for molecular studies by transrectal ultrasound guided biopsy using a biopsy gun. The vector was produced under current Good Manufacturing Practices and is provided by the Vector Production Facility at Vanderbilt University.

A 4 ml serum-free volume of retroviral vector (containing up to 5×10$^7$ viral particles in AIM V media) is administered daily per session. During each session, 1 ml of medium containing the appropriate titer of LXSN-BRCA1 is injected under transrectal ultrasound guidance into 4 regions of the prostate for a total of 4 ml per session in a clinical examination room. This is repeated daily for 4 days (4 sessions). Since the rectal wall is insensate, the patient should experience very little discomfort. This 16 ml total inoculum volume over 4 days is proportionally well below the one safely tolerated by nude mice (0.5 ml/20 g body weight). Moreover, the biopsy of 16 different areas of the prostate by transrectal ultrasound guidance assures representative sampling of the prostate.

Patient evaluation includes history and physical examination prior to initiation of therapy and daily during the 4 day period of vector injection. Toxicity grading is done using the ECOG Common Toxicity Criteria. CBC, SMA-20, urinalysis, and conventional studies are performed daily during this period (see Table 3 which presents parameters). Patients are allowed to proceed with any standard palliative alternatives (i.e., systemic chemotherapy) after the completion of vector administration. However, it is not expected that all patients will require immediate additional palliative interventions.

Dose Escalation and MTD

Three patients are treated with $3 \times 10^6$ viral particles×4. Once they have all recovered from all grade 2 or less toxicities (except alopecia), and as long as grade 3–4 toxicity is not encountered, a subsequent dose level is initiated in 3 additional patients. As one grade 3 or 4 toxicity occurs at a given dose level, a minimum of 6 patients are enrolled at that level. As only 1 of 6 patients has grade 3 or 4 toxicity, dose escalation continues. The MTD of LXSN-BRCA1 is defined as the dose where 2 of 6' patients experience grade 3 or 4 toxicity. If 2 of 3, or if 3 of 6 patients experience grade 3 or 4 toxicity, the MTD is defined as the immediately lower dose level.

The following escalation schema is followed: 1) level 1, $3 \times 10^6$ viral particles; 2) level 2, $1 \times 10^7$; 3) level 3, $3 \times 10^7$; 4) level 4, $5 \times 10^7$.

Studies of Retroviremia

Previous preclinical data indicate that injection of relatively large quantities of vector into the peritoneal space results in detectable amounts of vector in the peripheral blood in mice, although detectable vector in peripheral blood in patients treated with up to $10^{10}$ vector transducing units has not been observed. This problem may be explained by the large volume of literature which indicates that human serum destroys retroviral particles. This issue is addressed in patients by obtaining 20 ml of blood during each of the four days that the patients are present in the Clinical Research Center, University of Tennessee-Memphis, and separating the blood into serum and cellular components for PCR detection.

If the viral vector is detected within the serum component, then the following assay to identify the existence of transduction-capable viral vector is performed. Serum is incubated with PPC-1 target cells, and DNA is obtained from PPC-1 cells before and after attempted transduction.

Criteria for Clinical Response

Patients with measurable disease are evaluated for a clinical response to LXSN-BRCA1, especially those that do not undergo a palliative intervention immediately after retroviral vector therapy. Prostate histology, prostatic volume by ultrasound, PSA, and local symptoms are followed. For other sites of disease, conventional response criteria are used as follows:

1. Complete Response (CR)—complete disappearance of all measurable lesions and of all signs and symptoms of disease for at least 4 weeks.

2. Partial Response (PR)—decrease of at least 50% of the sum of the products of the 2 largest perpendicular diameters of all measurable lesions as determined by 2 observations not less than 4 weeks apart. To be considered a PR, no new lesions should have appeared during this period and none should have increased in size.

3. Stable Disease—less than 25% change in tumor volume from previous evaluations.

4. Progressive Disease—greater than 25% increase in tumor measurements from previous evaluations.

Potential Risks

1. Blood collection

Bruising and infection.

2. Prostate biopsy

There will be some discomfort and the possibility of bleeding or infection related to the biopsy. In rare instances, this infection can lead to fever.

3. Vector injection—It is possible that a person may have an allergic reaction to the injection although this should be a rare complication since no animal serum is used to prepare the vector for injection. The retroviral vector may kill tumor cells producing necrosis and release of these factors into the blood stream resulting in fever, changes in blood chemistry, changes in white blood cell count, and the possibility of uric acid kidney stones.

4. Retroviral vector replication—The retroviral vectors employed herein are unable to reproduce or replicate. Unknown or uncommon side effects may occur including ones that may be severe since this is a new form of cancer treatment.

5. Safety precautions

1) Blood collection: The site is swabbed with alcohol to minimize the risk of infection. In addition, pressure is placed in the venipuncture site to prevent bruising or bleeding.

2) Prostate biopsy: The patient receives antibiotic prophylaxis with a Cipro 500 mg PO BID the day before biopsy, the day of biopsy, and the day after biopsy. This has been proven to be effective in preventing infection related to a transrectal biopsy. Pressure can be maintained at the site of biopsy to minimize bleeding.

3) Vector injection: As mentioned above, the vector is prepared as specified by the FDA including the use of AIM V which is an animal serum-free media. The packaging cell lines have been fully tested free of any other potential pathogens.

4) Vector replication: Blood samples and tissue are tested on a routine basis for the presence of helper virus activity. The patients are followed very closely to see if any side effects are indeed occurring which is the reason that they spend 4 full days in the CRC during treatment.

All data is collected and tabulated with the utmost concern for the patient's privacy and confidentiality. The data includes molecular studies of blood and prostate tissue in addition to history and physical examination, tumor status, performance status, toxicity assessments, weight, complete blood counts, PT/PTT, urinalysis, blood urea nitrogen & creatinine, liver function tests, serum chemistries, chest x-ray, electrocardiogram, and serum prostate-specific antigen. Prostate tissue, fixed or frozen, as well as serum samples are stored by number in a −70° freezer.

TABLE 3

Study Parameters for Clinical Trial Flow Sheet

| PreTreatment Routine Studies | Daily (Rx)[5] | 2 weeks during Rx | 4 weeks post-RX | Monthly post-Rx | X11 | Yearly |
|---|---|---|---|---|---|---|
| History & Physical | X | X | X | X | X | X |
| Assess Tumors Status | X | X | X | X | X | X |
| Performance Status | X | X | X | X | X | X |
| Toxicity Assessment | X | X | X | X | X | X |
| Weight X | X | X | X | X | X | X |
| Complete Blood Count | X | X | X | X | X | X |
| PT,PTT | X | X | X | X | X | X |
| Urinalysis | X | X | X | X | X | X |
| BUN & Creatinine | X | X | X | X | X | X |
| Liver Function Tests[2] | X | X | X | X | X | X |
| Serum Chemistries[3] | X | X | X | X | X | X |
| Chest X-ray | X | ACI | ACI | ACI | ACI | ACI |
| EKG X | ACI | ACI | ACI | ACI | ACI | |
| PSA X | X | X | X | X | X | |
| Circulating env antibodies | X | X | X | X | X | X |
| Prostate biopsy | X | X | X | X | | |

[1]To include: hematocrit, hemoglobin, differential, and platelets
[2]To include: alkaline phosphatase, serum transaminases, bilirubin, protein, LDH, and albumin
[3]To include: Na, K, Ca, PO4, Cl, Magnesium, CO2, and glucose Table 4 presents the partial response observed in six out of nineteen patients who have been treated with the LXSN-BRCA1 gene therapy methods described herein. As more fully defined above, a partial response is defined as greater than 50% tumor shrinkage. The data indicate the percent tumor size shrinkage observed in these patients. This is determined by doing ultrasounds on the tumors before and after therapy.

TABLE 4

| Patient Number | Percent Tumor Size Shrinkage |
|---|---|
| 1 | 53 |
| 2 | 50 |
| 3 | 51 |
| 4 | 54 |
| 5 | 61 |
| 6 | 52 |

EXAMPLE 4

Gene Therapy of Prostate Cancer Using the BRCA2 Gene.

The protein encoded by the BRCA2 breast and ovarian cancer susceptibility gene (Wooster, R. et al. 1995) includes a domain similar to the granin consensus at the C-terminus of the protein. As seen in FIG. 5, the sequence at amino acids 3334–3344 of Genbank locus HUS43746 matches six of the seven constrained sites of the granin consensus. BRCA2 and murine BRCA1 differ from the consensus at the same site. The granin motif in BRCA2 lies at the extreme C-terminal end of the protein, a locale characteristic of a known granin. This indicates that the protein encoded by the BRCA2 gene is also a secreted growth inhibitor. Use of both the BRCA1 and BRCA2 genes offers the opportunity for a unified approach to the treatment of prostate cancer. Accordingly, the examples set forth above depicting the treatment of prostate cancer, are equally applicable to the BRCA2 gene and the BRCA2 gene product.

The identification of BRCA1 and BRCA2 as granins indicate that there is a granin superfamily which consists of the subfamilies of chromogranins (chromogranins A, B and C); secretogranins (secretogranins III-V) and the BRCA-granins (BRCA1, BRCA2 and other tumor suppressor genes). This classification of granin into these subclasses is based on greater similarities within the subfamilies than with the superfamily as a whole. For example, chromogranins share an additional region of homology besides the granin consensus and exhibit similar expression patterns; the secretogranins show less homology to the granin consensus than either chromogranins or BRCA granins; the BRCA granins BRCA1 and BRCA2 are cancer susceptibility genes, contain additional regions of homology, and are significantly larger (two-twenty times larger) than other granins described to date.

Thus, the invention provides in Example 3 and in this Example a granin box consensus sequence shown in FIG. 5. Thus, provided is a family of proteins which share the consensus sequence and that are tumor suppressor genes. BRCA1 and BRCA2 are members of this family. Other members may be identified and purified as tumor suppressor genes by genetic methods, by DNA-based searches for granin homology, or by cloning and characterization of granins in prostate cancer cells by biochemical methods. Such biochemical methods include the isolation and purification of proteins from the secretory vesicles or Golgi by physical isolation methods, followed by development of antibodies to determine which proteins, followed by cloning of genes for secreted proteins after protein sequencing and cloning with degenerate oligonucleotide primers. An example of this method is described in Colomer et al., 1996. Thus, other BRCA granins are contemplated to be within the scope of this invention. Accordingly, the therapy methods described herein are contemplated to be effective using other BRCA granins as well as BRCA1 and BRCA2.

Therefore, the term "BRCA family" as used herein and in the claims, is contemplated to include the BRCA granins described in this Example as well as BRCA1 and BRCA2 genes and gene products. The BRCA family is characterized by the tumor suppressor activity of the gene product and the granin box consensus sequence shown in FIG. 5.

EXAMPLE 5

Gene Transfer Using Liposomes

An alternative method of gene therapy using the BRCA1 and BRCA2 gene, and BRCA gene family includes the use of liposomes to deliver the DNA into the cells. By this method, the above described LXSN-BRCA1 plasmid is incubated with a liposome preparation such as cationic liposomes and then the DNA liposome mix is added to cells or injected into an animal or patient. Generally, the liposome transfection method is of a lower efficiency than viral gene transfer methods. This method is made more useful because the BRCA1 and BRCA2 and BRCA granin proteins are secreted proteins. Thus, if only a few percent of cells take up the DNA-liposome combination, it is likely that enough gene product will be produced and secreted from these cells to growth inhibit other cells. Liposomal transfection of nucleic acids into host cells is described in U.S. Pat. Nos. 5,279,833; 5,286,634; 5,651,964; 5,641,484; and 5,643,567, the contents of each of which are herein incorporated by reference.

EXAMPLE 6

Anti-sense Inhibition of the Production of BRCA1 Protein

The antisense inhibition of BRCA1 is described as follows. Antisense methods are used to demonstrate that BRCA1 expression inhibits cell growth. Unmodified 18 base deoxyribonucleotide complementary to the BRCA1 translation initiation site are synthesized and are added to cultures of primary prostate cancer cells at a concentration of 40 $\mu$M according to well-known procedures.

Upon acceleration of the growth of prostate cancer cells via antisense inhibition of BRCA1, chemotherapeutic methods of treating prostate cancer are improved. Because chemotherapy is most effective in cancer cells which are rapidly dividing, it is possible then to treat prostate cancer by accelerating growth of cancer cells by antisense inhibition of BRCA1 protein expression and by treating with chemotherapeutic drugs using standard chemotherapy protocols.

EXAMPLE 7

Treatment of Prostate Cancer Using Purified BRCA1 or BRCA2 Gene Product

Alternatively, prostate cancer is treated by the administration of a therapeutically effective amount of the BRCA1 or BRCA2 gene product via an efficient method, such as injection into a tumor. A therapeutically effective amount can be determined by one having ordinary skill in the art using well-known protocols.

It is important to note that prostate cancer cells have surface receptors which can be contacted by the BRCA1 or BRCA2 gene product. Thus, the BRCA1 or BRCA2 gene product, an active fragment, or a small molecule mimetic binds directly to a receptor on the surface of the prostate cancer cells. BRCA1 and BRCA2 targeted growth inhibitor agents as defined herein are preferred examples.

EXAMPLE 8

Method of Treating Prostate Cancer Comprising Introducing the BRCA1 Receptor Gene and the BRCA1 Protein into a Prostate Cancer Cell The loss of the BRCA1 receptor in prostate cancer cells will lead to proliferation and tumorigenesis in these cells. Thus, prostate cancer can be treated by introducing the BRCA1 receptor gene into prostate cancer cells using the gene therapy methods described above. This step will be followed by the administration of a therapeutically effective amount of the BRCA1 gene product so that the BRCA1 gene product contacts a receptor on a surface of the prostate cells. A therapeutically effective amount can be determined by one having ordinary skill in the art using well-known protocols.

The BRCA1 receptor gene is isolated using standard techniques. The BRCA2 receptor gene can be similarly isolated.

Baculovirus BRCA1 is purified from the insect cells with an antibody derived from the last twenty amino acids of the carboxy terminius of the BRCA1 gene product (the C20 antibody) and then labeled with radioactive iodine by standard methods. Cys61Gly and termination codon mutant BRCA1 proteins are prepared and labelled as a control. The labelled BRCA1 then can be used to perform binding studies to identify cells with BRCA1 receptors using Scatchard analysis and to perform cross-linking studies which demonstrate the BRCA1 receptor(s) on polyacrylamide gels. These initial characterization methods are used to identify cells with high and low numbers of BRCA1 receptor(s) for purification and isolation studies. Once a cell line with high levels of BRCA1 receptor has been identified, then the protein is purified by the following approaches:

Approach A: Biochemical purification.

The cell line which expresses high levels of BRCA1 receptor is lysed and the protein from cell lysates or membrane preparations is purified by gel filtration, followed by purification of the receptor with a column containing the BRCA1 ligand bound to a solid phase such as sepharose. The purified receptor protein can then be microsequenced and the gene cloned using degenerate oligonucleotides derived from the protein sequence.

Approach B:

Ligand is radiolabeled with 125I and then used to screen cell lines or tissues for specific binding by Scatchard analysis. Once such binding is identified, a cDNA library is constructed from that tissue or cell line and transfected into a cell line that does not exhibit specific binding. These transfected cells are then screened for newly acquired specific binding which indicates they have been transfected with a construct containing the gene for the BRCA1 receptor. Plasmid DNA from positive clones is then isolated and sequenced for identification. This single construct is then transfected back into the null cells to verify that binding of ligand is mediated by the transfected gene. (Kluzen et al. 1992).

Alternatively, chimeric BRCA1 and immunoglobulin Fc molecules can be constructed. (LaRochelle et al. 1995). The chimeric molecules are then used to screen for binding to BRCA1 receptor on whole cells via flow cytometry. Alternatively, due to the presence of the immunoglobulin component of the molecule, cell lysates are screened by immunoblotting or by immunoprecipitation of metabolically labelled cells. This technique can identify BRCA1 binding proteins by a variety of different methods. Peptide digests of the identified proteins are then generated so that the peptides can be sequenced and the whole molecule cloned by a degenerative oligonucleotide approach.

EXAMPLE 9

Method of Preventing Prostate Cancer Using BRCA1 or BRCA2 Protein

BRCA1 gene product is used as a chemopreventive agent by introducing BRCA1 directly into the prostate as the whole protein, as a functional fragment, or as a functional cleavage product. In addition, compounds that induce expression of BRCAL or activate its receptor, e.g., a small molecule mimetic, could also be introduced.

Gene therapy approaches for increasing the expression of BRCA1 in the prostate gland directly or indirectly could also be used. Systemic agents that induce the expression of BRCA1, or that mimic function and can replace BRCA1, such a peptidomimetic agent, could also be used. The delivery of such agents could take place by directly instilling the agent within the prostate. Finally, an implantable time release capsule can be used in a prevention strategy, by placing such a capsule in the prostate for prostate cancer.

Since the BRCA2 protein includes a granin sequences and is also a secreted tumor suppressor protein, similar prevention strategies can be applied using the BRCA2 gene and protein.

Thus, because patients with mutations in BRCA1 or BRCA2 have an increased incidence of prostate cancer, overexpression of BRCA1 or BRCA2 genes (or stimulated expression of endogenous BRCA1 or BRCA2 genes) is likely useful in preventing the development of prostate cancer.

References

Adelman, et al. *DNA* 2:183, 1983.
Anand, R. *Techniques for Analysis of Complex Genomes*, (Academic Press), 1992.
Anderson, D. E. and Badzioch, N. M. *Cancer* 72:114–119, 1993.
Ausubel, F. M., et al. *Current Protocols in Molecular Biology*, (J. Wylie & Sons, N.Y.), 1992.
Breast Cancer Information Core (1996) www.nchgr.nih.gov/Intramural_research/Lab-transfer/Bic/Brothman, A. R. et al. *Genes, Chrom. Cancer* 13:278–284, 1995.
Carter, H. B. et al. *J. Urol.* 143:742, 1990.
Cato, A. C. et al. *J. Steroid Biochem.* 34:139, 1989.
Chen, Y. et al. *Science* 270:789–791, 1995.
Choi, Y. Et al. *J. Virol.* 61:3013, 1987.
Cliby, W. et al. *Cancer Res.* 53:2393–2398, 1993.
Colomer, et al. *J. Biol. Chem.* 271:48–55, 1996.
Crea, et al. *Proc. Natl. Acad. Sci. U.S.A* 75:5765, 1978.
Cropp, C. S. et al. *Cancer Res.* 53:5617–5619, 1993.
Dodd, J. G. et al. *J. Biol. Chem.* 258:10731–10737, 1983.
Eichenlaub, R. J. *Bacteriol* 138:559–566, 1979.
Ford, D. et al. *Breast Cancer Linkage Consortium.* Lancet 343:692–695, 1994.
Friedman, L. S. et al. *Nature Genet* 8:399–404, 1994.
Futreal, P. A. et al. *Science* 266:120–122, 1994.
Gao, X. et al. *Oncogene* 11:1241–1247, 1995.
Gao, X. et al. *Cancer Res.* 55:1002–1005, 1995.
Glover, D. *DNA Cloning*, 1 and 2, (Oxford Press), 1985.
Greenberg, N. M. et al. *Mol. Endocrinol.* 8:230–239, 1994.
Greenberg, N. M. et al. *Proc. Natl. Acad. Sci. USA* 92:3439–3443, 1995.
Gribskov et al. *Nucl. Acids Res.*, 14:6745, 1986.
Guthrie, G. and Fink, G. R. *Guide to Yeast Genetics and Molecular Biology*, (Academic Press), 1991.
Hall, J. M. et al. *Science* 250:1684–1689, 1990.
Halter, S. A. et al. *Am. J. Pathol.* 140:1131, 1992.
Hamdy, F. C. et al. *Br. J. Urol.* 69:392–396, 1992.
Holt, J. T. et al. *Nature Genet* 12:298–302, 1996.
Hopp, U.S. Pat. No. 4,554,101.
Isaacs, S. D. et al. *J. Natl. Cancer Inst.* 87:991–996, 1995.
Jensen, R. A. et al. *Nature Genet* 12:303–308, 1996.
Jishi, M. F. et al. *Cancer* 76:1416–1421, 1995.
Jurincic, C. D. et al. *Urol. Int.* 45:153–159, 1990.
Kanehisa, *Nucl. Acid Res.*, 12:203–213, 1984.
Kluzen et al., *Proc Natl Acad Sci USA* 89:4618–4622, 1992.
Kyte & Doolittle, *J. Mol. Biol.*, 157:105–132, 1982.
Langston, A. A. et al. *Am. J. Hum. Genet.* 58:881–84, 1996.
LaRochelle, et al. *J. Cell. Biol.* 129:357–366, 1995. Maniatis et al. *Molecular Cloning: A Laboratory Manual* (Coldspring Harbor Laboratory, Coldspring Harbor, N.Y.), 1982.
Matsui, Y. et al. *Cell* 61:1147, 1990.
Matuo, Y. et al. In vitro *Cell Dev. Biol.* 25:581–584, 1989.
Messing et al. *Third Cleveland Symposium on Macromolecules and Recombinant DNA*, Editor A. Walton, Elsevier, Amsterdam, 1981.
Miki, Y. et al. *Science* 266:66–71, 1994.
Miller, et al. *Methods in Enzym.*, 217:588–599, 1990.
Mulders, T. M. T. et al. *Eur. J. Surg. Oncol.* 16:37–41, 1990.
Muller, W. J. et al. *EMBO J.* 9:907, 1990.
Murakami, Y. S. et al. *Cancer Res.* 55:3389–3394, 1995.
Needleman, et al., *J. Mol. Biol.*, 48:443, 1970.
Neuhausen, S. L. and Marshall, C. J. *Cancer Res.* 54:6069–6072, 1994.
Newman, B. et al. *Proc. Natl. Acad. Sci. USA* 85:3044–3048, 1988.
Oesterling, J. E. *J. Urol.* 145:907–923, 1991.
Pang, S. et al. *Human Gene Therapy* 6:1417–1426, 1995.
Russell, S. E. et al. *Oncogene* 5:1581–1583, 1990.
Saito, H. et al. *Cancer Res.* 53:3382–3385, 1993.
Sambrook, et al. *Molecular Cloning Laboratory Manual*, 2d Edition, 1989.
Schwartz et al., eds., *Atlas of Protein Sequence and Structure*, National Biomedical Research Foundation, pp. 353–358, 1979.
Sellers, T. A. et al. *J. Natl. Cancer Inst.* 86:1860–1865, 1994.
Smith, et al. *Adv. Appl. Math.*, 2:482 1981.
Smith, S. A. et al. *Nature Genet* 2:128–131, 1992.
Struewing, J. P. et al. *Am. J. Hum. Genet.* 57:1–7, 1995.
Takahashi, H. et al. *Cancer Res.* 55:2998–3002, 1995.
Thompson, M. E. et al. *Nature Genetics* 9:444–450, 1995.
Tulinius, H. et al. *I. Med. Genet.* 31:618–621, 1994.
Tutrone, R. F. et al. *J. Urol.* 149:633–639, 1993.
U.S. Pat. No. 4,683,202.
Walsh, P. C. *Urology* 44:463, 1994.
Wetmur & Davidson, *J. Mol. Biol.* 31:349–370, 1968.
Williams, B. J. et al. *J. Urology* 155:720–725, 1996.
Wong et al. *Proceeding of the UCLA Symposium on Biology of Leukemias and Lymphomas*, Golde, D. (ed), Allan R. Liss, Inc. 61:553–556, 1988.
Wooster, R. et al. *Nature* 379:789–792, 1995.
Yang-Feng, T. L. et al. *Int. J. Cancer* 54:546–551, 1993.

It will be understood that various details of the invention may be changed without departing from the scope of the invention. Furthermore, the foregoing description is for the purpose of illustration only, and not for the purpose of limitation—the invention being defined by the claims.

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 5712
      (B) TYPE: nucleic acid
      (C) STRANDEDNESS: double
      (D) TOPOLOGY: linear (ix) FEATURE:
      (A) NAME/KEY: BRCA1
      (B) LOCATION: GenBank accession no. U14680

(x) PUBLICATION INFORMATION:
      (A) AUTHORS: Miki, Y., et. al.
      (B) TITLE: A strong candidate gene for the breast and
            ovarian cancer susceptibility gene BRCA1.
      (C) JOURNAL: Science
      (D) VOLUME: 266
      (E) PAGES: 66-71
      (F) DATE: 1994

(xi) SEQUENCE DESCRIPTION: SEQ ID NO:1:

```
agctcgctga gacttcctgg accccgcacc aggctgtggg gtttctcaga taactgggcc     60
cctgcgctca ggaggccttc accctctgct ctgggtaaag ttcattggaa cagaaagaaa    119 atg gat tta tct gct ctt cgc gtt gaa gaa gta caa aat gtc att aat      167
Met Asp Leu Ser Ala Leu Arg Val Glu Glu Val Gln Asn Val Ile Asn
1               5                  10                  15 gct atg cag aaa atc tta gag tgt ccc atc tgt ctg gag ttg atc aag      215
Ala Met Gln Lys Ile Leu Glu Cys Pro Ile Cys Leu Glu Leu Ile Lys
            20                  25                  30 gaa cct gtc tcc aca aag tgt gac cac ata ttt tgc aaa ttt tgc atg      263
Glu Pro Val Ser Thr Lys Cys Asp His Ile Phe Cys Lys Phe Cys Met
        35                  40                  45 ctg aaa ctt ctc aac cag aag aaa ggg cct tca cag tgt cct tta tgt      311
Leu Lys Leu Leu Asn Gln Lys Lys Gly Pro Ser Gln Cys Pro Leu Cys
    50                  55                  60 aag aat gat ata acc aaa agg agc cta caa gaa agt acg aga ttt agt      359
Lys Asn Asp Ile Thr Lys Arg Ser Leu Gln Glu Ser Thr Arg Phe Ser
65                  70                  75                  80 caa ctt gtt gaa gag cta ttg aaa atc att tgt gct ttt cag ctt gac      407
Gln Leu Val Glu Glu Leu Leu Lys Ile Ile Cys Ala Phe Gln Leu Asp
                85                  90                  95 aca ggt ttg gag tat gca aac agc tat aat ttt gca aaa aag gaa aat      455
Thr Gly Leu Glu Tyr Ala Asn Ser Tyr Asn Phe Ala Lys Lys Glu Asn
            100                 105                 110 aac tct cct gaa cat cta aaa gat gaa gtt tct atc atc caa agt atg      503
Asn Ser Pro Glu His Leu Lys Asp Glu Val Ser Ile Ile Gln Ser Met
        115                 120                 125 ggc tac aga aac cgt gcc aaa aga ctt cta cag agt gaa ccc gaa aat      551
Gly Tyr Arg Asn Arg Ala Lys Arg Leu Leu Gln Ser Glu Pro Glu Asn
    130                 135                 140 cct tcc ttg cag gaa acc agt ctc agt gtc caa ctc tct aac ctt gga      599
Pro Ser Leu Gln Glu Thr Ser Leu Ser Val Gln Leu Ser Asn Leu Gly
145                 150                 155                 160 act gtg aga act ctg agg aca aag cag cgg ata caa cct caa aag acg      647
Thr Val Arg Thr Leu Arg Thr Lys Gln Arg Ile Gln Pro Gln Lys Thr
                165                 170                 175
```

-continued

| | |
|---|---|
| tct gtc tac att gaa ttg gga tct gat tct tct gaa gat acc gtt aat<br>Ser Val Tyr Ile Glu Leu Gly Ser Asp Ser Ser Glu Asp Thr Val Asn<br>            180                    185                    190 | 695 |
| aag gca act tat tgc agt gtg gga gat caa gaa ttg tta caa atc acc<br>Lys Ala Thr Tyr Cys Ser Val Gly Asp Gln Glu Leu Leu Gln Ile Thr<br>            195                    200                    205 | 743 |
| cct caa gga acc agg gat gaa atc agt ttg gat tct gca aaa aag gct<br>Pro Gln Gly Thr Arg Asp Glu Ile Ser Leu Asp Ser Ala Lys Lys Ala<br>210                    215                    220 | 791 |
| gct tgt gaa ttt tct gag acg gat gta aca aat act gaa cat cat caa<br>Ala Cys Glu Phe Ser Glu Thr Asp Val Thr Asn Thr Glu His His Gln<br>225                    230                    235                    240 | 839 |
| ccc agt aat aat gat ttg aac acc act gag aag cgt gca gct gag agg<br>Pro Ser Asn Asn Asp Leu Asn Thr Thr Glu Lys Arg Ala Ala Glu Arg<br>                  245                    250                    255 | 887 |
| cat cca gaa aag tat cag ggt agt tct gtt tca aac ttg cat gtg gag<br>His Pro Glu Lys Tyr Gln Gly Ser Ser Val Ser Asn Leu His Val Glu<br>            260                    265                    270 | 935 |
| cca tgt ggc aca aat act cat gcc agc tca tta cag cat gag aac agc<br>Pro Cys Gly Thr Asn Thr His Ala Ser Ser Leu Gln His Glu Asn Ser<br>275                    280                    285 | 983 |
| agt tta tta ctc act aaa gac aga atg aat gta gaa aag gct gaa ttc<br>Ser Leu Leu Leu Thr Lys Asp Arg Met Asn Val Glu Lys Ala Glu Phe<br>            290                    295                    300 | 1031 |
| tgt aat aaa agc aaa cag cct ggc tta gca agg agc caa cat aac aga<br>Cys Asn Lys Ser Lys Gln Pro Gly Leu Ala Arg Ser Gln His Asn Arg<br>305                    310                    315                    320 | 1079 |
| tgg gct gga agt aag gaa aca tgt aat gat agg cgg act ccc agc aca<br>Trp Ala Gly Ser Lys Glu Thr Cys Asn Asp Arg Arg Thr Pro Ser Thr<br>                  325                    330                    335 | 1127 |
| gaa aaa aag gta gat ctg aat gct gat ccc ctg tgt gag aga aaa gaa<br>Glu Lys Lys Val Asp Leu Asn Ala Asp Pro Leu Cys Glu Arg Lys Glu<br>            340                    345                    350 | 1175 |
| tgg aat aag cag aaa ctg cca tgc tca gag aat cct aga gat act gaa<br>Trp Asn Lys Gln Lys Leu Pro Cys Ser Glu Asn Pro Arg Asp Thr Glu<br>355                    360                    365 | 1223 |
| gat gtt cct tgg ata aca cta aat agc agc att cag aaa gtt aat gag<br>Asp Val Pro Trp Ile Thr Leu Asn Ser Ser Ile Gln Lys Val Asn Glu<br>            370                    375                    380 | 1271 |
| tgg ttt tcc aga agt gat gaa ctg tta ggt tct gat gac tca cat gat<br>Trp Phe Ser Arg Ser Asp Glu Leu Leu Gly Ser Asp Asp Ser His Asp<br>385                    390                    395                    400 | 1319 |
| ggg gag tct gaa tca aat gcc aaa gta gct gat gta ttg gac gtt cta<br>Gly Glu Ser Glu Ser Asn Ala Lys Val Ala Asp Val Leu Asp Val Leu<br>                  405                    410                    415 | 1367 |
| aat gag gta gat gaa tat tct ggt tct tca gag aaa ata gac tta ctg<br>Asn Glu Val Asp Glu Tyr Ser Gly Ser Ser Glu Lys Ile Asp Leu Leu<br>            420                    425                    430 | 1415 |
| gcc agt gat cct cat gag gct tta ata tgt aaa agt gaa aga gtt cac<br>Ala Ser Asp Pro His Glu Ala Leu Ile Cys Lys Ser Glu Arg Val His<br>435                    440                    445 | 1463 |
| tcc aaa tca gta gag agt aat att gaa gac aaa ata ttt ggg aaa acc<br>Ser Lys Ser Val Glu Ser Asn Ile Glu Asp Lys Ile Phe Gly Lys Thr<br>            450                    455                    460 | 1511 |
| tat cgg aag aag gca agc ctc ccc aac tta agc cat gta act gaa aat<br>Tyr Arg Lys Lys Ala Ser Leu Pro Asn Leu Ser His Val Thr Glu Asn<br>465                    470                    475                    480 | 1559 |
| cta att ata gga gca ttt gtt act gag cca cag ata ata caa gag cgt<br>Leu Ile Ile Gly Ala Phe Val Thr Glu Pro Gln Ile Ile Gln Glu Arg<br>                  485                    490                    495 | 1607 |

```
ccc ctc aca aat aaa tta aag cgt aaa agg aga cct aca tca ggc ctt      1655
Pro Leu Thr Asn Lys Leu Lys Arg Lys Arg Arg Pro Thr Ser Gly Leu
            500                 505                 510 cat cct gag gat ttt atc aag aaa gca gat ttg gca gtt caa aag act      1703
His Pro Glu Asp Phe Ile Lys Lys Ala Asp Leu Ala Val Gln Lys Thr
        515                 520                 525 cct gaa atg ata aat cag gga act aac caa acg gag cag aat ggt caa      1751
Pro Glu Met Ile Asn Gln Gly Thr Asn Gln Thr Glu Gln Asn Gly Gln
    530                 535                 540 gtg atg aat att act aat agt ggt cat gag aat aaa aca aaa ggt gat      1799
Val Met Asn Ile Thr Asn Ser Gly His Glu Asn Lys Thr Lys Gly Asp
545                 550                 555                 560 tct att cag aat gag aaa aat cct aac cca ata gaa tca ctc gaa aaa      1847
Ser Ile Gln Asn Glu Lys Asn Pro Asn Pro Ile Glu Ser Leu Glu Lys
            565                 570                 575 gaa tct gct ttc aaa acg aaa gct gaa cct ata agc agc agt ata agc      1895
Glu Ser Ala Phe Lys Thr Lys Ala Glu Pro Ile Ser Ser Ser Ile Ser
        580                 585                 590 aat atg gaa ctc gaa tta aat atc cac aat tca aaa gca cct aaa aag      1943
Asn Met Glu Leu Glu Leu Asn Ile Met His Asn Ser Lys Ala Pro Lys Lys
    595                 600                 605 aat agg ctg agg agg aag tct tct acc agg cat att cat gcg ctt gaa      1991
Asn Arg Leu Arg Arg Lys Ser Ser Thr Arg His Ile His Ala Leu Glu
610                 615                 620 cta gta gtc agt aga aat cta agc cca cct aat tgt act gaa ttg caa      2039
Leu Val Val Ser Arg Asn Leu Ser Pro Pro Asn Cys Thr Glu Leu Gln
625                 630                 635                 640 att gat agt tgt tct agc agt gaa gag ata aag aaa aaa aag tac aac      2087
Ile Asp Ser Cys Ser Ser Ser Glu Glu Ile Lys Lys Lys Lys Tyr Asn
            645                 650                 655 caa atg cca gtc agg cac agc aga aac cta caa ctc atg gaa ggt aaa      2135
Gln Met Pro Val Arg His Ser Arg Asn Leu Gln Leu Met Glu Gly Lys
        660                 665                 670 gaa cct gca act gga gcc aag aag agt aac aag cca aat gaa cag aca      2183
Glu Pro Ala Thr Gly Ala Lys Lys Ser Asn Lys Pro Asn Glu Gln Thr
    675                 680                 685 agt aaa aga cat gac agc gat act ttc cca gag ctg aag tta aca aat      2231
Ser Lys Arg His Asp Ser Asp Thr Phe Pro Glu Leu Lys Leu Thr Asn
690                 695                 700 gca cct ggt tct ttt act aag tgt tca aat acc agt gaa ctt aaa gaa      2279
Ala Pro Gly Ser Phe Thr Lys Cys Ser Asn Thr Ser Glu Leu Lys Glu
705                 710                 715                 720 ttt gtc aat cct agc ctt cca aga gaa gaa aaa gaa gag aaa cta gaa      2327
Phe Val Asn Pro Ser Leu Pro Arg Glu Glu Lys Glu Glu Lys Leu Glu
            725                 730                 735 aca gtt aaa gtg tct aat aat gct gaa gac ccc aaa gat ctc atg tta      2375
Thr Val Lys Val Ser Asn Asn Ala Glu Asp Pro Lys Asp Leu Met Leu
        740                 745                 750 agt gga gaa agg gtt ttg caa act gaa aga tct gta gag agt agc agt      2423
Ser Gly Glu Arg Val Leu Gln Thr Glu Arg Ser Val Glu Ser Ser Ser
    755                 760                 765 att tca ttg gta cct ggt act gat tat ggc act cag gaa agt atc tcg      2471
Ile Ser Leu Val Pro Gly Thr Asp Tyr Gly Thr Gln Glu Ser Ile Ser
770                 775                 780 tta ctg gaa gtt agc act cta ggg aag gca aaa aca gaa cca aat aaa      2519
Leu Leu Glu Val Ser Thr Leu Gly Lys Ala Lys Thr Glu Pro Asn Lys
785                 790                 795                 800 tgt gtg agt cag tgt gca gca ttt gaa aac ccc aag gga cta att cat      2567
Cys Val Ser Gln Cys Ala Ala Phe Glu Asn Pro Lys Gly Leu Ile His
```

-continued

| | | | | | | | | | | | | | | | |
|---|---|---|---|---|---|---|---|---|---|---|---|---|---|---|---|
| | | | | 805 | | | | 810 | | | | 815 | | | |
| ggt | tgt | tcc | aaa | gat | aat | aga | aat | gac | aca | gaa | ggc | ttt | aag | tat | cca | 2615 |
| Gly | Cys | Ser | Lys | Asp | Asn | Arg | Asn | Asp | Thr | Glu | Gly | Phe | Lys | Tyr | Pro |
| | | | 820 | | | | 825 | | | | | 830 | | | | ttg gga cat gaa gtt aac cac agt cgg gaa aca agc ata gaa atg gaa    2663
Leu Gly His Glu Val Asn His Ser Arg Glu Thr Ser Ile Glu Met Glu
        835                 840                 845 gaa agt gaa ctt gat gct cag tat ttg cag aat aca ttc aag gtt tca    2711
Glu Ser Glu Leu Asp Ala Gln Tyr Leu Gln Asn Thr Phe Lys Val Ser
850                 855                 860 aag cgc cag tca ttt gct ccg ttt tca aat cca gga aat gca gaa gag    2759
Lys Arg Gln Ser Phe Ala Pro Phe Ser Asn Pro Gly Asn Ala Glu Glu
865                 870                 875                 880 gaa tgt gca aca ttc tct gcc cac tct ggg tcc tta aag aaa caa agt    2807
Glu Cys Ala Thr Phe Ser Ala His Ser Gly Ser Leu Lys Lys Gln Ser
                885                 890                 895 cca aaa gtc act ttt gaa tgt gaa caa aag gaa gaa aat caa gga aag    2855
Pro Lys Val Thr Phe Glu Cys Glu Gln Lys Glu Glu Asn Gln Gly Lys
            900                 905                 910 aat gag tct aat atc aag cct gta cag aca gtt aat atc act gca ggc    2903
Asn Glu Ser Asn Ile Lys Pro Val Gln Thr Val Asn Ile Thr Ala Gly
        915                 920                 925 ttt cct gtg gtt ggt cag aaa gat aag cca gtt gat aat gcc aaa tgt    2951
Phe Pro Val Val Gly Gln Lys Asp Lys Pro Val Asp Asn Ala Lys Cys
930                 935                 940 agt atc aaa gga ggc tct agg ttt tgt cta tca tct cag ttc aga ggc    2999
Ser Ile Lys Gly Gly Ser Arg Phe Cys Leu Ser Ser Gln Phe Arg Gly
945                 950                 955                 960 aac gaa act gga ctc att act cca aat aaa cat gga ctt tta caa aac    3047
Asn Glu Thr Gly Leu Ile Thr Pro Asn Lys His Gly Leu Leu Gln Asn
                965                 970                 975 cca tat cgt ata cca cca ctt ttt ccc atc aag tca ttt gtt aaa act    3095
Pro Tyr Arg Ile Pro Pro Leu Phe Pro Ile Lys Ser Phe Val Lys Thr
            980                 985                 990 aaa tgt aag aaa aat ctg cta gag gaa aac ttt gag gaa cat tca atg    3143
Lys Cys Lys Lys Asn Leu Leu Glu Glu Asn Phe Glu Glu His Ser Met
        995                 1000                1005 tca cct gaa aga gaa atg gga aat gag aac att cca agt aca gtg agc    3191
Ser Pro Glu Arg Glu Met Gly Asn Glu Asn Ile Pro Ser Thr Val Ser
    1010                1015                1020 aca att agc cgt aat aac att aga gaa aat gtt ttt aaa gaa gcc agc    3239
Thr Ile Ser Arg Asn Asn Ile Arg Glu Asn Val Phe Lys Glu Ala Ser
1025                1030                1035                1040 tca agc aat att aat gaa gta ggt tcc agt act aat gaa gtg ggc tcc    3287
Ser Ser Asn Ile Asn Glu Val Gly Ser Ser Thr Asn Glu Val Gly Ser
                1045                1050                1055 agt att aat gaa ata ggt tcc agt gat gaa aac att caa gca gaa cta    3335
Ser Ile Asn Glu Ile Gly Ser Ser Asp Glu Asn Ile Gln Ala Glu Leu
            1060                1065                1070 ggt aga aac aga ggg cca aaa ttg aat gct atg ctt aga tta ggg gtt    3383
Gly Arg Asn Arg Gly Pro Lys Leu Asn Ala Met Leu Arg Leu Gly Val
        1075                1080                1085 ttg caa cct gag gtc tat aaa caa agt ctt cct gga agt aat tgt aag    3431
Leu Gln Pro Glu Val Tyr Lys Gln Ser Leu Pro Gly Ser Asn Cys Lys
    1090                1095                1100 cat cct gaa ata aaa aag caa gaa tat gaa gaa gta gtt cag act gtt    3479
His Pro Glu Ile Lys Lys Gln Glu Tyr Glu Glu Val Val Gln Thr Val
1105                1110                1115                1120 aat aca gat ttc tct cca tat ctg att tca gat aac tta gaa cag cct    3527

```
Asn Thr Asp Phe Ser Pro Tyr Leu Ile Ser Asp Asn Leu Glu Gln Pro
            1125                1130                1135 atg gga agt agt cat gca tct cag gtt tgt tct gag aca cct gat gac        3575
Met Gly Ser Ser His Ala Ser Gln Val Cys Ser Glu Thr Pro Asp Asp
        1140                1145                1150 ctg tta gat gat ggt gaa ata aag gaa gat act agt ttt gct gaa aat        3623
Leu Leu Asp Asp Gly Glu Ile Lys Glu Asp Thr Ser Phe Ala Glu Asn
        1155                1160                1165 gac att aag gaa agt tct gct gtt ttt agc aaa agc gtc cag aaa gga        3671
Asp Ile Lys Glu Ser Ser Ala Val Phe Ser Lys Ser Val Gln Lys Gly
        1170                1175                1180 gag ctt agc agg agt cct agc cct ttc acc cat aca cat ttg gct cag        3719
Glu Leu Ser Arg Ser Pro Ser Pro Phe Thr His Thr His Leu Ala Gln
1185                1190                1195                1200 ggt tac cga aga ggg gcc aag aaa tta gag tcc tca gaa gag aac tta        3767
Gly Tyr Arg Arg Gly Ala Lys Lys Leu Glu Ser Ser Glu Glu Asn Leu
        1205                1210                1215 tct agt gag gat gaa gag ctt ccc tgc ttc caa cac ttg tta ttt ggt        3815
Ser Ser Glu Asp Glu Glu Leu Pro Cys Phe Gln His Leu Leu Phe Gly
        1220                1225                1230 aaa gta aac aat ata cct tct cag tct act agg cat agc acc gtt gct        3863
Lys Val Asn Asn Ile Pro Ser Gln Ser Thr Arg His Ser Thr Val Ala
        1235                1240                1245 acc gag tgt ctg tct aag aac aca gag gag aat tta tta tca ttg aag        3911
Thr Glu Cys Leu Ser Lys Asn Thr Glu Glu Asn Leu Leu Ser Leu Lys
        1250                1255                1260 aat agc tta aat gac tgc agt aac cag gta ata ttg gca aag gca tct        3959
Asn Ser Leu Asn Asp Cys Ser Asn Gln Val Ile Leu Ala Lys Ala Ser
1265                1270                1275                1280 cag gaa cat cac ctt agt gag gaa aca aaa tgt tct gct agc ttg ttt        4007
Gln Glu His His Leu Ser Glu Glu Thr Lys Cys Ser Ala Ser Leu Phe
        1285                1290                1295 tct tca cag tgc agt gaa ttg gaa gac ttg act gca aat aca aac acc        4055
Ser Ser Gln Cys Ser Glu Leu Glu Asp Leu Thr Ala Asn Thr Asn Thr
        1300                1305                1310 cag gat cct ttc ttg att ggt tct tcc aaa caa atg agg cat cag tct        4103
Gln Asp Pro Phe Leu Ile Gly Ser Ser Lys Gln Met Arg His Gln Ser
        1315                1320                1325 gaa agc cag gga gtt ggt ctg agt gac aag gaa ttg gtt tca gat gat        4151
Glu Ser Gln Gly Val Gly Leu Ser Asp Lys Glu Leu Val Ser Asp Asp
        1330                1335                1340 gaa gaa aga gga acg ggc ttg gaa gaa aat aat caa gaa gag caa agc        4199
Glu Glu Arg Gly Thr Gly Leu Glu Glu Asn Asn Gln Glu Glu Gln Ser
1345                1350                1355                1360 atg gat tca aac tta ggt gaa gca gca tct ggg tgt gag agt gaa aca        4247
Met Asp Ser Asn Leu Gly Glu Ala Ala Ser Gly Cys Glu Ser Glu Thr
        1365                1370                1375 agc gtc tct gaa gac tgc tca ggg cta tcc tct cag agt gac att tta        4295
Ser Val Ser Glu Asp Cys Ser Gly Leu Ser Ser Gln Ser Asp Ile Leu
        1380                1385                1390 acc act cag cag agg gat acc atg caa cat aac ctg ata aag ctc cag        4343
Thr Thr Gln Gln Arg Asp Thr Met Gln His Asn Leu Ile Lys Leu Gln
        1395                1400                1405 cag gaa atg gct gaa cta gaa gct gtg tta gaa cag cat ggg agc cag        4391
Gln Glu Met Ala Glu Leu Glu Ala Val Leu Glu Gln His Gly Ser Gln
        1410                1415                1420 cct tct aac agc tac cct tcc atc ata agt gac tct tct gcc ctt gag        4439
Pro Ser Asn Ser Tyr Pro Ser Ile Ile Ser Asp Ser Ser Ala Leu Glu
1425                1430                1435                1440
```

-continued

| | | |
|---|---|---|
| gac ctg cga aat cca gaa caa agc aca tca gaa aaa gca gta tta act<br>Asp Leu Arg Asn Pro Glu Gln Ser Thr Ser Glu Lys Val Leu Gln Thr<br>                1445                        1450                        1455 | 4487 |
| tca cag aaa agt agt gaa tac cct ata agc cag aat cca gaa ggc ctt<br>Ser Gln Lys Ser Ser Glu Tyr Pro Ile Ser Gln Asn Pro Glu Gly Xaa<br>1460                        1465                        1470 | 4535 |
| tct gct gac aag ttt gag gtg tct gca gat agt tct acc agt aaa aat<br>Ser Ala Asp Lys Phe Glu Val Ser Ala Asp Ser Ser Thr Ser Lys Asn<br>                1475                        1480                        1485 | 4583 |
| aaa gaa cca gga gtg gaa agg tca tcc cct tct aaa tgc cca tca tta<br>Lys Glu Pro Gly Val Glu Arg Ser Ser Pro Ser Lys Cys Pro Ser Leu<br>1490                        1495                        1500 | 4631 |
| gat gat agg tgg tac atg cac agt tgc tct ggg agt ctt cag aat aga<br>Asp Asp Arg Trp Tyr Met His Ser Cys Ser Gly Ser Leu Gln Asn Arg<br>1505                        1510                        1515                        1520 | 4679 |
| aac tac cca tct caa gag gag ctc att aag gtt gtt gat gtg gag gag<br>Asn Tyr Pro Pro Gln Glu Glu Leu Ile Lys Val Val Asp Val Glu Glu<br>                1525                        1530                        1535 | 4727 |
| caa cag ctg gaa gag tct ggg cca cac gat ttg acg gaa aca tct tac<br>Gln Gln Leu Glu Glu Ser Gly Pro His Asp Leu Thr Glu Thr Ser Tyr<br>                      1540                        1545                        1550 | 4775 |
| ttg cca agg caa gat cta gag gga acc cct tac ctg gaa tct gga atc<br>Leu Pro Arg Gln Asp Leu Glu Gly Thr Pro Tyr Leu Glu Ser Gly Ile<br>                1555                        1560                        1565 | 4823 |
| agc ctc ttc tct gat gac cct gaa tct gat cct tct gaa gac aga gcc<br>Ser Leu Phe Ser Asp Asp Pro Glu Ser Asp Pro Ser Glu Asp Arg Ala<br>1570                        1575                        1580 | 4871 |
| cca gag tca gct cgt gtt ggc aac ata cca tct tca acc tct gca ttg<br>Pro Glu Ser Ala Arg Val Gly Asn Ile Pro Ser Ser Thr Ser Ala Leu<br>1585                        1590                        1595                        1600 | 4919 |
| aaa gtt ccc caa ttg aaa gtt gca gaa tct gcc cag agt cca gct gct<br>Lys Val Pro Gln Leu Lys Val Ala Glu Ser Ala Gln Ser Pro Ala Ala<br>                1605                        1610                        1615 | 4967 |
| gct cat act act gat act gct ggg tat aat gca atg gaa gaa agt gtg<br>Ala His Thr Thr Asp Thr Ala Gly Tyr Asn Ala Met Glu Glu Ser Val<br>                      1620                        1625                        1630 | 5015 |
| agc agg gag aag cca gaa ttg aca gct tca aca gaa agg gtc aac aaa<br>Ser Arg Glu Lys Pro Glu Leu Thr Ala Ser Thr Glu Arg Val Asn Lys<br>                1635                        1640                        1645 | 5063 |
| aga atg tcc atg gtg gtg tct ggc ctg acc cca gaa gaa ttt atg ctc<br>Arg Met Ser Met Val Val Ser Gly Leu Thr Pro Glu Glu Phe Met Leu<br>1650                        1655                        1660 | 5111 |
| gtg tac aag ttt gcc aga aaa cac cac atc act tta act aat cta att<br>Val Tyr Lys Phe Ala Arg Lys His His Ile Thr Leu Thr Asn Leu Ile<br>1665                        1670                        1675                        1680 | 5159 |
| act gaa gag act act cat gtt gtt atg aaa aca gat gct gag ttt gtg<br>Thr Glu Glu Thr Thr His Val Val Met Lys Thr Asp Ala Glu Phe Val<br>                      1685                        1690                        1695 | 5207 |
| tgt gaa cgg aca ctg aaa tat ttt cta gga att gcg gga gga aaa tgg<br>Cys Glu Arg Thr Leu Lys Tyr Phe Leu Gly Ile Ala Gly Gly Lys Trp<br>                1700                        1705                        1710 | 5255 |
| gta gtt agc tat ttc tgg gtg acc cag tct att aaa gaa aga aaa atg<br>Val Val Ser Tyr Phe Trp Val Thr Gln Ser Ile Lys Glu Arg Lys Met<br>1715                        1720                        1725 | 5303 |
| ctg aat gag cat gat ttt gaa gtc aga gga gat gtg gtc aat gga aga<br>Leu Asn Glu His Asp Phe Glu Val Arg Gly Asp Val Val Asn Gly Arg<br>                1730                        1735                        1740 | 5351 |
| aac cac caa ggt cca aag cga gca aga gaa tcc cag gac aga aag atc<br>Asn His Gln Gly Pro Lys Arg Ala Arg Glu Ser Gln Asp Arg Lys Ile<br>1745                        1750                        1755                        1760 | 5399 |

```
ttc agg ggg cta gaa atc tgt tgc tat ggg ccc ttc acc aac atg ccc    5447
Phe Arg Gly Leu Glu Ile Cys Cys Tyr Gly Pro Phe Thr Asn Met Pro
            1765                1770                1775 aca gat caa ctg gaa tgg atg gta cag ctg tgt ggt gct tct gtg gtg    5495
Thr Asp Gln Leu Glu Trp Met Val Gln Leu Cys Gly Ala Ser Val Val
            1780                1785                1790 aag gag ctt tca tca ttc acc ctt ggc aca ggt gtc cac cca att gtg    5543
Lys Glu Leu Ser Ser Phe Thr Leu Gly Thr Gly Val His Pro Ile Val
            1795                1800                1805 gtt gtg cag cca gat gcc tgg aca gag gac aat ggc ttc cat gca att    5591
Val Val Gln Pro Asp Ala Trp Thr Glu Asp Asn Gly Phe His Ala Ile
            1810                1815                1820 ggg cag atg tgt gag gca cct gtg gtg acc cga gag tgg gtg ttg gac    5639
Gly Gln Met Cys Glu Ala Pro Val Val Thr Arg Glu Trp Val Leu Asp
1825                1830                1835                1840 agt gta gca ctc tac cag tgc cag gag ctg gac acc tac ctg ata ccc    5687
Ser Val Ala Leu Tyr Gln Cys Gln Glu Leu Asp Thr Tyr Leu Ile Pro
            1845                1850                1855 cag atc ccc cac agc cac tac tgat                                   5712
Gln Ile Pro His Ser His Tyr
            1860

(2) INFORMATION FOR SEQ ID NO:2:

(i) SEQUENCE CHARACTERISTICS:
        (A) LENGTH: 1863
        (B) TYPE: amino acid
        (C) STRANDEDNESS: single
        (D) TOPOLOGY: unknown (x) PUBLICATION INFORMATION:
        (A) AUTHORS: Miki, Y., et. al.
        (B) TITLE: A strong candidate gene for the breast and
            ovarian cancer susceptibility gene
            BRCA1.
        (C) JOURNAL: Science
        (D) VOLUME: 266
        (E) PAGES: 66-71
        (F) DATE: 1994
        (K) RELEVANT RESIDUES IN SEQ ID NO:2:  granin box domain
            at amino acids 1214-1223

(xi) SEQUENCE DESCRIPTION: SEQ ID NO:2:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
            85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140
```

-continued

```
Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Asp Arg Val His
        435                 440                 445

Ser Lys Ser Val Glu Ser Asp Ile Glu Asp Lys Ile Phe Gly Lys Thr
    450                 455                 460

Tyr Arg Lys Lys Ala Ser Leu Pro Asn Leu Ser His Val Thr Glu Asn
465                 470                 475                 480

Leu Ile Ile Gly Ala Phe Val Ser Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
    530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
```

-continued

```
                565                 570                 575
Glu Ser Ala Phe Lys Thr Lys Ala Glu Pro Ile Ser Ser Ser Ile Ser
            580                 585                 590
Asn Glu Leu Glu Leu Asn Ile Met His Asn Ser Lys Ala Pro Lys Lys
        595                 600                 605
Asn Arg Leu Arg Arg Lys Ser Ser Thr Arg His Ile His Ala Leu Glu
    610                 615                 620
Leu Val Val Ser Arg Asn Leu Ser Pro Pro Asn Cys Thr Glu Leu Gln
625                 630                 635                 640
Ile Asp Ser Cys Ser Ser Ser Glu Glu Ile Lys Lys Lys Tyr Asn
                645                 650                 655
Gln Met Pro Val Arg His Ser Arg Asn Leu Gln Leu Met Glu Gly Lys
            660                 665                 670
Glu Pro Ala Thr Gly Ala Lys Lys Ser Asn Lys Pro Asn Glu Gln Thr
        675                 680                 685
Ser Lys Arg His Asp Ser Asp Thr Phe Pro Glu Leu Lys Leu Thr Asn
    690                 695                 700
Ala Pro Gly Ser Phe Thr Lys Cys Ser Asn Thr Ser Glu Leu Lys Glu
705                 710                 715                 720
Phe Val Asn Pro Ser Leu Pro Arg Glu Glu Lys Glu Glu Lys Leu Glu
                725                 730                 735
Thr Val Lys Val Ser Asn Asn Ala Glu Asp Pro Lys Asp Leu Met Leu
            740                 745                 750
Ser Gly Glu Arg Val Leu Gln Thr Glu Arg Ser Val Glu Ser Ser Ser
        755                 760                 765
Ile Ser Leu Val Pro Gly Thr Asp Tyr Gly Thr Gln Glu Ser Ile Ser
    770                 775                 780
Leu Leu Glu Val Ser Thr Leu Gly Lys Ala Lys Thr Glu Pro Asn Lys
785                 790                 795                 800
Cys Val Ser Gln Cys Ala Ala Phe Glu Asn Pro Lys Gly Leu Ile His
                805                 810                 815
Gly Cys Ser Lys Asp Asn Arg Asn Asp Thr Glu Gly Phe Lys Tyr Pro
            820                 825                 830
Leu Gly His Glu Val Asn His Ser Arg Glu Thr Ser Ile Glu Met Glu
        835                 840                 845
Glu Ser Glu Leu Asp Ala Gln Tyr Leu Gln Asn Thr Phe Lys Val Ser
    850                 855                 860
Lys Arg Gln Ser Phe Ala Pro Phe Ser Asn Pro Gly Asn Ala Glu Glu
865                 870                 875                 880
Glu Cys Ala Thr Phe Ser Ala His Ser Gly Ser Leu Lys Lys Gln Ser
                885                 890                 895
Pro Lys Val Thr Phe Glu Cys Glu Gln Lys Glu Glu Asn Gln Gly Lys
            900                 905                 910
Asn Glu Ser Asn Ile Lys Pro Val Gln Thr Val Asn Ile Thr Ala Gly
        915                 920                 925
Phe Pro Val Val Gly Gln Lys Asp Lys Pro Val Asp Asn Ala Lys Cys
    930                 935                 940
Ser Ile Lys Gly Gly Ser Arg Phe Cys Leu Ser Ser Gln Phe Arg Gly
945                 950                 955                 960
Asn Glu Thr Gly Leu Ile Thr Pro Asn Lys His Gly Leu Leu Gln Asn
                965                 970                 975
Pro Tyr Arg Ile Pro Pro Leu Phe Pro Ile Lys Ser Phe Val Lys Thr
            980                 985                 990
```

-continued

```
Lys Cys Lys Lys Asn Leu Leu Glu Glu Asn Phe Glu Glu His Ser Met
        995                 1000                1005
Ser Pro Glu Arg Glu Met Gly Asn Glu Asn Ile Pro Ser Thr Val Ser
        1010                1015                1020
Thr Ile Ser Arg Asn Asn Ile Arg Glu Asn Val Phe Lys Glu Ala Ser
1025                1030                1035                1040
Ser Ser Asn Ile Asn Glu Val Gly Ser Ser Thr Asn Glu Val Gly Ser
                1045                1050                1055
Ser Ile Asn Glu Ile Gly Ser Ser Asp Glu Asn Ile Gln Ala Glu Leu
                1060                1065                1070
Gly Arg Asn Arg Gly Pro Lys Leu Asn Ala Met Leu Arg Leu Gly Val
                1075                1080                1085
Leu Gln Pro Glu Val Tyr Lys Gln Ser Leu Pro Gly Ser Asn Cys Lys
        1090                1095                1100
His Pro Glu Ile Lys Lys Gln Gly Tyr Glu Val Val Gln Thr Val
1105                1110                1115                1120
Asn Thr Asp Phe Ser Pro Tyr Leu Ile Ser Asp Asn Leu Glu Gln Pro
                1125                1130                1135
Met Gly Ser Ser His Ala Ser Gln Val Cys Ser Glu Thr Pro Asp Asp
                1140                1145                1150
Leu Leu Asp Asp Gly Glu Ile Lys Glu Asp Thr Ser Phe Ala Glu Asn
        1155                1160                1165
Asp Ile Lys Glu Ser Ser Ala Val Phe Ser Lys Ser Val Gln Lys Gly
        1170                1175                1180
Glu Leu Ser Arg Ser Pro Ser Pro Phe Thr His Thr His Leu Ala Gln
1185                1190                1195                1200
Gly Tyr Arg Arg Gly Ala Lys Lys Leu Glu Ser Ser Glu Glu Asn Leu
                1205                1210                1215
Ser Ser Glu Asp Glu Glu Leu Pro Cys Phe Gln His Leu Leu Phe Gly
                1220                1225                1230
Lys Val Asn Asn Ile Pro Ser Gln Ser Thr Arg His Ser Thr Val Ala
        1235                1240                1245
Thr Glu Cys Leu Ser Lys Asn Thr Glu Glu Asn Leu Leu Ser Leu Lys
        1250                1255                1260
Asn Ser Leu Asn Asp Cys Ser Asn Gln Val Ile Leu Ala Lys Ala Ser
1265                1270                1275                1280
Gln Glu His His Leu Ser Glu Glu Thr Lys Cys Ser Ala Ser Leu Phe
                1285                1290                1295
Ser Ser Gln Cys Ser Glu Leu Glu Asp Leu Thr Ala Asn Thr Asn Thr
                1300                1305                1310
Gln Asp Pro Phe Leu Ile Gly Ser Ser Lys Gln Met Arg His Gln Ser
                1315                1320                1325
Glu Ser Gln Gly Val Gly Leu Ser Asp Lys Glu Leu Val Ser Asp Asp
        1330                1335                1340
Glu Glu Arg Gly Thr Gly Leu Glu Glu Asn Asn Gln Glu Glu Gln Ser
1345                1350                1355                1360
Met Asp Ser Asn Leu Gly Glu Ala Ala Ser Gly Cys Glu Ser Glu Thr
                1365                1370                1375
Ser Val Ser Glu Asp Cys Ser Gly Leu Ser Ser Gln Ser Asp Ile Leu
                1380                1385                1390
Thr Thr Gln Gln Arg Asp Thr Met Gln His Asn Leu Ile Lys Leu Gln
                1395                1400                1405
```

-continued

```
Gln Glu Met Ala Glu Leu Glu Ala Val Leu Glu Gln His Gly Ser Gln
    1410                1415                1420
Pro Ser Asn Ser Tyr Pro Ser Ile Ile Ser Asp Ser Ser Ala Leu Glu
1425            1430                1435                1440
Asp Leu Arg Asn Pro Glu Gln Ser Thr Ser Glu Lys Val Leu Gln Thr
                1445                1450                1455
Ser Gln Lys Ser Ser Glu Tyr Pro Ile Ser Gln Asn Pro Glu Gly Xaa
            1460                1465                1470
Ser Ala Asp Lys Phe Glu Val Ser Ala Asp Ser Ser Thr Ser Lys Asn
        1475                1480                1485
Lys Glu Pro Gly Val Glu Arg Ser Ser Pro Ser Lys Cys Pro Ser Leu
    1490                1495                1500
Asp Asp Arg Trp Tyr Met His Ser Cys Ser Gly Ser Leu Gln Asn Arg
1505                1510                1515                1520
Asn Tyr Pro Pro Gln Glu Glu Leu Ile Lys Val Val Asp Val Glu Glu
                1525                1530                1535
Gln Gln Leu Glu Glu Ser Gly Pro His Asp Leu Thr Glu Thr Ser Tyr
                1540                1545                1550
Leu Pro Arg Gln Asp Leu Glu Gly Thr Pro Tyr Leu Glu Ser Gly Ile
            1555                1560                1565
Ser Leu Phe Ser Asp Asp Pro Glu Ser Asp Pro Ser Glu Asp Arg Ala
        1570                1575                1580
Pro Glu Ser Ala Arg Val Gly Asn Ile Pro Ser Ser Thr Ser Ala Leu
1585                1590                1595                1600
Lys Val Pro Gln Leu Lys Val Ala Glu Ser Ala Gln Ser Pro Ala Ala
                1605                1610                1615
Ala His Thr Thr Asp Thr Ala Gly Tyr Asn Ala Met Glu Glu Ser Val
            1620                1625                1630
Ser Arg Glu Lys Pro Glu Leu Thr Ala Ser Thr Glu Arg Val Asn Lys
        1635                1640                1645
Arg Met Ser Met Val Val Ser Gly Leu Thr Pro Glu Glu Phe Met Leu
    1650                1655                1660
Val Tyr Lys Phe Ala Arg Lys His His Ile Thr Leu Thr Asn Leu Ile
1665                1670                1675                1680
Thr Glu Glu Thr Thr His Val Val Met Lys Thr Asp Ala Glu Phe Val
                1685                1690                1695
Cys Glu Arg Thr Leu Lys Tyr Phe Leu Gly Ile Ala Gly Gly Lys Trp
            1700                1705                1710
Val Val Ser Tyr Phe Trp Val Thr Gln Ser Ile Lys Glu Arg Lys Met
        1715                1720                1725
Leu Asn Glu His Asp Phe Glu Val Arg Gly Asp Val Val Asn Gly Arg
    1730                1735                1740
Asn His Gln Gly Pro Lys Arg Ala Arg Glu Ser Gln Asp Arg Lys Ile
1745                1750                1755                1760
Phe Arg Gly Leu Glu Ile Cys Cys Tyr Gly Pro Phe Thr Asn Met Pro
                1765                1770                1775
Thr Asp Gln Leu Glu Trp Met Val Gln Leu Cys Gly Ala Ser Val Val
            1780                1785                1790
Lys Glu Leu Ser Ser Phe Thr Leu Gly Thr Gly Val His Pro Ile Val
        1795                1800                1805
Val Val Gln Pro Asp Ala Trp Thr Glu Asp Asn Gly Phe His Ala Ile
    1810                1815                1820
Gly Gln Met Cys Glu Ala Pro Val Val Thr Arg Glu Trp Val Leu Asp
```

```
1825                1830                1835                1840
Ser Val Ala Leu Tyr Gln Cys Gln Glu Leu Asp Thr Tyr Leu Ile Pro
                1845                1850                1855
Gln Ile Pro His Ser His Tyr
        1860
```

(2) INFORMATION FOR SEQ ID NO:3:

(i) SEQUENCE CHARACTERISTICS:
        (A) LENGTH: 11283
        (B) TYPE: nucleic acid
        (C) STRANDEDNESS: double
        (D) TOPOLOGY: linear (ix) FEATURE:
        (A) NAME/KEY: BRCA2

(x) PUBLICATION INFORMATION:
        (A) AUTHORS:    Wooster, R. et al.
        (B) TITLE:  Identification of the breast cancer
            susceptability gene BRCA2
        (C) JOURNAL:    Nature
        (D) VOLUME:     379
        (E) PAGES:      789-792
        (F) DATE:       1995

(xi) SEQUENCE DESCRIPTION: SEQ ID NO:3:

```
ggcggagccg ctgtggcact gctgcgcctc tgctgcgcct cgggtgtctt ttgcggcggt    60
gggtcgccgc cgggagaagc gtgaggggac agatttgtga ccggcgcggt ttttgtcagc   120
ttactccggc caaaaaagaa ctgcacctct ggagcggact tatttaccaa gcattggagg   180
aatatcgtag gtaaaa                                                  196 atg cct att gga tcc aaa gag agg cca aca ttt ttt gaa att ttt aag    244
Met Pro Ile Gly Ser Lys Glu Arg Pro Thr Phe Phe Glu Ile Phe Lys
 1               5                  10                  15 aca cgc tgc aac aaa gca gat tta gga cca ata agt ctt aat tgg ttt    292
Thr Arg Cys Asn Lys Ala Asp Leu Gly Pro Ile Ser Leu Asn Trp Phe
         20                  25                  30 gaa gaa ctt tct tca gaa gct cca ccc tat aat tct gaa cct gca gaa    340
Glu Glu Leu Ser Ser Glu Ala Pro Pro Tyr Asn Ser Glu Pro Ala Glu
 35                  40                  45 gaa tct gaa cat aaa aac aac aat tac gaa cca aac cta ttt aaa act    388
Glu Ser Glu His Lys Asn Asn Asn Tyr Glu Pro Asn Leu Phe Lys Thr
 50                  55                  60 cca caa agg aaa cca tct tat aat cag ctg gct tca act cca ata ata    436
Pro Gln Arg Lys Pro Ser Tyr Asn Gln Leu Ala Ser Thr Pro Ile Ile
 65              70                  75                  80 ttc aaa gag caa ggg ctg act ctg ccg ctg tac caa tct cct gta aaa    484
Phe Lys Glu Gln Gly Leu Thr Leu Pro Leu Tyr Gln Ser Pro Val Lys
 85                  90                  95 gaa tta gat aaa ttc aaa tta gac tta gga agg aat gtt ccc aat agt    532
Glu Leu Asp Lys Phe Lys Leu Asp Leu Gly Arg Asn Val Pro Asn Ser
100                 105                 110 aga cat aaa agt ctt cgc aca gtg aaa act aaa atg gat caa gca gat    580
Arg His Lys Ser Leu Arg Thr Val Lys Tyr Lys Met Asp Gln Ala Asp
115                 120                 125 gat gtt tcc tgt cca ctt cta aat tct tgt ctt agt gaa agt cct gtt    628
Asp Val Ser Cys Pro Leu Leu Asn Ser Cys Leu Ser Glu Ser Pro Val
130                 135                 140 gtt cta caa tgt aca cat gta aca cca caa aga gat aag tca gtg gta    676
Val Leu Gln Cys Thr His Val Thr Pro Gln Arg Asp Lys Ser Val Val
145                 150                 155                 160
```

```
tgt ggg agt ttg ttt cat aca cca aag ttt gtg aag ggt cgt cag aca         724
Cys Gly Ser Leu Phe His Thr Pro Lys Phe Val Lys Gly Arg Gln Thr
165                 170                 175 cca aaa cat att tct gaa agt cta gga gct gag gtg gat cct gat atg         772
Pro Lys His Ile Ser Glu Ser Leu Gly Ala Glu Val Asp Pro Asp Met
    180                 185                 190 tct tgg tca agt tct tta gct aca cca ccc acc ctt agt tct act gtg         820
Ser Trp Ser Ser Ser Leu Ala Thr Pro Pro Thr Leu Ser Ser Thr Val
195                 200                 205 ctc ata gtc aga aat gaa gaa gca tct gaa act gta ttt cct cat gat         868
Leu Ile Val Arg Asn Glu Glu Ala Ser Glu Thr Val Phe Pro His Asp
210                 215                 220 act act gct aat gtg aaa agc tat ttt tcc aat cat gat gaa agt ctg         916
Thr Thr Ala Asn Val Lys Ser Tyr Phe Ser Asn His Asp Glu Ser Leu
225                 230                 235                 240 aag aaa aat gat aga ttt atc gct tct gtg aca gac agt gaa aac aca         964
Lys Lys Asn Asp Arg Phe Ile Ala Ser Val Thr Asp Ser Glu Asn Thr
    245                 250                 255 aat caa aga gaa gct gca agt cat gga ttt gga aaa aca tca ggg aat        1012
Asn Gln Arg Glu Ala Ala Ser His Gly Phe Gly Lys Thr Ser Gly Asn
260                 265                 270 tca ttt aaa gta aat agc tgc aaa gac cac att gga aag tca atg cca        1060
Ser Phe Lys Val Asn Ser Cys Lys Asp His Ile Gly Lys Ser Met Pro
275                 280                 285 aat gtc cta gaa gat gaa gta tat gaa aca gtt gta gat acc tct gaa        1108
Asn Val Leu Glu Asp Glu Val Tyr Glu Thr Val Val Asp Thr Ser Glu
290                 295                 300 gaa gat agt ttt tca tta tgt ttt tct aaa tgt aga aca aaa aat cta        1156
Glu Asp Ser Phe Ser Leu Cys Phe Ser Lys Cys Arg Thr Lys Asn Leu
305                 310                 315                 320 caa aaa gta aga act agc aag act agg aaa aaa att ttc cat gaa gca        1204
Gln Lys Val Arg Thr Ser Lys Thr Arg Lys Lys Ile Phe His Glu Ala
325                 330                 335 aac gct gat gaa tgt gaa aaa tct aaa aac caa gtg aaa gaa aaa tac        1252
Asn Ala Asp Glu Cys Glu Lys Ser Lys Asn Gln Val Lys Glu Lys Tyr
340                 345                 350 tca ttt gta tct gaa gtg gaa cca aat gat act gat cca tta gat tca        1300
Ser Phe Val Ser Glu Val Glu Pro Asn Asp Thr Asp Pro Leu Asp Ser
355                 360                 365 aat gta gca cat cag aag ccc ttt gag agt gga agt gac aaa atc tcc        1348
Asn Val Ala His Gln Lys Pro Phe Glu Ser Gly Ser Asp Lys Ile Ser
370                 375                 380 aag gaa gtt gta ccg tct ttg gcc tgt gaa tgg tct caa cta acc ctt        1396
Lys Glu Val Val Pro Ser Leu Ala Cys Glu Trp Ser Gln Leu Thr Leu
385                 390                 395                 400 tca ggt cta aat gga gcc cag atg gag aaa ata ccc cta ttg cat att        1444
Ser Gly Leu Asn Gly Ala Gln Met Glu Lys Ile Pro Leu Leu His Ile
405                 410                 415 tct tca tgt gac caa aat att tca gaa aaa gac cta tta gac aca gag        1492
Ser Ser Cys Asp Gln Asn Ile Ser Glu Lys Asp Leu Leu Asp Thr Glu
420                 425                 430 aac aaa aga aag aaa gat ttt ctt act tca gag aat tct ttg cca cgt        1540
Asn Lys Arg Lys Lys Asp Phe Leu Thr Ser Glu Asn Ser Leu Pro Arg
435                 440                 445 att tct agc cta cca aaa tca gag aag cca tta aat gag gaa aca gtg        1588
Ile Ser Ser Leu Pro Lys Ser Glu Lys Pro Leu Asn Glu Glu Thr Val
450                 455                 460 gta aat aag aga gat gaa gag cag cat ctt gaa tct cat aca gac tgc        1636
Val Asn Lys Arg Asp Glu Glu Gln His Leu Glu Ser His Thr Asp Cys
465                 470                 475                 480
```

```
att ctt gca gta aag cag gca ata tct gga act tct cca gtg gct tct    1684
Ile Leu Ala Val Lys Gln Ala Ile Ser Gly Thr Ser Pro Val Ala Ser
485                 490                 495 tca ttt cag ggt atc aaa aag tct ata ttc aga ata aga gaa tca cct    1732
Ser Phe Gln Gly Ile Lys Lys Ser Ile Phe Arg Ile Arg Glu Ser Pro
500                 505                 510 aaa gag act ttc aat gca agt ttt tca ggt cat atg act gat cca aac    1780
Lys Glu Thr Phe Asn Ala Ser Phe Ser Gly His Met Thr Asp Pro Asn
515                 520                 525 ttt aaa aaa gaa act gaa gcc tct gaa agt gga ctg gaa ata cat act    1828
Phe Lys Lys Glu Thr Glu Ala Ser Glu Ser Gly Leu Glu Ile His Thr
530                 535                 540 gtt tgc tca cag aag gag gac tcc tta tgt cca aat tta att gat aat    1876
Val Cys Ser Gln Lys Glu Asp Ser Leu Cys Pro Asn Leu Ile Asp Asn
545                 550                 555                 560 gga agc tgg cca gcc acc acc aca cag aat tct gta gct ttg aag aat    1924
Gly Ser Trp Pro Ala Thr Thr Thr Gln Asn Ser Val Ala Leu Lys Asn
565                 570                 575 gca ggt tta ata tcc act ttg aaa aag aaa aca aat aag ttt att tat    1972
Ala Gly Leu Ile Ser Thr Leu Lys Lys Lys Thr Asn Lys Phe Ile Tyr
580                 585                 590 gct ata cat gat gaa aca ttt tat aaa gga aaa aaa ata ccg aaa gac    2020
Ala Ile His Asp Glu Thr Phe Tyr Lys Gly Lys Lys Ile Pro Lys Asp
595                 600                 605 caa aaa tca gaa cta att aac tgt tca gcc cag ttt gaa gca aat gct    2068
Gln Lys Ser Glu Leu Ile Asn Cys Ser Ala Gln Phe Glu Ala Asn Ala
610                 615                 620 ttt gaa gca cca ctt aca ttt gca aat gct gat tca ggt tta ttg cat    2116
Phe Glu Ala Pro Leu Thr Phe Ala Asn Ala Asp Ser Gly Leu Leu His
625                 630                 635                 640 tct tct gtg aaa aga agc tgt tca cag aat gat tct gaa gaa cca act    2164
Ser Ser Val Lys Arg Ser Cys Ser Gln Asn Asp Ser Glu Glu Pro Thr
645                 650                 655 ttg tcc tta act agc tct ttt ggg aca att ctg agg aaa tgt tct aga    2212
Leu Ser Leu Thr Ser Ser Phe Gly Thr Ile Leu Arg Lys Cys Ser Arg
660                 665                 670 aat gaa aca tgt tct aat aat aca gta atc tct cag gat ctt gat tat    2260
Asn Glu Thr Cys Ser Asn Asn Thr Val Ile Ser Gln Asp Leu Asp Tyr
675                 680                 685 aaa gaa gca aaa tgt aat aag gaa aaa cta cag tta ttt att acc cca    2308
Lys Glu Ala Lys Cys Asn Lys Glu Lys Leu Gln Leu Phe Ile Thr Pro
690                 695                 700 gaa gct gat tct ctg tca tgc ctg cag gaa gga cag tgt gaa aat gat    2356
Glu Ala Asp Ser Leu Ser Cys Leu Gln Glu Gly Gln Cys Glu Asn Asp
705                 710                 715                 720 cca aaa agc aaa aaa gtt tca gat ata aaa gaa gag gtc ttg gct gca    2404
Pro Lys Ser Lys Lys Val Ser Asp Ile Lys Glu Glu Val Leu Ala Ala
725                 730                 735 gca tgt cac cca gta caa cat tca aaa gtg gaa tac agt gat act gac    2452
Ala Cys His Pro Val Gln His Ser Lys Val Glu Tyr Ser Asp Thr Asp
740                 745                 750 ttt caa tcc cag aaa agt ctt tta tat gat cat gaa aat gcc agc act    2500
Phe Gln Ser Gln Lys Ser Leu Leu Tyr Asp His Glu Asn Ala Ser Thr
755                 760                 765 ctt att tta act cct act tcc aag gat gtt ctg tca aac cta gtc atg    2548
Leu Ile Leu Thr Pro Thr Ser Lys Asp Val Leu Ser Asn Leu Val Met
770                 775                 780 att tct aga ggc aaa gaa tca tac aaa atg tca gac aag ctc aaa ggt    2596
Ile Ser Arg Gly Lys Glu Ser Tyr Lys Met Ser Asp Lys Leu Lys Gly
```

-continued

| | | | | |
|---|---|---|---|---|
| | 785 | 790 | 795 | 800 |
| aac aat tat gaa tct gat gtt gaa tta acc aaa aat att ccc atg gaa<br>Asn Asn Tyr Glu Ser Asp Val Glu Leu Thr Lys Asn Ile Pro Met Glu<br>805                         810                        815 | | | | 2644 |

```
                785                 790                 795                 800
aac aat tat gaa tct gat gtt gaa tta acc aaa aat att ccc atg gaa        2644
Asn Asn Tyr Glu Ser Asp Val Glu Leu Thr Lys Asn Ile Pro Met Glu
805                 810                 815 aag aat caa gat gta tgt gct tta aat gaa aat tat aaa aac gtt gag        2692
Lys Asn Gln Asp Val Cys Ala Leu Asn Glu Asn Tyr Lys Asn Val Glu
820                 825                 830 ctg ttg cca cct gaa aaa tac atg aga gta gca tca cct tca aga aag        2740
Leu Leu Pro Pro Glu Lys Tyr Met Arg Val Ala Ser Pro Ser Arg Lys
835                 840                 845 gta caa ttc aac caa aac aca aat cta aga gta atc caa aaa aat caa        2788
Val Gln Phe Asn Gln Asn Thr Asn Leu Arg Val Ile Gln Lys Asn Gln
850                 855                 860 gaa gaa act act tca att tca aaa ata act gtc aat cca gac tct gaa        2836
Glu Glu Thr Thr Ser Ile Ser Lys Ile Thr Val Asn Pro Asp Ser Glu
865                 870                 875                 880 gaa ctt ttc tca gac aat gag aat aat ttt gtc ttc caa gta gct aat        2884
Glu Leu Phe Ser Asp Asn Glu Asn Asn Phe Val Phe Gln Val Ala Asn
885                 890                 895 gaa agg aat aat ctt gct tta gga aat act aag gaa ctt cat gaa aca        2932
Glu Arg Asn Asn Leu Ala Leu Gly Asn Thr Lys Glu Leu His Glu Thr
900                 905                 910 gac ttg act tgt gta aac gaa ccc att ttc aag aac tct acc atg gtt        2980
Asp Leu Thr Cys Val Asn Glu Pro Ile Phe Lys Asn Ser Thr Met Val
915                 920                 925 tta tat gga gac aca ggt gat aaa caa gca acc caa gtg tca att aaa        3028
Leu Tyr Gly Asp Thr Gly Asp Lys Gln Ala Thr Gln Val Ser Ile Lys
930                 935                 940 aaa gat ttg gtt tat gtt ctt gca gag gag aac aaa aat agt gta aag        3076
Lys Asp Leu Val Tyr Val Leu Ala Glu Glu Asn Lys Asn Ser Val Lys
945                 950                 955                 960 cag cat ata aaa atg act cta ggt caa gat tta aaa tcg gac atc tcc        3124
Gln His Ile Lys Met Thr Leu Gly Gln Asp Leu Lys Ser Asp Ile Ser
965                 970                 975 ttg aat ata gat aaa ata cca gaa aaa aat aat gat tac atg aac aaa        3172
Leu Asn Ile Asp Lys Ile Pro Glu Lys Asn Asn Asp Tyr Met Asn Lys
980                 985                 990 tgg gca gga ctc tta ggt cca att tca aat cac agt ttt gga ggt agc        3220
Trp Ala Gly Leu Leu Gly Pro Ile Ser Asn His Ser Phe Gly Gly Ser
995                 1000                1005 ttc aga aca gct tca aat aag gaa atc aag ctc tct gaa cat aac att        3268
Phe Arg Thr Ala Ser Asn Lys Glu Ile Lys Leu Ser Glu His Asn Ile
1010                1015                1020 aag aag agc aaa atg ttc ttc aaa gat att gaa gaa caa tat cct act        3316
Lys Lys Ser Lys Met Phe Phe Lys Asp Ile Glu Glu Gln Tyr Pro Thr
1025                1030                1035                1040 agt tta gct tgt gtt gaa att gta aat acc ttg gca tta gat aat caa        3364
Ser Leu Ala Cys Val Glu Ile Val Asn Thr Leu Ala Leu Asp Asn Gln
1045                1050                1055 aag aaa ctg agc aag cct cag tca att aat act gta tct gca cat tta        3412
Lys Lys Leu Ser Lys Pro Gln Ser Ile Asn Thr Val Ser Ala His Leu
1060                1065                1070 cag agt agt gta gtt gtt tct gat tgt aaa aat agt cat ata acc cct        3460
Gln Ser Ser Val Val Val Ser Asp Cys Lys Asn Ser His Ile Thr Pro
1075                1080                1085 cag atg tta ttt tcc aag cag gat ttt aat tca aac cat aat tta aca        3508
Gln Met Leu Phe Ser Lys Gln Asp Phe Asn Ser Asn His Asn Leu Thr
1090                1095                1100 cct agc caa aag gca gaa att aca gaa ctt tct act ata tta gaa gaa        3556
```

```
Pro Ser Gln Lys Ala Glu Ile Thr Glu Leu Ser Thr Ile Leu Glu Glu
1105                1110                1115                1120 tca gga agt cag ttt gaa ttt act cag ttt aga aaa cca agc tac ata        3604
Ser Gly Ser Gln Phe Glu Phe Thr Gln Phe Arg Lys Pro Ser Tyr Ile
1125                1130                1135 ttg cag aag agt aca ttt gaa gtg cct gaa aac cag atg act atc tta        3652
Leu Gln Lys Ser Thr Phe Glu Val Pro Glu Asn Gln Met Thr Ile Leu
1140                1145                1150 aag acc act tct gag gaa tgc aga gat gct gat ctt cat gtc ata atg        3700
Lys Thr Thr Ser Glu Glu Cys Arg Asp Ala Asp Leu His Val Ile Met
1155                1160                1165 aat gcc cca tcg att ggt cag gta gac agc agc aag caa ttt gaa ggt        3748
Asn Ala Pro Ser Ile Gly Gln Val Asp Ser Ser Lys Gln Phe Glu Gly
1170                1175                1180 aca gtt gaa att aaa cgg aag ttt gct ggc ctg ttg aaa aat gac tgt        3796
Thr Val Glu Ile Lys Arg Lys Phe Ala Gly Leu Leu Lys Asn Asp Cys
1185                1190                1195                1200 aac aaa agt gct tct ggt tat tta aca gat gaa aat gaa gtg ggg ttt        3844
Asn Lys Ser Ala Ser Gly Tyr Leu Thr Asp Glu Asn Glu Val Gly Phe
1205                1210                1215 agg ggc ttt tat tct gct cat ggc aca aaa ctg aat gtt tct act gaa        3892
Arg Gly Phe Tyr Ser Ala His Gly Thr Lys Leu Asn Val Ser Thr Glu
1220                1225                1230 gct ctg caa aaa gct gtg aaa ctg ttt agt gat att gag aat att agt        3940
Ala Leu Gln Lys Ala Val Lys Leu Phe Ser Asp Ile Glu Asn Ile Ser
1235                1240                1245 gag gaa act tct gca gag gta cat cca ata agt tta tct tca agt aaa        3988
Glu Glu Thr Ser Ala Glu Val His Pro Ile Ser Leu Ser Ser Ser Lys
1250                1255                1260 tgt cat gat tct gtt gtt tca atg ttt aag ata gaa aat cat aat gat        4036
Cys His Asp Ser Val Val Ser Met Phe Lys Ile Glu Asn His Asn Asp
1265                1270                1275                1280 aaa act gta agt gaa aaa aat aat aaa tgc caa ctg ata tta caa aat        4084
Lys Thr Val Ser Glu Lys Asn Asn Lys Cys Gln Leu Ile Leu Gln Asn
1285                1290                1295 aat att gaa atg act act ggc act ttt gtt gaa gaa att act gaa aat        4132
Asn Ile Glu Met Thr Thr Gly Thr Phe Val Glu Glu Ile Thr Glu Asn
1300                1305                1310 tac aag aga aat act gaa aat gaa gat aac aaa tat act gct gcc agt        4180
Tyr Lys Arg Asn Thr Glu Asn Glu Asp Asn Lys Tyr Thr Ala Ala Ser
1315                1320                1325 aga aat tct cat aac tta gaa ttt gat ggc agt gat tca agt aaa aat        4228
Arg Asn Ser His Asn Leu Glu Phe Asp Gly Ser Asp Ser Ser Lys Asn
1330                1335                1340 gat act gtt tgt att cat aaa gat gaa acg gac ttg cta ttt act gat        4276
Asp Thr Val Cys Ile His Lys Asp Glu Thr Asp Leu Leu Phe Thr Asp
1345                1350                1355                1360 cag cac aac ata tgt ctt aaa tta tct ggc cag ttt atg aag gag gga        4324
Gln His Asn Ile Cys Leu Lys Leu Ser Gly Gln Phe Met Lys Glu Gly
1365                1370                1375 aac act cag att aaa gaa gat ttg tca gat tta act ttt ctg gaa gtt        4372
Asn Thr Gln Ile Lys Glu Asp Leu Ser Asp Leu Thr Phe Leu Glu Val
1380                1385                1390 gcg aaa gct caa gaa gca tgt cat ggt aat act tca aat aaa gaa cag        4420
Ala Lys Ala Gln Glu Ala Cys His Gly Asn Thr Ser Asn Lys Glu Gln
1395                1400                1405 tta act gct act aaa acg gag caa aat ata aaa gat ttt gag act tct        4468
Leu Thr Ala Thr Lys Thr Glu Gln Asn Ile Lys Asp Phe Glu Thr Ser
1410                1415                1420
```

-continued

```
gat aca ttt ttt cag act gca agt ggg aaa aat att agt gtc gcc aaa     4516
Asp Thr Phe Phe Gln Thr Ala Ser Gly Lys Asn Ile Ser Val Ala Lys
1425            1430                1435                1440 gag tta ttt aat aaa att gta aat ttc ttt gat cag aaa cca gaa gaa     4564
Glu Leu Phe Asn Lys Ile Val Asn Phe Phe Asp Gln Lys Pro Glu Glu
1445            1450                1455 ttg cat aac ttt tcc tta aat tct gaa tta cat tct gac ata aga aag     4612
Leu His Asn Phe Ser Leu Asn Ser Glu Leu His Ser Asp Ile Arg Lys
1460            1465                1470 aac aaa atg gac att cta agt tat gag gaa aca gac ata gtt aaa cac     4660
Asn Lys Met Asp Ile Leu Ser Tyr Glu Glu Thr Asp Ile Val Lys His
1475            1480                1485 aaa ata ctg aaa gaa agt gtc cca gtt ggt act gga aat caa cta gtg     4708
Lys Ile Leu Lys Glu Ser Val Pro Val Gly Thr Gly Asn Gln Leu Val
1490            1495                1500 acc ttc cag gga caa ccc gaa cgt gat gaa aag atc aaa gaa cct act     4756
Thr Phe Gln Gly Gln Pro Glu Arg Asp Glu Lys Ile Lys Glu Pro Thr
1505            1510                1515                1520 ctg ttg ggt ttt cat aca gct agc gga aaa aaa gtt aaa att gca aag     4804
Leu Leu Gly Phe His Thr Ala Ser Gly Lys Lys Val Lys Ile Ala Lys
1525            1530                1535 gaa tct ttg gac aaa gtg aaa aac ctt ttt gat gaa aaa gag caa ggt     4852
Glu Ser Leu Asp Lys Val Lys Asn Leu Phe Asp Glu Lys Glu Gln Gly
1540            1545                1550 act agt gaa atc acc agt ttt agc cat caa tgg gca aag acc cta aag     4900
Thr Ser Glu Ile Thr Ser Phe Ser His Gln Trp Ala Lys Thr Leu Lys
1555            1560                1565 tac aga gag gcc tgt aaa gac ctt gaa tta gca tgt gag acc att gag     4948
Tyr Arg Glu Ala Cys Lys Asp Leu Glu Leu Ala Cys Glu Thr Ile Glu
1570            1575                1580 atc aca gct gcc cca aag tgt aaa gaa atg cag aat tct ctc aat aat     4996
Ile Thr Ala Ala Pro Lys Cys Lys Glu Met Gln Asn Ser Leu Asn Asn
1585            1590                1595                1600 gat aaa aac ctt gtt tct att gag act gtg gtg cca cct aag ctc tta     5044
Asp Lys Asn Leu Val Ser Ile Glu Thr Val Val Pro Pro Lys Leu Leu
1605            1610                1615 agt gat aat tta tgt aga caa act gaa aat ctc aaa aca tca aaa agt     5092
Ser Asp Asn Leu Cys Arg Gln Thr Glu Asn Leu Lys Thr Ser Lys Ser
1620            1625                1630 atc ttt ttg aaa gtt aaa gta cat gaa aat gta gaa aaa gaa aca gca     5140
Ile Phe Leu Lys Val Lys Val His Glu Asn Val Glu Lys Glu Thr Ala
1635            1640                1645 aaa agt cct gca act tgt tac aca aat cag tcc cct tat tca gtc att     5188
Lys Ser Pro Ala Thr Cys Tyr Thr Asn Gln Ser Pro Tyr Ser Val Ile
1650            1655                1660 gaa aat tca gcc tta gct ttt tac aca agt tgt agt aga aaa act tct     5236
Glu Asn Ser Ala Leu Ala Phe Tyr Thr Ser Cys Ser Arg Lys Thr Ser
1665            1670                1675                1680 gtg agt cag act tca tta ctt gaa gca aaa aaa tgg ctt aga gaa gga     5284
Val Ser Gln Thr Ser Leu Leu Glu Ala Lys Lys Trp Leu Arg Glu Gly
1685            1690                1695 ata ttt gat ggt caa cca gaa aga ata aat act gca gat tat gta gga     5332
Ile Phe Asp Gly Gln Pro Glu Arg Ile Asn Thr Ala Asp Tyr Val Gly
1700            1705                1710 aat tat ttg tat gaa aat aat tca aac agt act ata gct gaa aat gac     5380
Asn Tyr Leu Tyr Glu Asn Asn Ser Asn Ser Thr Ile Ala Glu Asn Asp
1715            1720                1725 aaa aat cat ctc tcc gaa aaa caa gat act tat tta agt aac agt agc     5428
Lys Asn His Leu Ser Glu Lys Gln Asp Thr Tyr Leu Ser Asn Ser Ser
1730            1735                1740
```

```
atg tct aac agc tat tcc tac cat tct gat gag gta tat aat gat tca      5476
Met Ser Asn Ser Tyr Ser Tyr His Ser Asp Glu Val Tyr Asn Asp Ser
1745                1750                1755                1760 gga tat ctc tca aaa aat aaa ctt gat tct ggt att gag cca gta ttg      5524
Gly Tyr Leu Ser Lys Asn Lys Leu Asp Ser Gly Ile Glu Pro Val Leu
        1765                1770                1775 aag aat gtt gaa gat caa aaa aac act agt ttt tcc aaa gta ata tcc      5572
Lys Asn Val Glu Asp Gln Lys Asn Thr Ser Phe Ser Lys Val Ile Ser
1780                1785                1790 aat gta aaa gat gca aat gca tac cca caa act gta aat gaa gat att      5620
Asn Val Lys Asp Ala Asn Ala Tyr Pro Gln Thr Val Asn Glu Asp Ile
        1795                1800                1805 tgc gtt gag gaa ctt gtg act agc tct tca ccc tgc aaa aat aaa aat      5668
Cys Val Glu Glu Leu Val Thr Ser Ser Ser Pro Cys Lys Asn Lys Asn
1810                1815                1820 gca gcc att aaa ttg tcc ata tct aat agt aat aat ttt gag gta ggg      5716
Ala Ala Ile Lys Leu Ser Ile Ser Asn Ser Asn Asn Phe Glu Val Gly
        1825                1830                1835                1840 cca cct gca ttt agg ata gcc agt ggt aaa atc cgt ttg tgt tca cat      5764
Pro Pro Ala Phe Arg Ile Ala Ser Gly Lys Ile Arg Leu Cys Ser His
1845                1850                1855 gaa aca att aaa aaa gtg aaa gac ata ttt aca gac agt ttc agc aaa      5812
Glu Thr Ile Lys Lys Val Lys Asp Ile Phe Thr Asp Ser Phe Ser Lys
        1860                1865                1870 gta att aag gaa aac aac gag aat aaa tca aaa att tgc caa acg aaa      5860
Val Ile Lys Glu Asn Asn Glu Asn Lys Ser Lys Ile Cys Gln Thr Lys
1875                1880                1885 att atg gca ggt tgt tac gag gca ttg gat gat tca gag gat att ctt      5908
Ile Met Ala Gly Cys Tyr Glu Ala Leu Asp Asp Ser Glu Asp Ile Leu
        1890                1895                1900 cat aac tct cta gat aat gat gaa tgt agc atg cat tca cat aag gtt      5956
His Asn Ser Leu Asp Asn Asp Glu Cys Ser Met His Ser His Lys Val
1905                1910                1915                1920 ttt gct gac att cag agt gaa gaa att tta caa cat aac caa aat atg      6004
Phe Ala Asp Ile Gln Ser Glu Glu Ile Leu Gln His Asn Gln Asn Met
        1925                1930                1935 tct gga ttg gag aaa gtt tct aaa ata tca cct tgt gat gtt agt ttg      6052
Ser Gly Leu Glu Lys Val Ser Lys Ile Ser Pro Cys Asp Val Ser Leu
1940                1945                1950 gaa act tca gat ata tgt aaa tgt agt ata ggg aag ctt cat aag tca      6100
Glu Thr Ser Asp Ile Cys Lys Cys Ser Ile Gly Lys Leu His Lys Ser
        1955                1960                1965 gtc tca tct gca aat act tgt ggg att ttt agc aca gca agt gga aaa      6148
Val Ser Ser Ala Asn Thr Cys Gly Ile Phe Ser Thr Ala Ser Gly Lys
1970                1975                1980 tct gtc cag gta tca gat gct tca tta caa aac gca aga caa gtg ttt      6196
Ser Val Gln Val Ser Asp Ala Ser Leu Gln Asn Ala Arg Gln Val Phe
        1985                1990                1995                2000 tct gaa ata gaa gat agt acc aag caa gtc ttt tcc aaa gta ttg ttt      6244
Ser Glu Ile Glu Asp Ser Thr Lys Gln Val Phe Ser Lys Val Leu Phe
2005                2010                2015 aaa agt aac gaa cat tca gac cag ctc aca aga gaa gaa aat act gct      6292
Lys Ser Asn Glu His Ser Asp Gln Leu Thr Arg Glu Glu Asn Thr Ala
        2020                2025                2030 ata cgt act cca gaa cat tta ata tcc caa aaa ggc ttt tca tat aat      6340
Ile Arg Thr Pro Glu His Leu Ile Ser Gln Lys Gly Phe Ser Tyr Asn
2035                2040                2045 gtg gta aat tca tct gct ttc tct gga ttt agt aca gca agt gga aag      6388
Val Val Asn Ser Ser Ala Phe Ser Gly Phe Ser Thr Ala Ser Gly Lys
```

-continued

```
      2050                2055                2060
caa gtt tcc att tta gaa agt tcc tta cac aaa gtt aag gga gtg tta    6436
Gln Val Ser Ile Leu Glu Ser Ser Leu His Lys Val Lys Gly Val Leu
2065                2070                2075                2080 gag gaa ttt gat tta atc aga act gag cat agt ctt cac tat tca cct    6484
Glu Glu Phe Asp Leu Ile Arg Thr Glu His Ser Leu His Tyr Ser Pro
    2085                2090                2095 acg tct aga caa aat gta tca aaa ata ctt cct cgt gtt gat aag aga    6532
Thr Ser Arg Gln Asn Val Ser Lys Ile Leu Pro Arg Val Asp Lys Arg
2100                2105                2110 aac cca gag cac tgt gta aac tca gaa atg gaa aaa acc tgc agt aaa    6580
Asn Pro Glu His Cys Val Asn Ser Glu Met Glu Lys Thr Cys Ser Lys
2115                2120                2125 gaa ttt aaa tta tca aat aac tta aat gtt gaa ggt ggt tct tca gaa    6628
Glu Phe Lys Leu Ser Asn Asn Leu Asn Val Glu Gly Gly Ser Ser Glu
2130                2135                2140 aat aat cac tct att aaa gtt tct cca tat ctc tct caa ttt caa caa    6676
Asn Asn His Ser Ile Lys Val Ser Pro Tyr Leu Ser Gln Phe Gln Gln
2145                2150                2155                2160 gac aaa caa cag ttg gta tta gga acc aaa gtc tca ctt gtt gag aac    6724
Asp Lys Gln Gln Leu Val Leu Gly Thr Lys Val Ser Leu Val Glu Asn
2165                2170                2175 att cat gtt ttg gga aaa gaa cag gct tca cct aaa aac gta aaa atg    6772
Ile His Val Leu Gly Lys Glu Gln Ala Ser Pro Lys Asn Val Lys Met
2180                2185                2190 gaa att ggt aaa act gaa act ttt tct gat gtt cct gtg aaa aca aat    6820
Glu Ile Gly Lys Thr Glu Thr Phe Ser Asp Val Pro Val Lys Thr Asn
2195                2200                2205 ata gaa gtt tgt tct act tac tcc aaa gat tca gaa aac tac ttt gaa    6868
Ile Glu Val Cys Ser Thr Tyr Ser Lys Asp Ser Glu Asn Tyr Phe Glu
2210                2215                2220 aca gaa gca gta gaa att gct aaa gct ttt atg gaa gat gat gaa ctg    6916
Thr Glu Ala Val Glu Ile Ala Lys Ala Phe Met Glu Asp Asp Glu Leu
2225                2230                2235                2240 aca gat tct aaa ctg cca agt cat gcc aca cat tct ctt ttt aca tgt    6964
Thr Asp Ser Lys Leu Pro Ser His Ala Thr His Ser Leu Phe Thr Cys
2245                2250                2255 ccc gaa aat gag gaa atg gtt ttg tca aat tca aga att gga aaa aga    7012
Pro Glu Asn Glu Glu Met Val Leu Ser Asn Ser Arg Ile Gly Lys Arg
2260                2265                2270 aga gga gag ccc ctt atc tta gtg gga gaa ccc tca atc aaa aga aac    7060
Arg Gly Glu Pro Leu Ile Leu Val Gly Glu Pro Ser Ile Lys Arg Asn
2275                2280                2285 tta tta aat gaa ttt gac agg ata ata gaa aat caa gaa aaa tcc tta    7108
Leu Leu Asn Glu Phe Asp Arg Ile Ile Glu Asn Gln Glu Lys Ser Leu
2290                2295                2300 aag gct tca aaa agc act cca gat ggc aca ata aaa gat cga aga ttg    7156
Lys Ala Ser Lys Ser Thr Pro Asp Gly Thr Ile Lys Asp Arg Arg Leu
2305                2310                2315                2320 ttt atg cat cat gtt tct tta gag ccg att acc tgt gta ccc ttt cgc    7204
Phe Met His His Val Ser Leu Glu Pro Ile Thr Cys Val Pro Phe Arg
2325                2330                2335 aca act aag gaa cgt caa gag ata cag aat cca aat ttt acc gca cct    7252
Thr Thr Lys Glu Arg Gln Glu Ile Gln Asn Pro Asn Phe Thr Ala Pro
2340                2345                2350 ggt caa gaa ttt ctg tct aaa tct cat ttg tat gaa cat ctg act ttg    7300
Gly Gln Glu Phe Leu Ser Lys Ser His Leu Tyr Glu His Leu Thr Leu
2355                2360                2365 gaa aaa tct tca agc aat tta gca gtt tca gga cat cca ttt tat caa    7348
```

|  |  |
|---|---|
| Glu Lys Ser Ser Ser Asn Leu Ala Val Ser Gly His Pro Phe Tyr Gln<br>2370                           2375                             2380 |  |
| gtt tct gct aca aga aat gaa aaa atg aga cac ttg att act aca ggc<br>Val Ser Ala Thr Arg Asn Glu Lys Met Arg His Leu Ile Thr Thr Gly<br>2385                           2390                           2395                    2400 | 7396 |
| aga cca acc aaa gtc ttt gtt cca cct ttt aaa act aaa tca cat ttt<br>Arg Pro Thr Lys Val Phe Val Pro Pro Phe Lys Thr Lys Ser His Phe<br>2405                         2410                         2415 | 7444 |
| cac aga gtt gaa cag tgt gtt agg aat att aac ttg gag gaa aac aga<br>His Arg Val Glu Gln Cys Val Arg Asn Ile Asn Leu Glu Glu Asn Arg<br>2420                       2425                         2430 | 7492 |
| caa aag caa aac att gat gga cat ggc tct gat gat agt aaa aat aag<br>Gln Lys Gln Asn Ile Asp Gly His Gly Ser Asp Asp Ser Lys Asn Lys<br>2435                       2440                        2445 | 7540 |
| att aat gac aat gag att cat cag ttt aac aaa aac aac tcc aat caa<br>Ile Asn Asp Asn Glu Ile His Gln Phe Asn Lys Asn Asn Ser Asn Gln<br>2450                       2455                       2460 | 7588 |
| gca gca gct gta act ttc aca aag tgt gaa gaa gaa cct tta gat tta<br>Ala Ala Ala Val Thr Phe Thr Lys Cys Glu Glu Glu Pro Leu Asp Leu<br>2465                       2470                       2475                2480 | 7636 |
| att aca agt ctt cag aat gcc aga gat ata cag gat atg cga att aag<br>Ile Thr Ser Leu Gln Asn Ala Arg Asp Ile Gln Asp Met Arg Ile Lys<br>2485                       2490                       2495 | 7684 |
| aag aaa caa agg caa cgc gtc ttt cca cag cca ggc agt ctg tat ctt<br>Lys Lys Gln Arg Gln Arg Val Phe Pro Gln Pro Gly Ser Leu Tyr Leu<br>2500                       2505                        2510 | 7732 |
| gca aaa aca tcc act ctg cct cga atc tct ctg aaa gca gca gta gga<br>Ala Lys Thr Ser Thr Leu Pro Arg Ile Ser Leu Lys Ala Ala Val Gly<br>2515                       2520                        2525 | 7780 |
| ggc caa gtt ccc tct gcg tgt tct cat aaa cag ctg tat acg tat ggc<br>Gly Gln Val Pro Ser Ala Cys Ser His Lys Gln Leu Tyr Thr Tyr Gly<br>2530                       2535                        2540 | 7828 |
| gtt tct aaa cat tgc ata aaa att aac agc aaa aat gca gag tct ttt<br>Val Ser Lys His Cys Ile Lys Ile Asn Ser Lys Asn Ala Glu Ser Phe<br>2545                       2550                       2555                2560 | 7876 |
| cag ttt cac act gaa gat tat ttt ggt aag gaa agt tta tgg act gga<br>Gln Phe His Thr Glu Asp Tyr Phe Gly Lys Glu Ser Leu Trp Thr Gly<br>2565                       2570                        2575 | 7924 |
| aaa gga ata cag ttg gct gat ggt gga tgg ctc ata ccc tcc aat gat<br>Lys Gly Ile Gln Leu Ala Asp Gly Gly Trp Leu Ile Pro Ser Asn Asp<br>2580                       2585                        2590 | 7972 |
| gga aag gct gga aaa gaa gaa ttt tat agg gct ctg tgt gac act cca<br>Gly Lys Ala Gly Lys Glu Glu Phe Tyr Arg Ala Leu Cys Asp Thr Pro<br>2595                       2600                        2605 | 8020 |
| ggt gtg gat cca aag ctt att tct aga att tgg gtt tat aat cac tat<br>Gly Val Asp Pro Lys Leu Ile Ser Arg Ile Trp Val Tyr Asn His Tyr<br>2610                       2615                        2620 | 8068 |
| aga tgg atc ata tgg aaa ctg gca gct atg gaa tgt gcc ttt cct aag<br>Arg Trp Ile Ile Trp Lys Leu Ala Ala Met Glu Cys Ala Phe Pro Lys<br>2625                       2630                        2635                2640 | 8116 |
| gaa ttt gct aat aga tgc cta agc cca gaa agg gtg ctt ctt caa cta<br>Glu Phe Ala Asn Arg Cys Leu Ser Pro Glu Arg Val Leu Leu Gln Leu<br>2645                       2650                        2655 | 8164 |
| aaa tac aga tat gat acg gaa att gat aga agc aga aga tcg gct ata<br>Lys Tyr Arg Tyr Asp Thr Glu Ile Asp Arg Ser Arg Arg Ser Ala Ile<br>2660                       2665                        2670 | 8212 |
| aaa aag ata atg gaa agg gat gac aca gct gca aaa aca ctt gtt ctc<br>Lys Lys Ile Met Glu Arg Asp Asp Thr Ala Ala Lys Thr Leu Val Leu<br>2675                       2680                        2685 | 8260 |

```
tgt gtt tct gac ata att tca ttg agc gca aat ata tct gaa act tct      8308
Cys Val Ser Asp Ile Ile Ser Leu Ser Ala Asn Ile Ser Glu Thr Ser
2690            2695                2700 agc aat aaa act agt agt gca gat acc caa aaa gtg gcc att att gaa      8356
Ser Asn Lys Thr Ser Ser Ala Asp Thr Gln Lys Val Ala Ile Ile Glu
2705            2710                2715                    2720 ctt aca gat ggg tgg tat gct gtt aag gcc cag tta gat ccc ctc          8404
Leu Thr Asp Gly Trp Tyr Ala Val Lys Ala Gln Leu Asp Pro Pro Leu
2725            2730                2735 tta gct gtc tta aag aat ggc aga ctg aca gtt ggt cag aag att att      8452
Leu Ala Val Leu Lys Asn Gly Arg Leu Thr Val Gly Gln Lys Ile Ile
2740            2745                2750 ctt cat gga gca gaa ctg gtg ggc tct cct gat gcc tgt aca cct ctt      8500
Leu His Gly Ala Glu Leu Val Gly Ser Pro Asp Ala Cys Thr Pro Leu
2755            2760                2765 gaa gcc cca gaa tct ctt atg tta aag att tct gct aac agt act cgg      8548
Glu Ala Pro Glu Ser Leu Met Leu Lys Ile Ser Ala Asn Ser Thr Arg
2770            2775                2780 cct gct cgc tgg tat acc aaa ctt gga ttc ttt cct gac cct aga cct      8596
Pro Ala Arg Trp Tyr Thr Lys Leu Gly Phe Phe Pro Asp Pro Arg Pro
2785            2790                2795                    2800 ttt cct ctg ccc tta tca tcg ctt ttc agt gat gga gga aat gtt ggt      8644
Phe Pro Leu Pro Leu Ser Ser Leu Phe Ser Asp Gly Gly Asn Val Gly
2805            2810                2815 tgt gtt gat gta att att caa aga gca tac cct ata cag cgg atg gag      8692
Cys Val Asp Val Ile Ile Gln Arg Ala Tyr Pro Ile Gln Arg Met Glu
2820            2825                2830 aag aca tca tct gga tta tac ata ttt cgc aat gaa aga gag gaa gaa      8740
Lys Thr Ser Ser Gly Leu Tyr Ile Phe Arg Asn Glu Arg Glu Glu Glu
2835            2840                2845 aag gaa gca gca aaa tat gtg gag gcc caa caa aag aga cta gaa gcc      8788
Lys Glu Ala Ala Lys Tyr Val Glu Ala Gln Gln Lys Arg Leu Glu Ala
2850            2855                2860 tta ttc act aaa att cag gag gaa ttt gaa gaa cat gaa gaa aac aca      8836
Leu Phe Thr Lys Ile Gln Glu Glu Phe Glu Glu His Glu Glu Asn Thr
2865            2870                2875                    2880 aca aaa cca tat tta cca tca cgt gca cta aca aga cag caa gtt cgt      8884
Thr Lys Pro Tyr Leu Pro Ser Arg Ala Leu Thr Arg Gln Gln Val Arg
2885            2890                2895 gct ttg caa gat ggt gca gag ctt tat gaa gca gtg aag aat gca gca      8932
Ala Leu Gln Asp Gly Ala Glu Leu Tyr Glu Ala Val Lys Asn Ala Ala
2900            2905                2910 gac cca gct tac ctt gag ggt tat ttc agt gaa gag cag tta aga gcc      8980
Asp Pro Ala Tyr Leu Glu Gly Tyr Phe Ser Glu Glu Gln Leu Arg Ala
2915            2920                2925 ttg aat aat cac agg caa atg ttg aat gat aag aaa caa gct cag atc      9028
Leu Asn Asn His Arg Gln Met Leu Asn Asp Lys Lys Gln Ala Gln Ile
2930            2935                2940 cag ttg gaa att agg aag gcc atg gaa tct gct gaa caa aag gaa caa      9076
Gln Leu Glu Ile Arg Lys Ala Met Glu Ser Ala Glu Gln Lys Glu Gln
2945            2950                2955                    2960 ggt tta tca agg gat gtc aca acc gtg tgg aag ttg cgt att gta agc      9124
Gly Leu Ser Arg Asp Val Thr Thr Val Trp Lys Leu Arg Ile Val Ser
2965            2970                2975 tat tca aaa aaa gaa aaa gat tca gtt ata ctg agt att tgg cgt cca      9172
Tyr Ser Lys Lys Glu Lys Asp Ser Val Ile Leu Ser Ile Trp Arg Pro
2980            2985                2990 tca tca gat tta tat tct ctg tta aca gaa gga aag aga tac aga att      9220
Ser Ser Asp Leu Tyr Ser Leu Leu Thr Glu Gly Lys Arg Tyr Arg Ile
2995            3000                3005
```

```
tat cat ctt gca act tca aaa tct aaa agt aaa tct gaa aga gct aac      9268
Tyr His Leu Ala Thr Ser Lys Ser Lys Ser Glu Arg Ala Asn
3010            3015            3020 ata cag tta gca gcg aca aaa aaa act cag tat caa caa cta ccg gtt      9316
Ile Gln Leu Ala Ala Thr Lys Lys Thr Gln Tyr Gln Gln Leu Pro Val
3025            3030            3035            3040 tca gat gaa att tta ttt cag att tac cag cca cgg gag ccc ctt cac      9364
Ser Asp Glu Ile Leu Phe Gln Ile Tyr Gln Pro Arg Glu Pro Leu His
3045            3050            3055 ttc agc aaa ttt tta gat cca gac ttt cag cca tct tgt tct gag gtg      9412
Phe Ser Lys Phe Leu Asp Pro Asp Phe Gln Pro Ser Cys Ser Glu Val
3060            3065            3070 gac cta ata gga ttt gtc gtt tct gtt gtg aaa aaa aca gga ctt gcc      9460
Asp Leu Ile Gly Phe Val Val Ser Val Val Lys Lys Thr Gly Leu Ala
3075            3080            3085 cct ttc gtc tat ttg tca gac gaa tgt tac aat tta ctg gca ata aag      9508
Pro Phe Val Tyr Leu Ser Asp Glu Cys Tyr Asn Leu Leu Ala Ile Lys
3090            3095            3100 ttt tgg ata gac ctt aat gag gac att att aag cct cat atg tta att      9556
Phe Trp Ile Asp Leu Asn Glu Asp Ile Ile Lys Pro His Met Leu Ile
3105            3110            3115            3120 gct gca agc aac ctc cag tgg cga cca gaa tcc aaa tca ggc ctt ctt      9604
Ala Ala Ser Asn Leu Gln Trp Arg Pro Glu Ser Lys Ser Gly Leu Leu
3125            3130            3135 act tta ttt gct gga gat ttt tct gtg ttt tct gct agt cca aaa gag      9652
Thr Leu Phe Ala Gly Asp Phe Ser Val Phe Ser Ala Ser Pro Lys Glu
3140            3145            3150 ggc cac ttt caa gag aca ttc aac aaa atg aaa aat act gtt gag aat      9700
Gly His Phe Gln Glu Thr Phe Asn Lys Met Lys Asn Thr Val Glu Asn
3155            3160            3165 att gac ata ctt tgc aat gaa gca gaa aac aag ctt atg cat ata ctg      9748
Ile Asp Ile Leu Cys Asn Glu Ala Glu Asn Lys Leu Met His Ile Leu
3170            3175            3180 cat gca aat gat ccc aag tgg tcc acc cca act aaa gac tgt act tca      9796
His Ala Asn Asp Pro Lys Trp Ser Thr Pro Thr Lys Asp Cys Thr Ser
3185            3190            3195            3200 ggg ccg tac act gct caa atc att cct ggt aca gga aac aag ctt ctg      9844
Gly Pro Tyr Thr Ala Gln Ile Ile Pro Gly Thr Gly Asn Lys Leu Leu
3205            3210            3215 atg tct tct cct aat tgt gag ata tat tat caa agt cct tta tca ctt      9892
Met Ser Ser Pro Asn Cys Glu Ile Tyr Tyr Gln Ser Pro Leu Ser Leu
3220            3225            3230 tgt atg gcc aaa agg aag tct gtt tcc aca cct gtc tca gcc cag atg      9940
Cys Met Ala Lys Arg Lys Ser Val Ser Thr Pro Val Ser Ala Gln Met
3235            3240            3245 act tca aag tct tgt aaa ggg gag aaa gag att gat gac caa aag aac      9988
Thr Ser Lys Ser Cys Lys Gly Glu Lys Glu Ile Asp Asp Gln Lys Asn
3250            3255            3260 tgc aaa aag aga aga gcc ttg gat ttc ttg agt aga ctg cct tta cct     10036
Cys Lys Lys Arg Arg Ala Leu Asp Phe Leu Ser Arg Leu Pro Leu Pro
3265            3270            3275            3280 cca cct gtt agt ccc att tgt aca ttt gtt tct ccg gct gca cag aag     10084
Pro Pro Val Ser Pro Ile Cys Thr Phe Val Ser Pro Ala Ala Gln Lys
3285            3290            3295 gca ttt cag cca cca agg agt tgt ggc acc aaa tac gaa aca ccc ata     10132
Ala Phe Gln Pro Pro Arg Ser Cys Gly Thr Lys Tyr Glu Thr Pro Ile
3300            3305            3310 aag aaa aaa gaa ctg aat tct cct cag atg act cca ttt aaa aaa ttc     10180
Lys Lys Lys Glu Leu Asn Ser Pro Gln Met Thr Pro Phe Lys Lys Phe
```

```
                    -continued
3315                3320                3325 aat gaa att tct ctt ttg gaa agt aat tca ata gct gac gaa gaa ctt   10228
Asn Glu Ile Ser Leu Leu Glu Ser Asn Ser Ile Ala Asp Glu Glu Leu
3330                3335                3340 gca ttg ata aat acc caa gct ctt ttg tct ggt tca aca gga gaa aaa   10276
Ala Leu Ile Asn Thr Gln Ala Leu Leu Ser Gly Ser Thr Gly Glu Lys
3345                3350                3355                3360 caa ttt ata tct gtc agt gaa tcc act agg act gct ccc acc agt tca   10324
Gln Phe Ile Ser Val Ser Glu Ser Thr Arg Thr Ala Pro Thr Ser Ser
3365                3370                3375 gaa gat tat ctc aga ctg aaa cga cgt tgt act aca tct ctg atc aaa   10372
Glu Asp Tyr Leu Arg Leu Lys Arg Arg Cys Thr Thr Ser Leu Ile Lys
3380                3385                3390 gaa cag gag agt tcc cag gcc agt acg gaa gaa tgt gag aaa aat aag   10420
Glu Gln Glu Ser Ser Gln Ala Ser Thr Glu Glu Cys Glu Lys Asn Lys
3395                3400                3405 cag gac aca att aca act aaa aaa tat atc taagcatttg caaaggcgac     10470
Gln Asp Thr Ile Thr Thr Lys Lys Tyr Ile
3410                3415 aataaattat tgacgcttaa cctttccagt ttataagact ggaatataat ttcaaaccac  10530
acattagtac ttatgttgcm caatgagaaa agaaattagt ttcaaattta cctcagcgtt  10590
tgtgtatcgg gcaaaaatcg ttttgcccga ttccgtattg gtatactttt gcctcagttg  10650
catatcctaa aactaaatgt aatttattaa ctaatcaaga aaacatctt tggctgagct   10710 cggtggctca tgcctgtaat cccaacactt tgagaagctg aggtgggagg agtgcttgag  10770
gccaggagtt caagaccagc ctgggcaaca tagggagacc ccatctttac gaagaaaaaa  10830
aaaaagggga aagaaaatc ttttaaatct ttggatttca ctacaagtat tatttttacaa 10890 gtgaaataaa cataccattt tcttttagat tgtgtcatta aatggaatga ggtctcttag  10950
tacagttatt ttgatgcaga taattccttt tagtttagct actatttag gggattttt   11010 ttagaggtaa ctcactatga aatagttccc cttaatgcaa atatgttggt tctgcaatag  11070
ttccatcctg ttcaaaartc rggrtgaawa tgaagagtgg tgttyccttt tgagcaattc  11130
tcatccttaa gtcagcrtga ttataagaaa aatagaaccc ycagtgtaac yctaattcct  11190
ttttrctatt ccagtgtgat ctctgaaakt aaattacttc mactaaaaat tcaaaaactt  11250
waamtcagaa rawttcawag twgatttatt ttt                              11283
```

(2) INFORMATION FOR SEQ ID NO:4:

(i) SEQUENCE CHARACTERISTICS:
        (A) LENGTH: 3418
        (B) TYPE: amino acid
        (C) STRANDEDNESS: single
        (D) TOPOLOGY: unknown (ix) FEATURE:
        (A) NAME/KEY: BRCA2 protein (x) PUBLICATION INFORMATION:
        (A) AUTHORS: Wooster, R. et al.
        (B) TITLE: Identification of the breast cancer
            susceptibility gene BRCA2
        (C) JOURNAL: Nature
        (D) VOLUME: 379
        (E) PAGES: 789-792
        (F) DATE: 1995
        (K) RELEVANT RESIDUES IN SEQ ID NO:4: granin box domain at
            amino acids 3334-3344

(xi) SEQUENCE DESCRIPTION: SEQ ID NO:4:

-continued

```
Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
                20                  25                  30

Glu Glu Leu Ser Ser Glu Ala Pro Pro Tyr Asn Ser Glu Pro Ala Glu
            35                  40                  45

Glu Ser Glu His Lys Asn Asn Asn Tyr Glu Pro Asn Leu Phe Lys Thr
        50                  55                  60

Pro Gln Arg Lys Pro Ser Tyr Asn Gln Leu Ala Ser Thr Pro Ile Ile
65                  70                  75                  80

Phe Lys Glu Gln Gly Leu Thr Leu Pro Leu Tyr Gln Ser Pro Val Lys
                85                  90                  95

Glu Leu Asp Lys Phe Lys Leu Asp Leu Gly Arg Asn Val Pro Asn Ser
                100                 105                 110

Arg His Lys Ser Leu Arg Thr Val Lys Tyr Lys Met Asp Gln Ala Asp
            115                 120                 125

Asp Val Ser Cys Pro Leu Leu Asn Ser Cys Leu Ser Glu Ser Pro Val
        130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                165                 170                 175

Pro Lys His Ile Ser Glu Ser Leu Gly Ala Glu Val Asp Pro Asp Met
            180                 185                 190

Ser Trp Ser Ser Ser Leu Ala Thr Pro Pro Thr Leu Ser Ser Thr Val
        195                 200                 205

Leu Ile Val Arg Asn Glu Glu Ala Ser Glu Thr Val Phe Pro His Asp
    210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                245                 250                 255

Asn Gln Arg Glu Ala Ala Ser His Gly Phe Gly Lys Thr Ser Gly Asn
            260                 265                 270

Ser Phe Lys Val Asn Ser Cys Lys Asp His Ile Gly Lys Ser Met Pro
        275                 280                 285

Asn Val Leu Glu Asp Glu Val Tyr Glu Thr Val Val Asp Thr Ser Glu
    290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Lys Ile Phe His Glu Ala
                325                 330                 335

Asn Ala Asp Glu Cys Glu Lys Ser Lys Asn Gln Val Lys Glu Lys Tyr
            340                 345                 350

Ser Phe Val Ser Glu Val Glu Pro Asn Asp Thr Asp Pro Leu Asp Ser
        355                 360                 365

Asn Val Ala His Gln Lys Pro Phe Glu Ser Gly Ser Asp Lys Ile Ser
    370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
                405                 410                 415

Ser Ser Cys Asp Gln Asn Ile Ser Glu Lys Asp Leu Leu Asp Thr Glu
```

```
                     420              425              430
Asn Lys Arg Lys Lys Asp Phe Leu Thr Ser Glu Asn Ser Leu Pro Arg
            435              440              445
Ile Ser Ser Leu Pro Lys Ser Glu Lys Pro Leu Asn Glu Glu Thr Val
450              455              460
Val Asn Lys Arg Asp Glu Glu Gln His Leu Glu Ser His Thr Asp Cys
465              470              475              480
Ile Leu Ala Val Lys Gln Ala Ile Ser Gly Thr Ser Pro Val Ala Ser
            485              490              495
Ser Phe Gln Gly Ile Lys Lys Ser Ile Phe Arg Ile Arg Glu Ser Pro
            500              505              510
Lys Glu Thr Phe Asn Ala Ser Phe Ser Gly His Met Thr Asp Pro Asn
            515              520              525
Phe Lys Lys Glu Thr Glu Ala Ser Glu Ser Gly Leu Glu Ile His Thr
530              535              540
Val Cys Ser Gln Lys Glu Asp Ser Leu Cys Pro Asn Leu Ile Asp Asn
545              550              555              560
Gly Ser Trp Pro Ala Thr Thr Thr Gln Asn Ser Val Ala Leu Lys Asn
            565              570              575
Ala Gly Leu Ile Ser Thr Leu Lys Lys Lys Thr Asn Lys Phe Ile Tyr
            580              585              590
Ala Ile His Asp Glu Thr Phe Tyr Lys Gly Lys Lys Ile Pro Lys Asp
            595              600              605
Gln Lys Ser Glu Leu Ile Asn Cys Ser Ala Gln Phe Glu Ala Asn Ala
            610              615              620
Phe Glu Ala Pro Leu Thr Phe Ala Asn Ala Asp Ser Gly Leu Leu His
625              630              635              640
Ser Ser Val Lys Arg Ser Cys Ser Gln Asn Asp Ser Glu Glu Pro Thr
            645              650              655
Leu Ser Leu Thr Ser Ser Phe Gly Thr Ile Leu Arg Lys Cys Ser Arg
            660              665              670
Asn Glu Thr Cys Ser Asn Asn Thr Val Ile Ser Gln Asp Leu Asp Tyr
            675              680              685
Lys Glu Ala Lys Cys Asn Lys Glu Lys Leu Gln Leu Phe Ile Thr Pro
            690              695              700
Glu Ala Asp Ser Leu Ser Cys Leu Gln Glu Gly Gln Cys Glu Asn Asp
705              710              715              720
Pro Lys Ser Lys Lys Val Ser Asp Ile Lys Glu Glu Val Leu Ala Ala
            725              730              735
Ala Cys His Pro Val Gln His Ser Lys Val Glu Tyr Ser Asp Thr Asp
            740              745              750
Phe Gln Ser Gln Lys Ser Leu Leu Tyr Asp His Glu Asn Ala Ser Thr
            755              760              765
Leu Ile Leu Thr Pro Thr Ser Lys Asp Val Leu Ser Asn Leu Val Met
770              775              780
Ile Ser Arg Gly Lys Glu Ser Tyr Lys Met Ser Asp Lys Leu Lys Gly
785              790              795              800
Asn Asn Tyr Glu Ser Asp Val Glu Leu Thr Lys Asn Ile Pro Met Glu
            805              810              815
Lys Asn Gln Asp Val Cys Ala Leu Asn Glu Asn Tyr Lys Asn Val Glu
            820              825              830
Leu Leu Pro Pro Glu Lys Tyr Met Arg Val Ala Ser Pro Ser Arg Lys
            835              840              845
```

-continued

```
Val Gln Phe Asn Gln Asn Thr Asn Leu Arg Val Ile Gln Lys Asn Gln
    850                 855                 860
Glu Glu Thr Thr Ser Ile Ser Lys Ile Thr Val Asn Pro Asp Ser Glu
865                 870                 875                 880
Glu Leu Phe Ser Asp Asn Glu Asn Asn Phe Val Phe Gln Val Ala Asn
                885                 890                 895
Glu Arg Asn Asn Leu Ala Leu Gly Asn Thr Lys Glu Leu His Glu Thr
            900                 905                 910
Asp Leu Thr Cys Val Asn Glu Pro Ile Phe Lys Asn Ser Thr Met Val
        915                 920                 925
Leu Tyr Gly Asp Thr Gly Asp Lys Gln Ala Thr Gln Val Ser Ile Lys
    930                 935                 940
Lys Asp Leu Val Tyr Val Leu Ala Glu Glu Asn Lys Asn Ser Val Lys
945                 950                 955                 960
Gln His Ile Lys Met Thr Leu Gly Gln Asp Leu Lys Ser Asp Ile Ser
                965                 970                 975
Leu Asn Ile Asp Lys Ile Pro Glu Lys Asn Asn Asp Tyr Met Asn Lys
            980                 985                 990
Trp Ala Gly Leu Leu Gly Pro Ile Ser Asn His Ser Phe Gly Gly Ser
        995                 1000                1005
Phe Arg Thr Ala Ser Asn Lys Glu Ile Lys Leu Ser Glu His Asn Ile
    1010                1015                1020
Lys Lys Ser Lys Met Phe Phe Lys Asp Ile Glu Glu Gln Tyr Pro Thr
1025                1030                1035                1040
Ser Leu Ala Cys Val Glu Ile Val Asn Thr Leu Ala Leu Asp Asn Gln
                1045                1050                1055
Lys Lys Leu Ser Lys Pro Gln Ser Ile Asn Thr Val Ser Ala His Leu
            1060                1065                1070
Gln Ser Ser Val Val Ser Asp Cys Lys Asn Ser His Ile Thr Pro
        1075                1080                1085
Gln Met Leu Phe Ser Lys Gln Asp Phe Asn Ser Asn His Asn Leu Thr
    1090                1095                1100
Pro Ser Gln Lys Ala Glu Ile Thr Glu Leu Ser Thr Ile Leu Glu Glu
1105                1110                1115                1120
Ser Gly Ser Gln Phe Glu Phe Thr Gln Phe Arg Lys Pro Ser Tyr Ile
                1125                1130                1135
Leu Gln Lys Ser Thr Phe Glu Val Pro Glu Asn Gln Met Thr Ile Leu
            1140                1145                1150
Lys Thr Thr Ser Glu Glu Cys Arg Asp Ala Asp Leu His Val Ile Met
        1155                1160                1165
Asn Ala Pro Ser Ile Gly Gln Val Asp Ser Ser Lys Gln Phe Glu Gly
    1170                1175                1180
Thr Val Glu Ile Lys Arg Lys Phe Ala Gly Leu Leu Lys Asn Asp Cys
1185                1190                1195                1200
Asn Lys Ser Ala Ser Gly Tyr Leu Thr Asp Glu Asn Glu Val Gly Phe
                1205                1210                1215
Arg Gly Phe Tyr Ser Ala His Gly Thr Lys Leu Asn Val Ser Thr Glu
            1220                1225                1230
Ala Leu Gln Lys Ala Val Lys Leu Phe Ser Asp Ile Glu Asn Ile Ser
        1235                1240                1245
Glu Glu Thr Ser Ala Glu Val His Pro Ile Ser Leu Ser Ser Ser Lys
    1250                1255                1260
```

```
Cys His Asp Ser Val Val Ser Met Phe Lys Ile Glu Asn His Asn Asp
1265                1270                1275                1280

Lys Thr Val Ser Glu Lys Asn Asn Lys Cys Gln Leu Ile Leu Gln Asn
            1285                1290                1295

Asn Ile Glu Met Thr Thr Gly Thr Phe Val Glu Ile Thr Glu Asn
        1300                1305                1310

Tyr Lys Arg Asn Thr Glu Asn Glu Asp Asn Lys Tyr Thr Ala Ala Ser
        1315                1320                1325

Arg Asn Ser His Asn Leu Glu Phe Asp Gly Ser Asp Ser Ser Lys Asn
        1330                1335                1340

Asp Thr Val Cys Ile His Lys Asp Glu Thr Asp Leu Leu Phe Thr Asp
1345                1350                1355                1360

Gln His Asn Ile Cys Leu Lys Leu Ser Gly Gln Phe Met Lys Glu Gly
            1365                1370                1375

Asn Thr Gln Ile Lys Glu Asp Leu Ser Asp Leu Thr Phe Leu Glu Val
            1380                1385                1390

Ala Lys Ala Gln Glu Ala Cys His Gly Asn Thr Ser Asn Lys Glu Gln
        1395                1400                1405

Leu Thr Ala Thr Lys Thr Glu Gln Asn Ile Lys Asp Phe Glu Thr Ser
        1410                1415                1420

Asp Thr Phe Phe Gln Thr Ala Ser Gly Lys Asn Ile Ser Val Ala Lys
1425                1430                1435                1440

Glu Leu Phe Asn Lys Ile Val Asn Phe Phe Asp Gln Lys Pro Glu Glu
            1445                1450                1455

Leu His Asn Phe Ser Leu Asn Ser Glu Leu His Ser Asp Ile Arg Lys
        1460                1465                1470

Asn Lys Met Asp Ile Leu Ser Tyr Glu Glu Thr Asp Ile Val Lys His
        1475                1480                1485

Lys Ile Leu Lys Glu Ser Val Pro Val Gly Thr Gly Asn Gln Leu Val
        1490                1495                1500

Thr Phe Gln Gly Gln Pro Glu Arg Asp Glu Lys Ile Lys Glu Pro Thr
1505                1510                1515                1520

Leu Leu Gly Phe His Thr Ala Ser Gly Lys Lys Val Lys Ile Ala Lys
            1525                1530                1535

Glu Ser Leu Asp Lys Val Lys Asn Leu Phe Asp Glu Lys Glu Gln Gly
            1540                1545                1550

Thr Ser Glu Ile Thr Ser Phe Ser His Gln Trp Ala Lys Thr Leu Lys
        1555                1560                1565

Tyr Arg Glu Ala Cys Lys Asp Leu Glu Leu Ala Cys Glu Thr Ile Glu
        1570                1575                1580

Ile Thr Ala Ala Pro Lys Cys Lys Glu Met Gln Asn Ser Leu Asn Asn
1585                1590                1595                1600

Asp Lys Asn Leu Val Ser Ile Glu Thr Val Val Pro Pro Lys Leu Leu
            1605                1610                1615

Ser Asp Asn Leu Cys Arg Gln Thr Glu Asn Leu Lys Thr Ser Lys Ser
        1620                1625                1630

Ile Phe Leu Lys Val Lys Val His Glu Asn Val Glu Lys Glu Thr Ala
        1635                1640                1645

Lys Ser Pro Ala Thr Cys Tyr Thr Asn Gln Ser Pro Tyr Ser Val Ile
        1650                1655                1660

Glu Asn Ser Ala Leu Ala Phe Tyr Thr Ser Cys Ser Arg Lys Thr Ser
1665                1670                1675                1680

Val Ser Gln Thr Ser Leu Leu Glu Ala Lys Lys Trp Leu Arg Glu Gly
```

```
                    1685                1690                1695
Ile Phe Asp Gly Gln Pro Glu Arg Ile Asn Thr Ala Asp Tyr Val Gly
            1700                1705                1710
Asn Tyr Leu Tyr Glu Asn Asn Ser Asn Ser Thr Ile Ala Glu Asn Asp
        1715                1720                1725
Lys Asn His Leu Ser Glu Lys Gln Asp Thr Tyr Leu Ser Asn Ser Ser
        1730                1735                1740
Met Ser Asn Ser Tyr Ser Tyr His Ser Asp Glu Val Tyr Asn Asp Ser
1745                1750                1755                1760
Gly Tyr Leu Ser Lys Asn Lys Leu Asp Ser Gly Ile Glu Pro Val Leu
                1765                1770                1775
Lys Asn Val Glu Asp Gln Lys Asn Thr Ser Phe Ser Lys Val Ile Ser
            1780                1785                1790
Asn Val Lys Asp Ala Asn Ala Tyr Pro Gln Thr Val Asn Glu Asp Ile
        1795                1800                1805
Cys Val Glu Glu Leu Val Thr Ser Ser Ser Pro Cys Lys Asn Lys Asn
        1810                1815                1820
Ala Ala Ile Lys Leu Ser Ile Ser Asn Ser Asn Asn Phe Glu Val Gly
1825                1830                1835                1840
Pro Pro Ala Phe Arg Ile Ala Ser Gly Lys Ile Arg Leu Cys Ser His
                1845                1850                1855
Glu Thr Ile Lys Lys Val Lys Asp Ile Phe Thr Asp Ser Phe Ser Lys
            1860                1865                1870
Val Ile Lys Glu Asn Asn Glu Asn Lys Ser Lys Ile Cys Gln Thr Lys
        1875                1880                1885
Ile Met Ala Gly Cys Tyr Glu Ala Leu Asp Asp Ser Glu Asp Ile Leu
        1890                1895                1900
His Asn Ser Leu Asp Asn Asp Glu Cys Ser Met His Ser His Lys Val
1905                1910                1915                1920
Phe Ala Asp Ile Gln Ser Glu Glu Ile Leu Gln His Asn Gln Asn Met
                1925                1930                1935
Ser Gly Leu Glu Lys Val Ser Lys Ile Ser Pro Cys Asp Val Ser Leu
            1940                1945                1950
Glu Thr Ser Asp Ile Cys Lys Cys Ser Ile Gly Lys Leu His Lys Ser
        1955                1960                1965
Val Ser Ser Ala Asn Thr Cys Gly Ile Phe Ser Thr Ala Ser Gly Lys
        1970                1975                1980
Ser Val Gln Val Ser Asp Ala Ser Leu Gln Asn Ala Arg Gln Val Phe
1985                1990                1995                2000
Ser Glu Ile Glu Asp Ser Thr Lys Gln Val Phe Ser Lys Val Leu Phe
                2005                2010                2015
Lys Ser Asn Glu His Ser Asp Gln Leu Thr Arg Glu Glu Asn Thr Ala
            2020                2025                2030
Ile Arg Thr Pro Glu His Leu Ile Ser Gln Lys Gly Phe Ser Tyr Asn
        2035                2040                2045
Val Val Asn Ser Ser Ala Phe Ser Gly Phe Ser Thr Ala Ser Gly Lys
        2050                2055                2060
Gln Val Ser Ile Leu Glu Ser Ser Leu His Lys Val Lys Gly Val Leu
2065                2070                2075                2080
Glu Glu Phe Asp Leu Ile Arg Thr Glu His Ser Leu His Tyr Ser Pro
                2085                2090                2095
Thr Ser Arg Gln Asn Val Ser Lys Ile Leu Pro Arg Val Asp Lys Arg
            2100                2105                2110
```

-continued

```
Asn Pro Glu His Cys Val Asn Ser Glu Met Glu Lys Thr Cys Ser Lys
        2115                2120                2125
Glu Phe Lys Leu Ser Asn Asn Leu Asn Val Gly Gly Ser Ser Glu
    2130                2135                2140
Asn Asn His Ser Ile Lys Val Ser Pro Tyr Leu Ser Gln Phe Gln Gln
2145                2150                2155                2160
Asp Lys Gln Gln Leu Val Leu Gly Thr Lys Val Ser Leu Val Glu Asn
                2165                2170                2175
Ile His Val Leu Gly Lys Glu Gln Ala Ser Pro Lys Asn Val Lys Met
            2180                2185                2190
Glu Ile Gly Lys Thr Glu Thr Phe Ser Asp Val Pro Val Lys Thr Asn
        2195                2200                2205
Ile Glu Val Cys Ser Thr Tyr Ser Lys Asp Ser Glu Asn Tyr Phe Glu
    2210                2215                2220
Thr Glu Ala Val Glu Ile Ala Lys Ala Phe Met Glu Asp Asp Glu Leu
2225                2230                2235                2240
Thr Asp Ser Lys Leu Pro Ser His Ala Thr His Ser Leu Phe Thr Cys
                2245                2250                2255
Pro Glu Asn Glu Glu Met Val Leu Ser Asn Ser Arg Ile Gly Lys Arg
            2260                2265                2270
Arg Gly Glu Pro Leu Ile Leu Val Gly Glu Pro Ser Ile Lys Arg Asn
        2275                2280                2285
Leu Leu Asn Glu Phe Asp Arg Ile Ile Glu Asn Gln Glu Lys Ser Leu
    2290                2295                2300
Lys Ala Ser Lys Ser Thr Pro Asp Gly Thr Ile Lys Asp Arg Arg Leu
2305                2310                2315                2320
Phe Met His His Val Ser Leu Glu Pro Ile Thr Cys Val Pro Phe Arg
                2325                2330                2335
Thr Thr Lys Glu Arg Gln Glu Ile Gln Asn Pro Asn Phe Thr Ala Pro
            2340                2345                2350
Gly Gln Glu Phe Leu Ser Lys Ser His Leu Tyr Glu His Leu Thr Leu
        2355                2360                2365
Glu Lys Ser Ser Ser Asn Leu Ala Val Ser Gly His Pro Phe Tyr Gln
    2370                2375                2380
Val Ser Ala Thr Arg Asn Glu Lys Met Arg His Leu Ile Thr Thr Gly
2385                2390                2395                2400
Arg Pro Thr Lys Val Phe Val Pro Pro Phe Lys Thr Lys Ser His Phe
                2405                2410                2415
His Arg Val Glu Gln Cys Val Arg Asn Ile Asn Leu Glu Glu Asn Arg
            2420                2425                2430
Gln Lys Gln Asn Ile Asp Gly His Gly Ser Asp Asp Ser Lys Asn Lys
        2435                2440                2445
Ile Asn Asp Asn Glu Ile His Gln Phe Asn Lys Asn Asn Ser Asn Gln
    2450                2455                2460
Ala Ala Ala Val Thr Phe Thr Lys Cys Glu Glu Glu Pro Leu Asp Leu
2465                2470                2475                2480
Ile Thr Ser Leu Gln Asn Ala Arg Asp Ile Gln Asp Met Arg Ile Lys
                2485                2490                2495
Lys Lys Gln Arg Gln Arg Val Phe Pro Gln Pro Gly Ser Leu Tyr Leu
            2500                2505                2510
Ala Lys Thr Ser Thr Leu Pro Arg Ile Ser Leu Lys Ala Ala Val Gly
        2515                2520                2525
```

-continued

```
Gly Gln Val Pro Ser Ala Cys Ser His Lys Gln Leu Tyr Thr Tyr Gly
            2530                2535                2540

Val Ser Lys His Cys Ile Lys Ile Asn Ser Lys Asn Ala Glu Ser Phe
2545                2550                2555                2560

Gln Phe His Thr Glu Asp Tyr Phe Gly Lys Glu Ser Leu Trp Thr Gly
            2565                2570                2575

Lys Gly Ile Gln Leu Ala Asp Gly Gly Trp Leu Ile Pro Ser Asn Asp
            2580                2585                2590

Gly Lys Ala Gly Lys Glu Glu Phe Tyr Arg Ala Leu Cys Asp Thr Pro
            2595                2600                2605

Gly Val Asp Pro Lys Leu Ile Ser Arg Ile Trp Val Tyr Asn His Tyr
            2610                2615                2620

Arg Trp Ile Ile Trp Lys Leu Ala Ala Met Glu Cys Ala Phe Pro Lys
2625                2630                2635                2640

Glu Phe Ala Asn Arg Cys Leu Ser Pro Glu Arg Val Leu Leu Gln Leu
            2645                2650                2655

Lys Tyr Arg Tyr Asp Thr Glu Ile Asp Arg Ser Arg Arg Ser Ala Ile
            2660                2665                2670

Lys Lys Ile Met Glu Arg Asp Asp Thr Ala Ala Lys Thr Leu Val Leu
            2675                2680                2685

Cys Val Ser Asp Ile Ile Ser Leu Ser Ala Asn Ile Ser Glu Thr Ser
            2690                2695                2700

Ser Asn Lys Thr Ser Ser Ala Asp Thr Gln Lys Val Ala Ile Ile Glu
2705                2710                2715                2720

Leu Thr Asp Gly Trp Tyr Ala Val Lys Ala Gln Leu Asp Pro Pro Leu
            2725                2730                2735

Leu Ala Val Leu Lys Asn Gly Arg Leu Thr Val Gly Gln Lys Ile Ile
            2740                2745                2750

Leu His Gly Ala Glu Leu Val Gly Ser Pro Asp Ala Cys Thr Pro Leu
            2755                2760                2765

Glu Ala Pro Glu Ser Leu Met Leu Lys Ile Ser Ala Asn Ser Thr Arg
            2770                2775                2780

Pro Ala Arg Trp Tyr Thr Lys Leu Gly Phe Phe Pro Asp Pro Arg Pro
2785                2790                2795                2800

Phe Pro Leu Pro Leu Ser Ser Leu Phe Ser Asp Gly Gly Asn Val Gly
            2805                2810                2815

Cys Val Asp Val Ile Ile Gln Arg Ala Tyr Pro Ile Gln Arg Met Glu
            2820                2825                2830

Lys Thr Ser Ser Gly Leu Tyr Ile Phe Arg Asn Glu Arg Glu Glu Glu
            2835                2840                2845

Lys Glu Ala Ala Lys Tyr Val Glu Ala Gln Gln Lys Arg Leu Glu Ala
            2850                2855                2860

Leu Phe Thr Lys Ile Gln Glu Glu Phe Glu Glu His Glu Glu Asn Thr
2865                2870                2875                2880

Thr Lys Pro Tyr Leu Pro Ser Arg Ala Leu Thr Arg Gln Gln Val Arg
            2885                2890                2895

Ala Leu Gln Asp Gly Ala Glu Leu Tyr Glu Ala Val Lys Asn Ala Ala
            2900                2905                2910

Asp Pro Ala Tyr Leu Glu Gly Tyr Phe Ser Glu Gln Leu Arg Ala
            2915                2920                2925

Leu Asn Asn His Arg Gln Met Leu Asn Asp Lys Lys Gln Ala Gln Ile
            2930                2935                2940

Gln Leu Glu Ile Arg Lys Ala Met Glu Ser Ala Glu Gln Lys Glu Gln
```

-continued

```
             2945                2950                2955                2960

Gly Leu Ser Arg Asp Val Thr Thr Val Trp Lys Leu Arg Ile Val Ser
                 2965                2970                2975

Tyr Ser Lys Lys Glu Lys Asp Ser Val Ile Leu Ser Ile Trp Arg Pro
                 2980                2985                2990

Ser Ser Asp Leu Tyr Ser Leu Leu Thr Glu Gly Lys Arg Tyr Arg Ile
                 2995                3000                3005

Tyr His Leu Ala Thr Ser Lys Ser Lys Ser Ser Glu Arg Ala Asn
         3010                3015                3020

Ile Gln Leu Ala Ala Thr Lys Lys Thr Gln Tyr Gln Gln Leu Pro Val
3025                3030                3035                3040

Ser Asp Glu Ile Leu Phe Gln Ile Tyr Gln Pro Arg Glu Pro Leu His
                 3045                3050                3055

Phe Ser Lys Phe Leu Asp Pro Asp Phe Gln Pro Ser Cys Ser Glu Val
                 3060                3065                3070

Asp Leu Ile Gly Phe Val Val Ser Val Val Lys Lys Thr Gly Leu Ala
                 3075                3080                3085

Pro Phe Val Tyr Leu Ser Asp Glu Cys Tyr Asn Leu Leu Ala Ile Lys
                 3090                3095                3100

Phe Trp Ile Asp Leu Asn Glu Asp Ile Ile Lys Pro His Met Leu Ile
3105                3110                3115                3120

Ala Ala Ser Asn Leu Gln Trp Arg Pro Glu Ser Lys Ser Gly Leu Leu
                 3125                3130                3135

Thr Leu Phe Ala Gly Asp Phe Ser Val Phe Ser Ala Ser Pro Lys Glu
                 3140                3145                3150

Gly His Phe Gln Glu Thr Phe Asn Lys Met Lys Asn Thr Val Glu Asn
                 3155                3160                3165

Ile Asp Ile Leu Cys Asn Glu Ala Glu Asn Lys Leu Met His Ile Leu
         3170                3175                3180

His Ala Asn Asp Pro Lys Trp Ser Thr Pro Thr Lys Asp Cys Thr Ser
3185                3190                3195                3200

Gly Pro Tyr Thr Ala Gln Ile Ile Pro Gly Thr Gly Asn Lys Leu Leu
                 3205                3210                3215

Met Ser Ser Pro Asn Cys Glu Ile Tyr Tyr Gln Ser Pro Leu Ser Leu
                 3220                3225                3230

Cys Met Ala Lys Arg Lys Ser Val Ser Thr Pro Val Ser Ala Gln Met
                 3235                3240                3245

Thr Ser Lys Ser Cys Lys Gly Glu Lys Glu Ile Asp Asp Gln Lys Asn
         3250                3255                3260

Cys Lys Lys Arg Arg Ala Leu Asp Phe Leu Ser Arg Leu Pro Leu Pro
3265                3270                3275                3280

Pro Pro Val Ser Pro Ile Cys Thr Phe Val Ser Pro Ala Ala Gln Lys
                 3285                3290                3295

Ala Phe Gln Pro Pro Arg Ser Cys Gly Thr Lys Tyr Glu Thr Pro Ile
                 3300                3305                3310

Lys Lys Lys Glu Leu Asn Ser Pro Gln Met Thr Pro Phe Lys Lys Phe
                 3315                3320                3325

Asn Glu Ile Ser Leu Leu Glu Ser Asn Ser Ile Ala Asp Glu Glu Leu
                 3330                3335                3340

Ala Leu Ile Asn Thr Gln Ala Leu Leu Ser Gly Ser Thr Gly Glu Lys
3345                3350                3355                3360

Gln Phe Ile Ser Val Ser Glu Ser Thr Arg Thr Ala Pro Thr Ser Ser
                 3365                3370                3375
```

```
Glu Asp Tyr Leu Arg Leu Lys Arg Arg Cys Thr Thr Ser Leu Ile Lys
        3380            3385            3390

Glu Gln Glu Ser Ser Gln Ala Ser Thr Glu Glu Cys Glu Lys Asn Lys
        3395            3400            3405

Gln Asp Thr Ile Thr Thr Lys Lys Tyr Ile
    3410            3415

(2) INFORMATION FOR SEQ ID NO:5:

(i) SEQUENCE CHARACTERISTICS:
        (A) LENGTH: 10
        (B) TYPE: amino acid
        (C) STRANDEDNESS: single
        (D) TOPOLOGY: unknown (ix) FEATURE:
        (A) NAME/KEY: Granin Consensus Sequence (xi) SEQUENCE DESCRIPTION: SEQ ID NO:5:

Glu Asn Leu Ser Xaa Xaa Asp Xaa Glu Leu
1               5               10

(2) INFORMATION FOR SEQ ID NO:6:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:6:

Glu Asn Leu Ser Ser Glu Asp Glu Glu Leu
1               5               10

(2) INFORMATION FOR SEQ ID NO:7:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:7:

Glu Asn Leu Ser Ser Glu Asp Glu Glu Leu
1               5               10

(2) INFORMATION FOR SEQ ID NO:8:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:8:

Glu Ser Asp Ser Thr Glu Asp Glu Asp Leu
1               5               10

(2) INFORMATION FOR SEQ ID NO:9:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:9:
```

Glu Ser Asn Ser Ile Ala Asp Glu Glu Leu
1               5                   10

(2) INFORMATION FOR SEQ ID NO:10:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:10:

Glu Ser Leu Ser Ala Ile Glu Ala Glu Leu
1               5                   10

(2) INFORMATION FOR SEQ ID NO:11:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:11:

Glu Ser Leu Ser Ala Ile Glu Ala Glu Leu
1               5                   10

(2) INFORMATION FOR SEQ ID NO:12:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:12:

Glu Ser Leu Ser Ala Ile Glu Ala Glu Leu
1               5                   10

(2) INFORMATION FOR SEQ ID NO:13:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:13:

Glu Ser Leu Ser Ala Ile Glu Ala Glu Leu
1               5                   10

(2) INFORMATION FOR SEQ ID NO:14:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:14:

Glu Asn Leu Ala Ala Met Asp Leu Glu Leu
1               5                   10

(2) INFORMATION FOR SEQ ID NO:15:

(i) SEQUENCE CHARACTERISTICS:
        (A) LENGTH: 10

```
            (B) TYPE: amino acid
            (C) STRANDEDNESS: single
            (D) TOPOLOGY: unknown (xi) SEQUENCE DESCRIPTION: SEQ ID NO:15:

Glu Asn Leu Ala Ala Met Asp Leu Glu Leu
1               5                  10

(2) INFORMATION FOR SEQ ID NO:16:

(i) SEQUENCE CHARACTERISTICS:
            (A) LENGTH: 10
            (B) TYPE: amino acid
            (C) STRANDEDNESS: single
            (D) TOPOLOGY: unknown (xi) SEQUENCE DESCRIPTION: SEQ ID NO:16:

Glu Asn Leu Ala Ala Met Asp Leu Glu Leu
1               5                  10

(2) INFORMATION FOR SEQ ID NO:17:

(i) SEQUENCE CHARACTERISTICS:
            (A) LENGTH: 10
            (B) TYPE: amino acid
            (C) STRANDEDNESS: single
            (D) TOPOLOGY: unknown (xi) SEQUENCE DESCRIPTION: SEQ ID NO:17:

Glu Asn Leu Asn Asp Lys Asp Gln Glu Leu
1               5                  10

(2) INFORMATION FOR SEQ ID NO:18:

(i) SEQUENCE CHARACTERISTICS:
            (A) LENGTH: 10
            (B) TYPE: amino acid
            (C) STRANDEDNESS: single
            (D) TOPOLOGY: unknown (xi) SEQUENCE DESCRIPTION: SEQ ID NO:18:

Glu Asn Leu Asn Asp Lys Asp Gln Glu Leu
1               5                  10

(2) INFORMATION FOR SEQ ID NO:19:

(i) SEQUENCE CHARACTERISTICS:
            (A) LENGTH: 10
            (B) TYPE: amino acid
            (C) STRANDEDNESS: single
            (D) TOPOLOGY: unknown (xi) SEQUENCE DESCRIPTION: SEQ ID NO:19:

Asp Asn Leu Asn Asp Lys Asp Gln Glu Leu
1               5                  10

(2) INFORMATION FOR SEQ ID NO:20:

(i) SEQUENCE CHARACTERISTICS:
            (A) LENGTH: 10
            (B) TYPE: amino acid
            (C) STRANDEDNESS: single
            (D) TOPOLOGY: unknown (xi) SEQUENCE DESCRIPTION: SEQ ID NO:20:

Glu Asn Leu Asn Xaa Xaa Asp Gln Glu Leu
1               5                  10
```

(2) INFORMATION FOR SEQ ID NO:21:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:21:

```
Glu Asn Leu Asp Glu Thr Ile Ala Leu Gln
1               5                   10
```

(2) INFORMATION FOR SEQ ID NO:22:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:22:

```
Glu Asn Leu Asp Glu Thr Ile Ala Leu Gln
1               5                   10
```

(2) INFORMATION FOR SEQ ID NO:23:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:23:

```
Gly Asn Ile Pro Asn Ile Val Ala Glu Leu
1               5                   10
```

(2) INFORMATION FOR SEQ ID NO:24:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:24:

```
Gly Asn Ile Pro Asn Ile Val Ala Glu Leu
1               5                   10
```

(2) INFORMATION FOR SEQ ID NO:25:

(i) SEQUENCE CHARACTERISTICS:
        (A) LENGTH: 10
        (B) TYPE: amino acid
        (C) STRANDEDNESS: single
        (D) TOPOLOGY: unknown (xi) SEQUENCE DESCRIPTION: SEQ ID NO:25:

```
Gly Asn Ile Pro Asn Ile Val Ala Glu Leu
1               5                   10
```

(2) INFORMATION FOR SEQ ID NO:26:

(i) SEQUENCE CHARACTERISTICS:
        (A) LENGTH: 10
        (B) TYPE: amino acid
        (C) STRANDEDNESS: single
        (D) TOPOLOGY: unknown -continued (xi) SEQUENCE DESCRIPTION: SEQ ID NO:26:

```
Gly Asn Ile Pro Asn Ile Val Ala Glu Leu
1               5                   10
```

What is claimed is:

1. A method to reduce the growth of a prostate tumor in a mammal, comprising: injecting into said prostate tumor a retroviral construct comprising a BRCA1 nucleic acid sequence operably linked to a promoter and encoding a BRCA1 polypeptide having tumor suppressor activity, wherein said BRCA1 polypeptide is expressed in said prostate tumor at a level and for a period of time sufficient to reduce the growth of said prostate tumor.

2. The method of claim 1, wherein said tumor is gene-linked hereditary prostate cancer.

3. The method of claim 1, wherein said tumor is sporadic prostate cancer.

4. The method of claim 1, wherein said BRCA1 polypeptide is a wild type BRCA1 polypeptide.

5. The method of claim 4, wherein the retroviral construct is an LXSN retroviral construct.

6. The method of claim 4, wherein said BRCAI nucleic acid sequence encoding said BRCA1 polypeptide is selected from the group consisting of:

(a) a nucleic acid sequence as set forth in SEQ ID NO: 1; and (b) a nucleic acid sequence encoding a polypeptide as set forth in SEQ ID NO:2.

7. The method of claim 4, wherein said tumor is gene-linked hereditary prostate cancer.

8. The method of claim 4, wherein said tumor is sporadic prostate cancer.

* * * * *